(12) United States Patent
Messerly et al.

(10) Patent No.: US 12,214,224 B2
(45) Date of Patent: Feb. 4, 2025

(54) GENERATOR FOR USE WITH AN ULTRASONIC SURGICAL INSTRUMENT

(71) Applicant: Cilag GmbH International, Zug (CH)

(72) Inventors: Jeffrey D. Messerly, Cincinnati, OH (US); Eitan T. Wiener, Loveland, OH (US); Brian T. Noyes, Yonkers, NY (US); Jeffrey L. Aldridge, Lebanon, OH (US); James R. Giordano, Milford, OH (US); Robert J. Beetel, III, Sunnyvale, CA (US); Daniel J. Abbott, Maple Valley, WA (US); Foster B. Stulen, Johns Island, SC (US); Matthew C. Miller, Cincinnati, OH (US); Aaron C. Voegele, Loveland, OH (US); Jeffrey P. Wiley, Milford, OH (US); Nathan J. Price, Albuquerque, NM (US); Daniel W. Price, Loveland, OH (US); Robert L. Koch, Jr., Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/530,709

(22) Filed: Dec. 6, 2023

(65) Prior Publication Data
US 2024/0165429 A1    May 23, 2024

Related U.S. Application Data

(60) Continuation of application No. 16/448,089, filed on Jun. 21, 2019, now Pat. No. 11,890,491, which is a
(Continued)

(51) Int. Cl.
*A61N 7/00* (2006.01)
*A61B 18/14* (2006.01)
(Continued)

(52) U.S. Cl.
CPC ............... *A61N 7/00* (2013.01); *A61B 18/14* (2013.01); *A61N 7/02* (2013.01); *B06B 1/0284* (2013.01);
(Continued)

(58) Field of Classification Search
CPC .......... A61N 7/00; A61N 7/02; B06B 1/0284; B06B 1/0215; B06B 1/0261;
(Continued)

(56) References Cited

U.S. PATENT DOCUMENTS

| 4,574,615 A | 3/1986 | Bower et al. |
| 4,712,722 A | 12/1987 | Hood et al. |

(Continued)

FOREIGN PATENT DOCUMENTS

| EP | 1862133 A1 | 12/2007 |
| JP | 2010009686 A | 1/2010 |

(Continued)

*Primary Examiner* — Emily P Pham

(57) ABSTRACT

A generator comprising an interface and a control circuit is disclosed. The interface is to electrically couple to an ultrasonic surgical instrument comprising a switch. The switch is configurable between a first switch state and a second switch state. The control circuit is to provide a continuous drive signal to the ultrasonic surgical instrument based on the switch being in the first switch state. The control circuit is to provide a pulsed drive signal to the ultrasonic surgical instrument based on the switch being in the second switch state.

20 Claims, 41 Drawing Sheets

Related U.S. Application Data continuation of application No. 15/290,570, filed on Oct. 11, 2016, now Pat. No. 10,335,614, which is a continuation of application No. 14/664,233, filed on Mar. 20, 2015, now Pat. No. 9,504,855, which is a division of application No. 12/896,351, filed on Oct. 1, 2010, now Pat. No. 9,089,360, which is a continuation-in-part of application No. 12/503,775, filed on Jul. 15, 2009, now Pat. No. 8,058,771.

(60) Provisional application No. 61/086,619, filed on Aug. 6, 2008, provisional application No. 61/188,790, filed on Aug. 13, 2008, provisional application No. 61/250,217, filed on Oct. 9, 2009.

(51) Int. Cl.
  *A61N 7/02* (2006.01)
  *B06B 1/02* (2006.01)
  *G05B 15/02* (2006.01)
  *A61B 5/00* (2006.01)
  *A61B 5/053* (2021.01)
  *A61B 17/00* (2006.01)
  *A61B 17/32* (2006.01)
  *A61B 18/00* (2006.01)
  *A61B 18/12* (2006.01)

(52) U.S. Cl.
  CPC .............. *G05B 15/02* (2013.01); *A61B 5/053* (2013.01); *A61B 5/4836* (2013.01); *A61B 2017/00026* (2013.01); *A61B 2017/00084* (2013.01); *A61B 2017/00176* (2013.01); *A61B 2017/00203* (2013.01); *A61B 2017/00973* (2013.01); *A61B 2017/320093* (2017.08); *A61B 2017/320094* (2017.08); *A61B 2017/320095* (2017.08); *A61B 2018/00005* (2013.01); *A61B 2018/00303* (2013.01); *A61B 2018/00589* (2013.01); *A61B 2018/00601* (2013.01); *A61B 2018/0063* (2013.01); *A61B 2018/00666* (2013.01); *A61B 2018/00791* (2013.01); *A61B 2018/00845* (2013.01); *A61B 2018/00875* (2013.01); *A61B 2018/00994* (2013.01); *A61B 18/1206* (2013.01); *A61B 18/1445* (2013.01); *B06B 2201/76* (2013.01)

(58) Field of Classification Search
  CPC . B06B 2201/76; B06B 2201/55; A61B 5/053; A61B 5/4836; A61B 18/14; A61B 18/1206; A61B 18/1445; A61B 2017/00398; A61B 2017/00734; A61B 2017/320068; A61B 2017/00017; A61B 2017/320092; A61B 2017/00026; A61B 2017/00084; A61B 2017/00176; A61B 2017/00203; A61B 2017/00973; A61B 2017/320093; A61B 2017/320094; A61B 2017/320095; A61B 2017/0003; A61B 2018/00994; A61B 2018/00005; A61B 2018/00303; A61B 2018/00589; A61B 2018/00601; A61B 2018/0063; A61B 2018/00666; A61B 2018/00791; A61B 2018/00845; A61B 2018/00875; G05B 15/02

See application file for complete search history.

(56) References Cited

U.S. PATENT DOCUMENTS

| | | |
|---|---|---|
| 4,827,911 A | 5/1989 | Broadwin et al. |
| 4,965,532 A | 10/1990 | Sakurai |
| 5,322,055 A | 6/1994 | Davison et al. |
| 5,449,370 A | 9/1995 | Vaitekunas |
| 5,630,420 A | 5/1997 | Vaitekunas |
| 5,935,144 A | 8/1999 | Estabrook |
| 5,938,633 A | 8/1999 | Beaupre |
| 5,944,737 A | 8/1999 | Tsonton et al. |
| 6,024,741 A | 2/2000 | Williamson, IV et al. |
| 6,027,515 A | 2/2000 | Cimino |
| 6,033,399 A | 3/2000 | Gines |
| 6,261,286 B1 | 7/2001 | Goble et al. |
| 6,436,129 B1 | 8/2002 | Sharkey et al. |
| 6,454,781 B1 | 9/2002 | Witt et al. |
| 6,480,796 B2 | 11/2002 | Wiener |
| 6,537,291 B2 | 3/2003 | Friedman et al. |
| 6,626,926 B2 | 9/2003 | Friedman et al. |
| 6,633,234 B2 | 10/2003 | Wiener et al. |
| 6,662,127 B2 | 12/2003 | Wiener et al. |
| 6,678,621 B2 | 1/2004 | Wiener et al. |
| 6,679,899 B2 | 1/2004 | Wiener et al. |
| 6,908,472 B2 | 6/2005 | Wiener et al. |
| 6,977,495 B2 | 12/2005 | Donofrio |
| 7,077,853 B2 | 7/2006 | Kramer et al. |
| 7,179,271 B2 | 2/2007 | Friedman et al. |
| 7,273,483 B2 | 9/2007 | Wiener et al. |
| 8,058,771 B2 | 11/2011 | Giordano et al. |
| 8,152,801 B2 | 4/2012 | Goldberg et al. |
| 8,328,833 B2 | 12/2012 | Cuny |
| 9,089,360 B2 | 7/2015 | Messerly et al. |
| 9,282,989 B2 * | 3/2016 | Boukhny ............ A61M 3/0216 |
| 9,504,855 B2 | 11/2016 | Messerly et al. |
| 10,335,614 B2 | 7/2019 | Messerly et al. |
| 11,890,491 B2 | 2/2024 | Messerly et al. |
| 2002/0049551 A1 | 4/2002 | Friedman et al. |
| 2002/0177373 A1 | 11/2002 | Shibata et al. |
| 2004/0092921 A1 | 5/2004 | Kadziauskas et al. |
| 2005/0288659 A1 | 12/2005 | Kimura et al. |
| 2006/0264809 A1 | 11/2006 | Hansmann et al. |
| 2007/0016235 A1 | 1/2007 | Tanaka et al. |
| 2007/0056596 A1 | 3/2007 | Fanney et al. |
| 2007/0249941 A1 | 10/2007 | Salehi et al. |
| 2009/0259149 A1 | 10/2009 | Tahara et al. |

FOREIGN PATENT DOCUMENTS

| | | |
|---|---|---|
| JP | 2010121865 A | 6/2010 |
| KR | 100789356 B1 | 12/2007 |

* cited by examiner

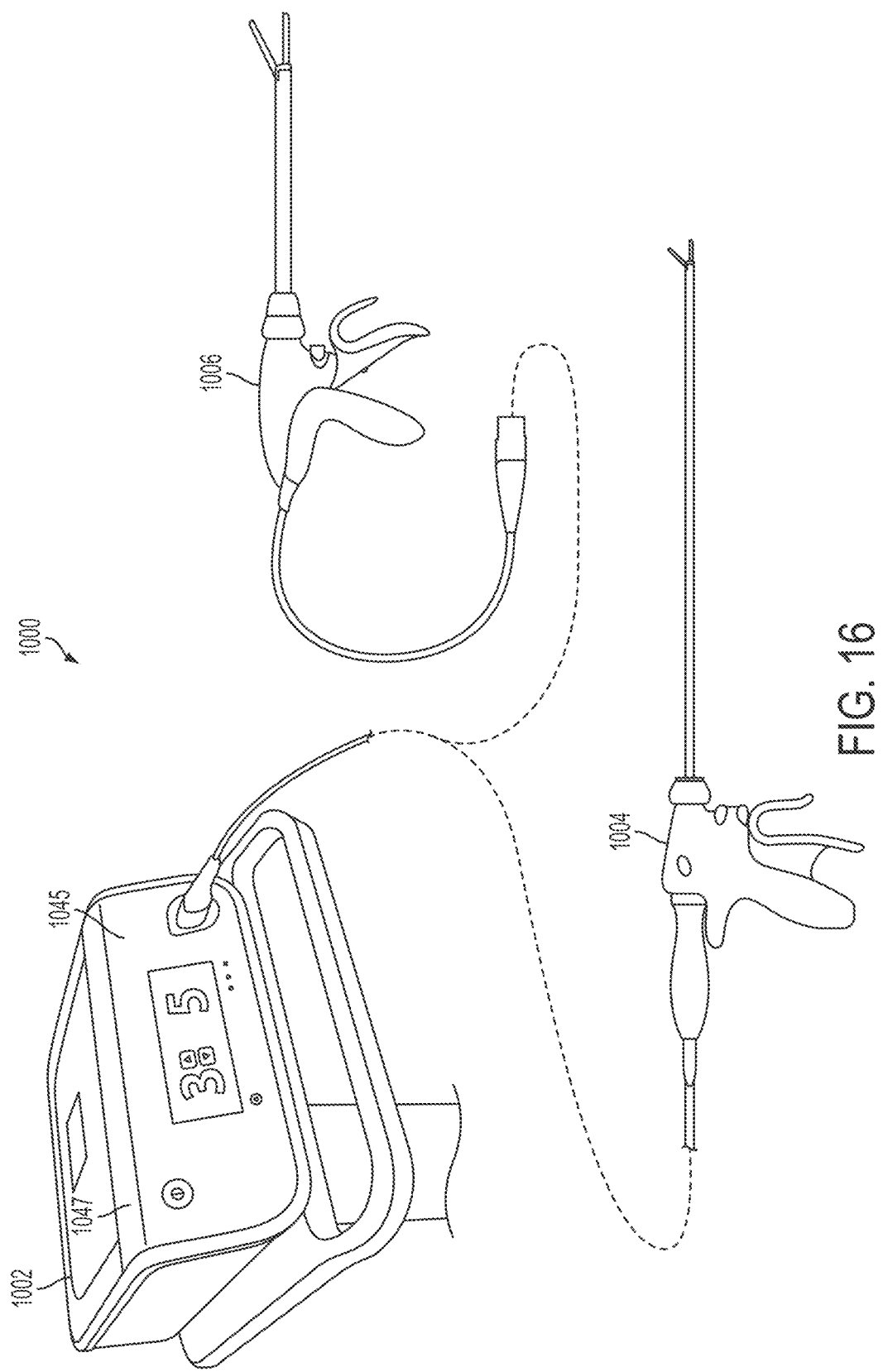

GENERATOR FOR USE WITH AN ULTRASONIC SURGICAL INSTRUMENT

CROSS-REFERENCE TO RELATED APPLICATIONS

This application is a continuation application claiming priority under 35 U.S.C. § 120 to U.S. patent application Ser. No. 16/448,089, entitled DEVICES AND TECHNIQUES FOR CUTTING AND COAGULATING TISSUE, filed Jun. 21, 2019, now U.S. Patent Application Publication No. 2020/0078609, which is a continuation application claiming priority under 35 U.S.C. § 120 to U.S. patent application Ser. No. 15/290,570, entitled DEVICES AND TECHNIQUES FOR CUTTING AND COAGULATING TISSUE, filed Oct. 11, 2016, which issued on Jul. 2, 2019 as U.S. Pat. No. 10,335,614, which is a continuation application claiming priority under 35 U.S.C. § 120 to U.S. patent application Ser. No. 14/664,233, entitled DEVICES AND TECHNIQUES FOR CUTTING AND COAGULATING TISSUE, filed Mar. 20, 2015, which issued on Nov. 29, 2016 as U.S. Pat. No. 9,504,855, which is a divisional application claiming priority under 35 U.S.C. § 121 to U.S. patent application Ser. No. 12/896,351, entitled DEVICE AND TECHNIQUE FOR CUTTING AND COAGULATING TISSUE, filed Oct. 1, 2010, which issued on Jul. 28, 2015 as U.S. Pat. No. 9,089,360, which is a continuation-in-part application claiming priority under of 35 U.S.C. § 120 to U.S. patent application Ser. No. 12/503,775, entitled ULTRASONIC DEVICE FOR CUTTING AND COAGULATING WITH STEPPED OUTPUT, filed Jul. 15, 2009, which issued on Nov. 15, 2011 as U.S. Pat. No. 8,058,771, which claims the benefit under 35 U.S.C. § 119(e), of (1) U.S. Provisional Patent Application Ser. No. 61/086,619, entitled ULTRASONIC DEVICE FOR CUTTING AND COAGULATING WITH STEPPED OUTPUT, filed Aug. 6, 2008 and (2) U.S. Provisional Patent Application Ser. No. 61/188,790, entitled ULTRASONIC DEVICE FOR CUTTING AND COAGULATING WITH STEPPED OUTPUT, filed Aug. 13, 2008, the entire disclosures of which are hereby incorporated by reference herein.

U.S. patent application Ser. No. 12/896,351 also claims the benefit under 35 U.S.C. § 119(e), of U.S. Provisional Patent Application Ser. No. 61/250,217, entitled A DUAL BIPOLAR AND ULTRASONIC GENERATOR FOR ELECTRO-SURGICAL INSTRUMENTS, filed Oct. 9, 2009, the entire disclosure of which is hereby incorporated by reference herein.

TECHNICAL FIELD

The present disclosure generally relates to ultrasonic surgical systems and, more particularly, to an ultrasonic system that allows surgeons to perform cutting and coagulation.

BACKGROUND

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and hemostasis by coagulation, desirably minimizing patient trauma. The cutting action is typically realized by an-end effector, or blade tip, at the distal end of the instrument, which transmits ultrasonic energy to tissue brought into contact with the end effector. Ultrasonic instruments of this nature can be configured for open surgical use, laparoscopic, or endoscopic surgical procedures including robotic-assisted procedures.

Some surgical instruments utilize ultrasonic energy for both precise cutting and controlled coagulation. Ultrasonic energy cuts and coagulates by using lower temperatures than those used by electrosurgery. Vibrating at high frequencies (e.g., 55,500 times per second), the ultrasonic blade denatures protein in the tissue to form a sticky coagulum. Pressure exerted on tissue with the blade surface collapses blood vessels and allows the coagulum to form a hemostatic seal. The precision of cutting and coagulation is controlled by the surgeon's technique and adjusting the power level, blade edge, tissue traction, and blade pressure.

A primary challenge of ultrasonic technology for medical devices, however, continues to be sealing of blood vessels. Work done by the applicant and others has shown that optimum vessel sealing occurs when the inner muscle layer of a vessel is separated and moved away from the adventitia layer prior to the application of standard ultrasonic energy. Current efforts to achieve this separation have involved increasing the clamp force applied to the vessel.

Furthermore, the user does not always have visual feedback of the tissue being cut. Accordingly, it would be desirable to provide some form of feedback to indicate to the user that the cut is complete when visual feedback is unavailable. Moreover, without some form of feedback indicator to indicate that the cut is complete, the user may continue to activate the harmonic instrument even though the cut is complete, which cause possible damage to the harmonic instrument and surrounding tissue by the heat that is generated when activating a harmonic instrument with little to nothing between the jaws.

The ultrasonic transducer may be modeled as an equivalent circuit having first branch comprising a static capacitance and a second "motional" branch comprising a serially connected inductance, resistance and capacitance that defines the electromechanical properties of the resonator. Conventional ultrasonic generators may include a tuning inductor for tuning out the static capacitance at a resonant frequency so that substantially all of generator's current output flows into the motional branch. The motional branch current, along with the drive voltage, define the impedance and phase magnitude. Accordingly, using a tuning inductor, the generator's current output represents the motional branch current, and the generator is thus able to maintain its drive output at the ultrasonic transducer's resonant frequency. The tuning inductor also transforms the phase impedance plot of the ultrasonic transducer to improve the generator's frequency lock capabilities. However, the tuning inductor must be matched with the specific static capacitance of an ultrasonic transducer. A different ultrasonic transducer having a different static capacitance requires a different tuning inductor.

Electrosurgical devices for applying electrical energy to tissue in order to treat and/or destroy the tissue are also finding increasingly widespread applications in surgical procedures. An electrosurgical device typically includes a handpiece, an instrument having a distally-mounted end effector (e.g., one or more electrodes). The end effector can be positioned against the tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flowing through the tissue may form hemostatic seals within the tissue and/or between tissues and thus may be particularly useful for sealing blood vessels, for example. The end effector of an electrosurgical device may also include a cutting member that is movable relative to the tissue and the electrodes to transect the tissue.

Electrical energy applied by an electrosurgical device can be transmitted to the instrument by a generator in communication with the handpiece. The electrical energy may be in the form of radio frequency ("RF") energy. RF energy is a form of electrical energy that may be in the frequency range of 300 kilohertz (kHz) to 1 megahertz (MHz). In application, an electrosurgical device can transmit low frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat.

Due to their unique drive signal, sensing and feedback needs, ultrasonic and electrosurgical instruments have generally required dedicated generators. Additionally, in cases where the instrument is disposable or interchangeable with a handpiece, ultrasonic and electrosurgical generators are limited in their ability to recognize the particular instrument configuration being used and to optimize control and diagnostic processes accordingly. Moreover, capacitive coupling of signals from the generator into patient-isolated circuits, especially in cases of higher voltage and frequency ranges, may result in exposure of a patient to unacceptable levels of leakage current.

It would be desirable to provide a surgical instrument that overcomes some of the deficiencies of current instruments. The surgical system described herein overcomes those deficiencies.

SUMMARY

One embodiment discloses a method of driving an end effector coupled to an ultrasonic drive system of a surgical instrument. The method comprises generating at least one electrical signal by a generator. The at least one electrical signal is monitored against a first set of logic conditions. A first response of the generator is triggered when the first set of logic conditions is met. A parameter associated with the surgical instrument is determined from the at least one electrical signal.

In various embodiments, a generator comprising an interface and a control circuit is disclosed. The interface is to electrically couple to an ultrasonic surgical instrument comprising a switch. The switch is configurable between a first switch state and a second switch state. The control circuit is to provide a continuous drive signal to the ultrasonic surgical instrument based on the switch being in the first switch state. The control circuit is to provide a pulsed drive signal to the ultrasonic surgical instrument based on the switch being in the second switch state.

In various embodiments, a generator for use with an ultrasonic surgical instrument comprising a switch is disclosed. The switch is configurable between a first switch state and a second switch state. The generator comprises a control circuit. The control circuit is to provide a continuous drive signal to the ultrasonic surgical instrument based on the switch being in the first switch state. The control circuit is to provide a pulsed drive signal to the ultrasonic surgical instrument based on the switch being in the second switch state.

In various embodiments, a generator comprising an interface and a control circuit is disclosed. The interface is to electrically couple to an ultrasonic surgical instrument comprising an ultrasonic transducer and a switch. The switch is configurable between a first switch state and a second switch state. The control circuit is to provide a continuous drive signal to the ultrasonic transducer based on the switch being in the first switch state. The control circuit is to provide a pulsed drive signal to the ultrasonic transducer based on the switch being in the second switch state.

FIGURES

The novel features of the described embodiments are set forth with particularity in the appended claims. The described embodiments, however, both as to organization and methods of operation, may be best understood by reference to the following description, taken in conjunction with the accompanying drawings in which:

FIG. 16 illustrates one embodiment of a surgical system comprising a generator and various surgical instruments usable therewith.

DESCRIPTION

Figure 1:
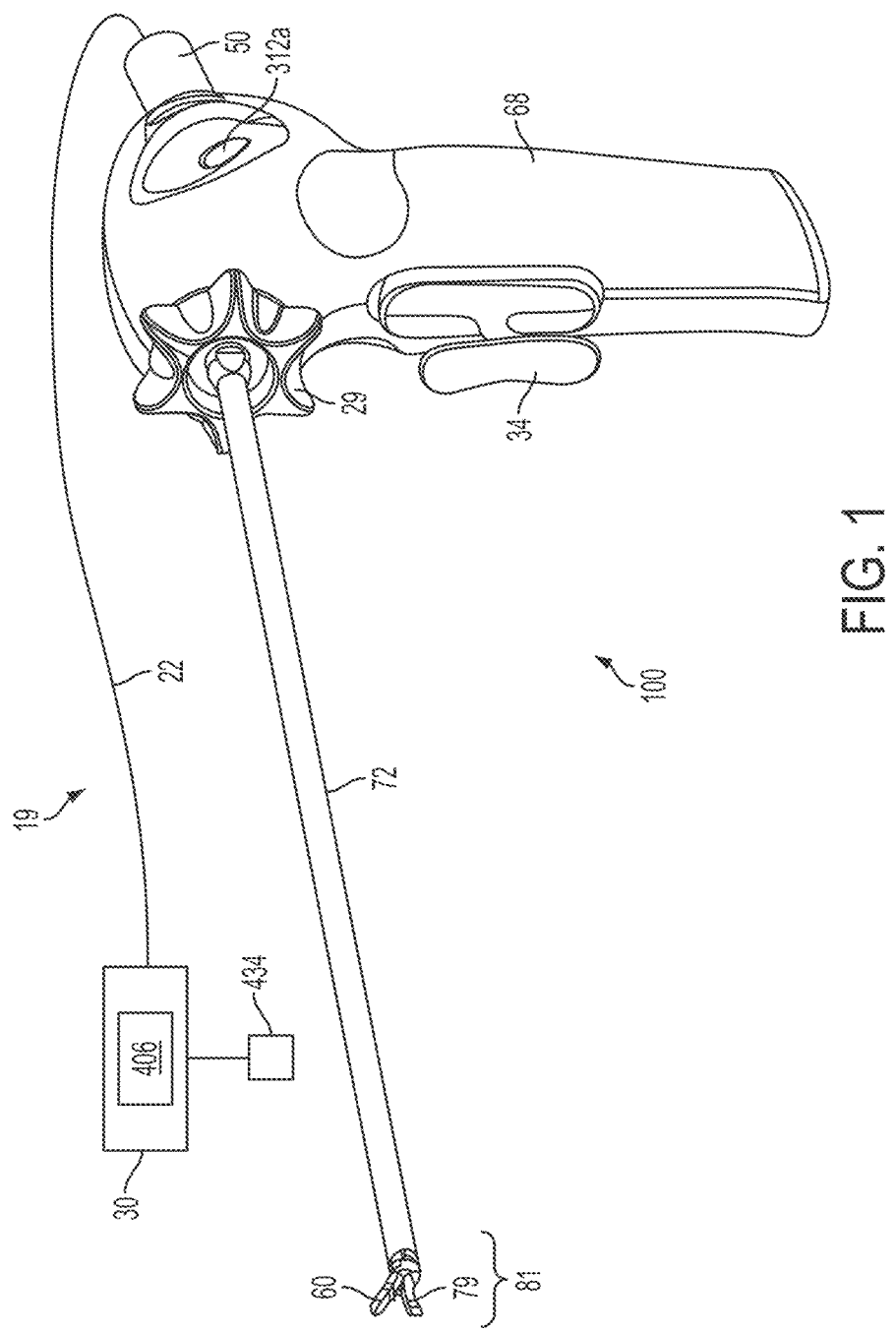
FIG. 1 is a perspective view illustrating one embodiment of an ultrasonic surgical instrument.

Before explaining various embodiments of ultrasonic surgical instruments in detail, it should be noted that the illustrative embodiments are not limited in application or use to the details of construction and arrangement of parts illustrated in the accompanying drawings and description. The illustrative embodiments may be implemented or incorporated in other embodiments, variations and modifications, and may be practiced or carried out in various ways. Further, unless otherwise indicated, the terms and expressions employed herein have been chosen for the purpose of describing the illustrative embodiments for the convenience of the reader and are not for the purpose of limitation thereof.

Further, it is understood that any one or more of the following-described embodiments, expressions of embodiments, examples, can be combined with any one or more of the other following-described embodiments, expressions of embodiments, and examples.

Various embodiments are directed to improved ultrasonic surgical instruments configured for effecting tissue dissecting, cutting, and/or coagulation during surgical procedures. In one embodiment, an ultrasonic surgical instrument apparatus is configured for use in open surgical procedures, but has applications in other types of surgery, such as laparoscopic, endoscopic, and robotic-assisted procedures. Versatile use is facilitated by selective use of ultrasonic energy.

The various embodiments will be described in combination with an ultrasonic instrument as described herein. Such description is provided by way of example, and not limitation, and is not intended to limit the scope and applications thereof. For example, any one of the described embodiments is useful in combination with a multitude of ultrasonic instruments including those described in, for example, U.S. Pat. Nos. 5,938,633; 5,935,144; 5,944,737; 5,322,055; 5,630,420; and 5,449,370.

As will become apparent from the following description, it is contemplated that embodiments of the surgical instrument described herein may be used in association with an oscillator unit of a surgical system, whereby ultrasonic energy from the oscillator unit provides the desired ultrasonic actuation for the present surgical instrument. It is also contemplated that embodiments of the surgical instrument described herein may be used in association with a signal generator unit of a surgical system, whereby electrical energy in the form of radio frequencies (RF), for example, is used to provide feedback to the user regarding the surgical instrument. The ultrasonic oscillator and/or the signal generator unit may be non-detachably integrated with the surgical instrument or may be provided as separate components, which can be electrically attachable to the surgical instrument.

One embodiment of the present surgical apparatus is particularly configured for disposable use by virtue of its straightforward construction. However, it is also contemplated that other embodiments of the present surgical instrument can be configured for non-disposable or multiple uses. Detachable connection of the present surgical instrument with an associated oscillator and signal generator unit is presently disclosed for single-patient use for illustrative purposes only. However, non-detachable integrated connection of the present surgical instrument with an associated oscillator and/or signal generator unit is also contemplated. Accordingly, various embodiments of the presently described surgical instruments may be configured for single use and/or multiple use with either detachable and/or non-detachable integral oscillator and/or signal generator unit, without limitation, and all combinations of such configurations are contemplated to be within the scope of the present disclosure.

Figure 2:
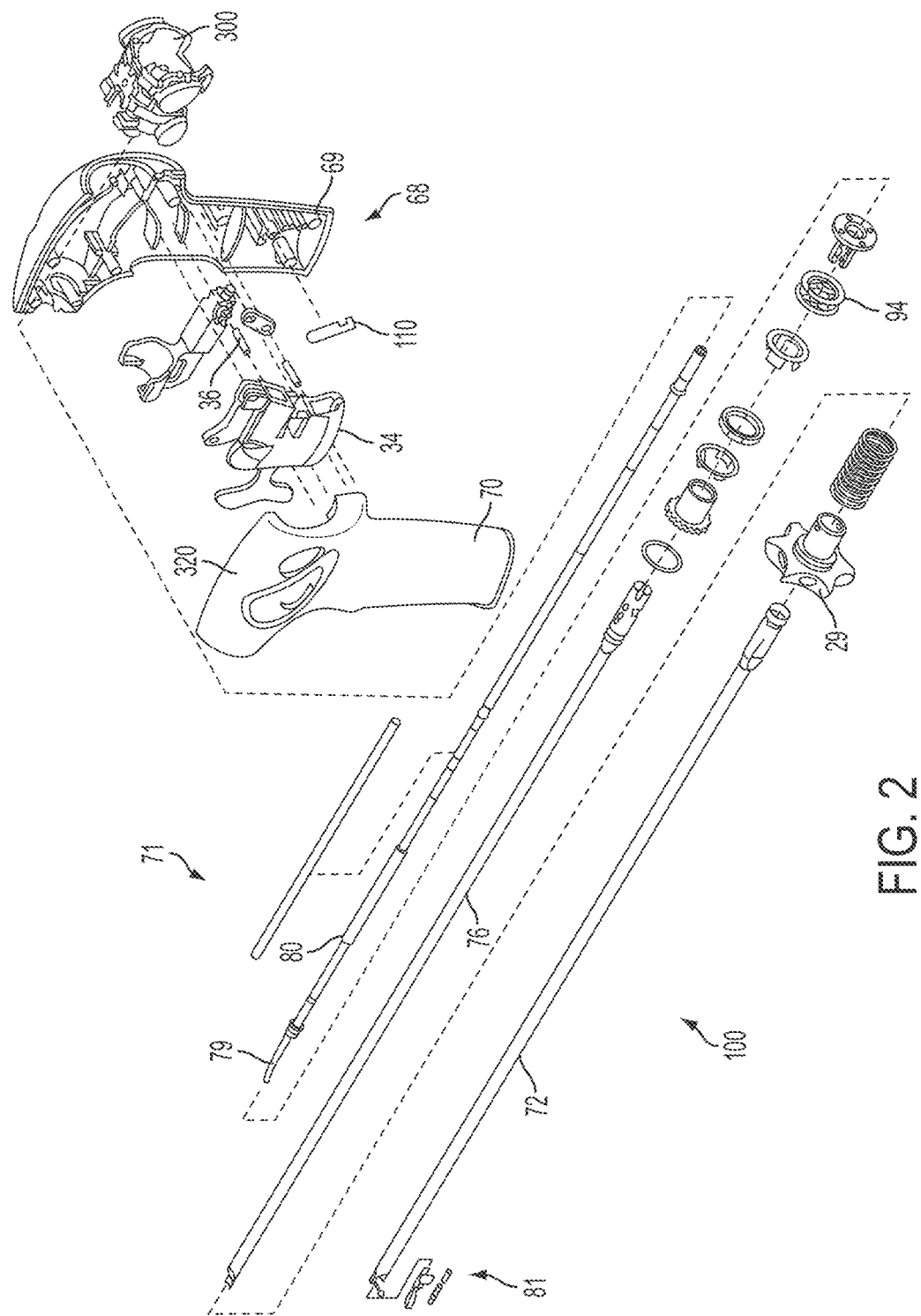
FIG. 2 is an exploded perspective assembly view of one embodiment of an ultrasonic surgical instrument.
Figure 3:
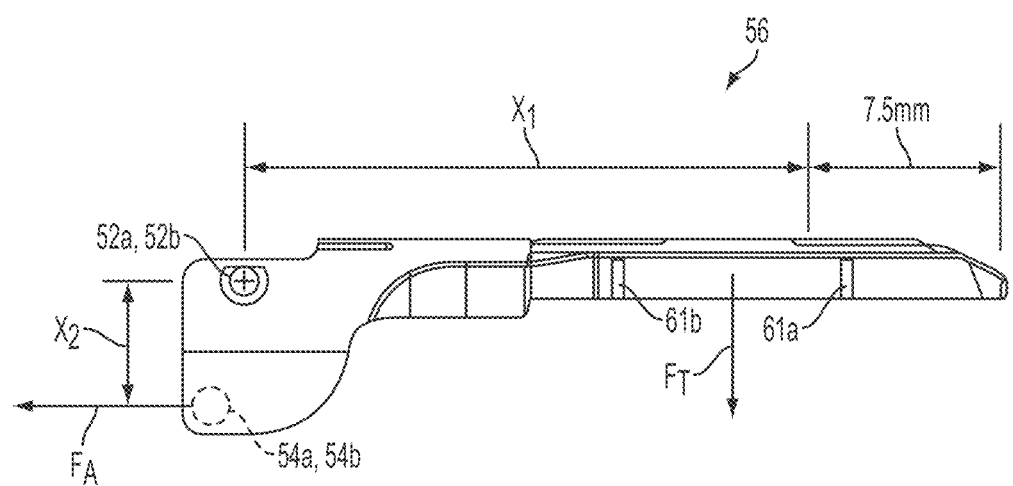
FIG. 3 is a schematic of one embodiment of a clamp arm illustrating force calculations.

With reference to FIGS. 1-3, one embodiment of a surgical system 19 including an ultrasonic surgical instrument 100 is illustrated. The surgical system 19 includes an ultrasonic generator 30 connected to an ultrasonic transducer 50 via a suitable transmission medium such as a cable 22, and an ultrasonic surgical instrument 100. Although in the presently disclosed embodiment, the generator 30 is shown separate from the surgical instrument 100, in one embodiment, the generator 30 may be formed integrally with the surgical instrument 100 to form a unitary surgical system 19. The generator 30 comprises an input device 406 located on a front panel of the generator 30 console. The input device 406 may comprise any suitable device that generates signals suitable for programming the operation of the generator 30 as subsequently described with reference to FIG. 9. Still with reference to FIGS. 1-3, the cable 22 may comprise multiple electrical conductors for the application of electrical energy to positive (+) and negative (−) electrodes of the ultrasonic transducer 50. It will be noted that, in some applications, the ultrasonic transducer 50 may be referred to as a "handle assembly" because the surgical instrument 100 of the surgical system 19 may be configured such that a surgeon may grasp and manipulate the ultrasonic transducer 50 during various procedures and operations. A suitable generator 30 is the GEN 300 sold by Ethicon Endo-Surgery, Inc. of Cincinnati, Ohio as is disclosed in one or more of the following U.S. patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting a Loose Blade in a Handle Connected to an Ultrasonic Surgical System); U.S. Pat. No. 6,626,926 (Method for Driving an Ultrasonic System to Improve Acquisition of Blade Resonance Frequency at Startup); U.S. Pat. No. 6,633,234 (Method for Detecting Blade Breakage Using Rate and/or Impedance Information); U.S. Pat. No. 6,662,127 (Method for Detecting Presence of a Blade in an Ultrasonic System); U.S. Pat. No. 6,678,621 (Output Displacement Control Using Phase Margin in an Ultrasonic Surgical Handle); U.S. Pat. No. 6,679,899 (Method for Detecting Transverse Vibrations in an Ultrasonic Handle); U.S. Pat. No. 6,908,472 (Apparatus and Method for Altering Generator Functions in an Ultrasonic Surgical System); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273, 483 (Apparatus and Method for Alerting Generator Function in an Ultrasonic Surgical System).

In accordance with the described embodiments, the ultrasonic generator 30 produces an electrical signal of a particular voltage, current, and frequency, e.g., 55,500 cycles per second (Hz). The generator is 30 connected by the cable 22 to the handle assembly 68, which contains piezoceramic elements forming the ultrasonic transducer 50. In response to a switch 312a on the handle assembly 68 or a foot switch 434 connected to the generator 30 by another cable the generator signal is applied to the transducer 50, which causes a longitudinal vibration of its elements. A structure connects the transducer 50 to a surgical blade 79, which is thus vibrated at ultrasonic frequencies when the generator signal is applied to the transducer 50. The structure is designed to resonate at the selected frequency, thus amplifying the motion initiated by the transducer 50. In one embodiment, the generator 30 is configured to produce a particular voltage, current, and/or frequency output signal that can be stepped with high resolution, accuracy, and repeatability.

Figure 4:
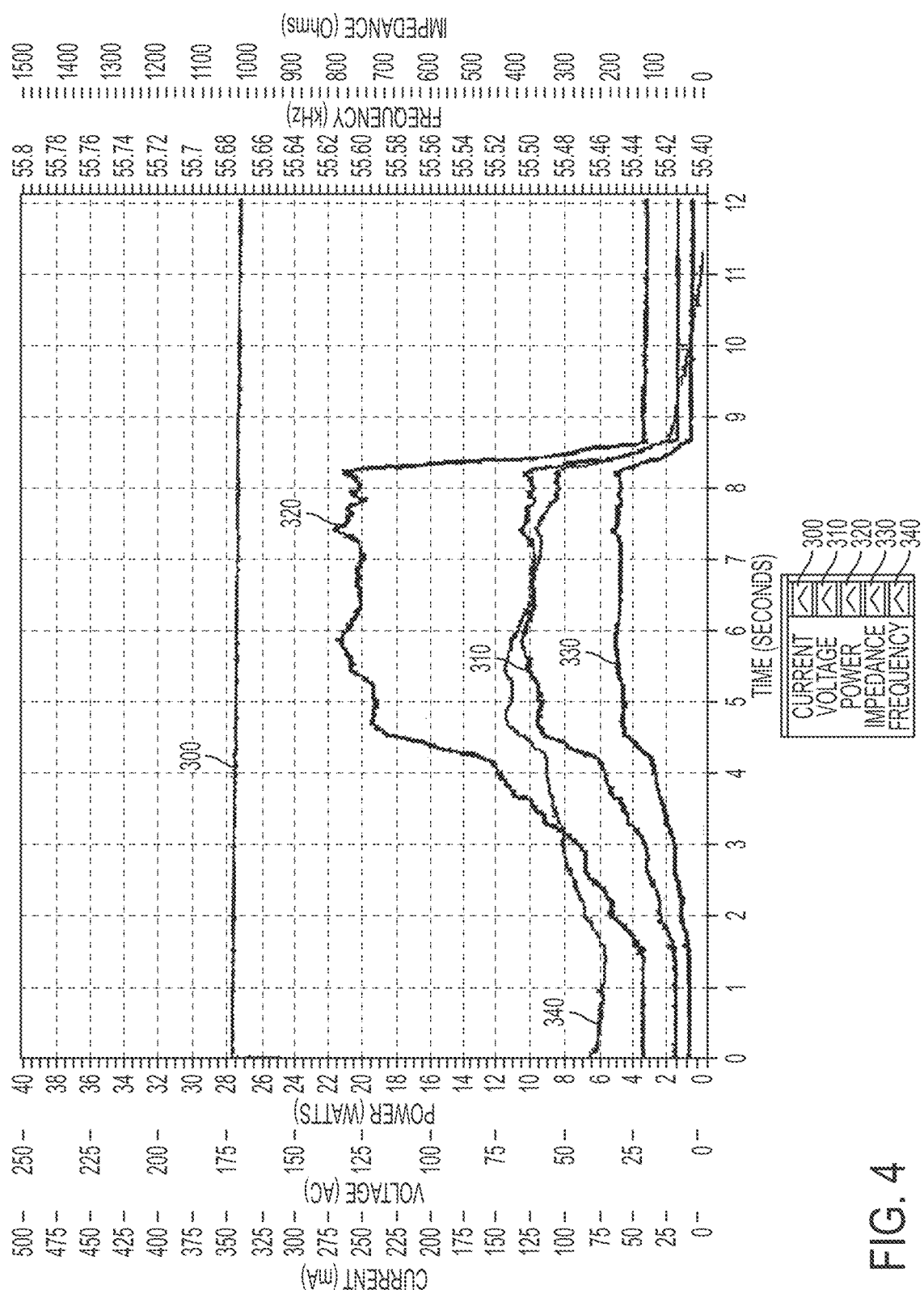
FIG. 4 is a graphical representation of current, voltage, power, impedance, and frequency waveforms of a conventional oscillator at high power and lightly loaded.

Referring to FIG. 4, in current systems a conventional oscillator is activated at time 0 resulting in current 300 rising to a desired set point of approximately 340 mA. At approximately 2 seconds a light load is applied resulting in corresponding increases to voltage 310, power 320, impedance 330, and changes in resonant frequency 340.

Figure 5:
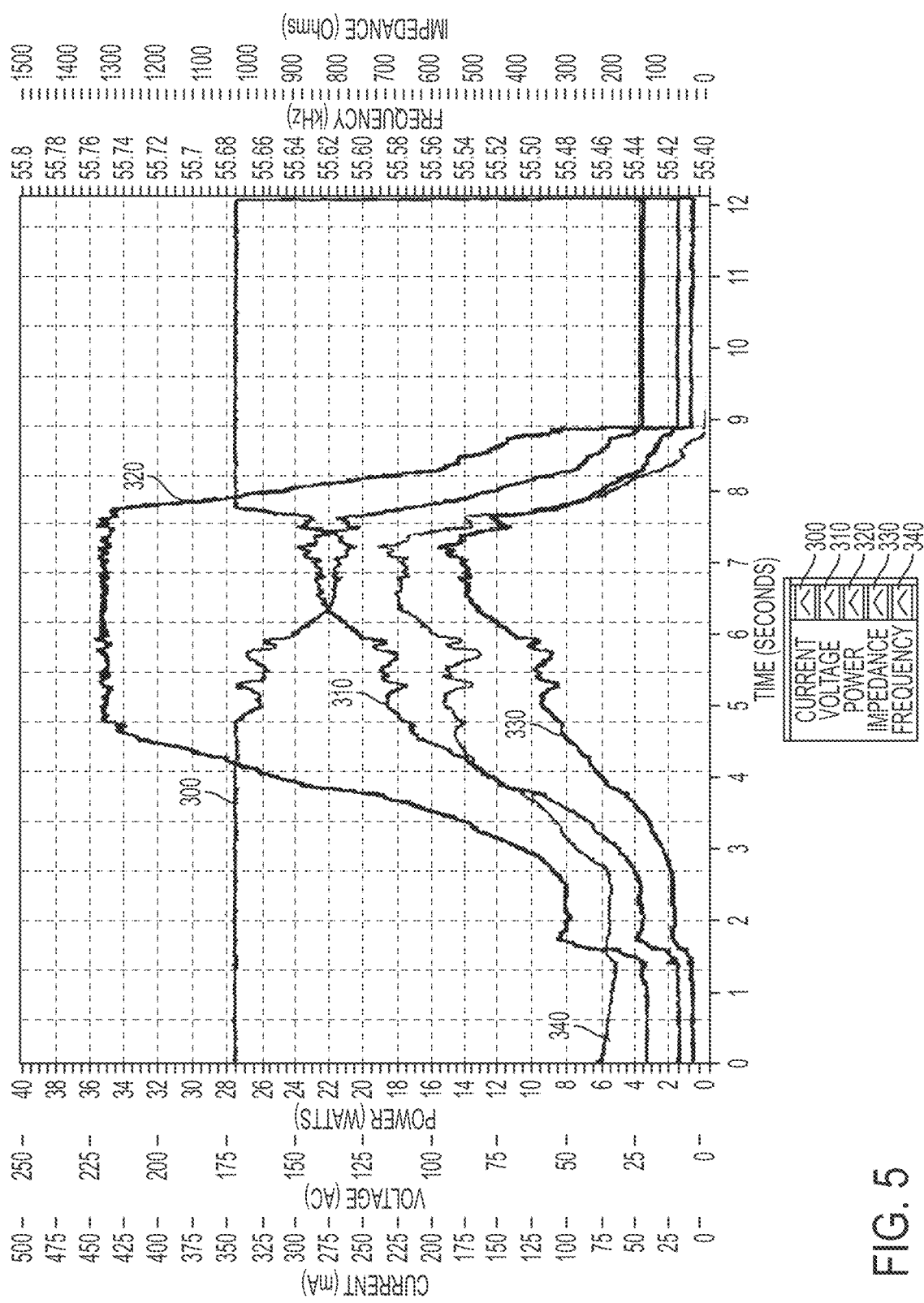
FIG. 5 is a graphical representation of current, voltage, power, impedance, and frequency waveforms of a conventional oscillator at high power and heavily loaded.

Referring to FIG. 5, in current systems a conventional oscillator is activated at time 0 resulting in the current 300 rising to a desired set point of approximately 340 mA. At approximately 2 seconds an increasing load is applied resulting in corresponding increases to the voltage 310, power 320, impedance 330, and changes in resonant frequency 340. At approximately 7 seconds, the load has increased to the point that the oscillator enters into a flat power mode where further increases in load maintain the power at 35 W as long as the oscillator stays within voltage limits of the power supply. The current 300 and therefore, displacement, varies during flat power mode. At approximately 11.5 seconds, the load is reduced to the point where the current 300 returns to the desired set point of approximately 340 mA. The voltage 310, power 320, impedance 330, and resonant frequency 340 vary with the load.

With reference now back to FIGS. 1-3, the ultrasonic surgical instrument 100 includes a multi-piece handle assembly 68 adapted to isolate the operator from the vibrations of the acoustic assembly contained within the ultrasonic transducer 50. The handle assembly 68 can be shaped to be held by a user in a conventional manner, but it is contemplated that the present ultrasonic surgical instrument 100 principally be grasped and manipulated by a trigger-like arrangement provided by a handle assembly of the instrument, as will be described. While a multi-piece handle assembly 68 is illustrated, the handle assembly 68 may comprise a single or unitary component. The proximal end of the ultrasonic surgical instrument 100 receives and is fitted to the distal end of the ultrasonic transducer 50 by insertion of the transducer 50 into the handle assembly 68. In one embodiment, the ultrasonic surgical instrument 100 may be attached to and removed from the ultrasonic transducer 50 as a unit. In other embodiments, the ultrasonic surgical instrument 100 and the ultrasonic transducer 50 may be formed as an integral unit. The ultrasonic surgical instrument 100 may include a handle assembly 68, comprising a mating housing portion 69, a housing portion 70, and a transmission assembly 71. When the present instrument is configured for endoscopic use, the construction can be dimensioned such that the transmission assembly 71 has an outside diameter of approximately 5.5 mm. The elongated transmission assembly 71 of the ultrasonic surgical instrument 100 extends orthogonally from the instrument handle assembly 68. The transmission assembly 71 can be selectively rotated with respect to the handle assembly 68 by a rotation knob 29 as further described below. The handle assembly 68 may be constructed from a durable plastic, such as polycarbonate or a liquid crystal polymer. It is also contemplated that the handle assembly 68 may alternatively be made from a variety of materials including other plastics, ceramics, or metals.

The transmission assembly 71 may include an outer tubular member or an outer sheath 72, an inner tubular actuating member 76, a waveguide 80, and an end effector 81 comprising, for example, the blade 79, a clamp arm 56, and one or more clamp pads 58. As subsequently described, the outer sheath 72, the actuating member 76, and the waveguide 80 or transmission rod may be joined together for rotation as a unit (together with the ultrasonic transducer 50) relative to the handle assembly 68. The waveguide 80, which is adapted to transmit ultrasonic energy from the ultrasonic transducer 50 to the blade 79 may be flexible, semi-flexible, or rigid. The waveguide 80 also may be configured to amplify the mechanical vibrations transmitted through the waveguide 80 to the blade 79 as is well known in the art. The waveguide 80 may further have features to control the gain of the longitudinal vibration along the waveguide 80 and features to tune the waveguide 80 to the resonant frequency of the system. In particular, the waveguide 80 may have any suitable cross-sectional dimension. For example, the waveguide 80 may have a substantially uniform cross-section or the waveguide 80 may be tapered at various sections or may be tapered along its entire length. In one expression of the current embodiment, the waveguide diameter is about 0.113 inches nominal to minimize the amount of deflection at the blade 79 so that gapping in the proximal portion of the end effector 81 is minimized.

The blade 79 may be integral with the waveguide 80 and formed as a single unit. In an alternate expression of the current embodiment, the blade 79 may be connected by a threaded connection, a welded joint, or other coupling mechanisms. The distal end of the blade 79 is disposed near an anti-node in order to tune the acoustic assembly to a preferred resonant frequency $f_o$ when the acoustic assembly is not loaded by tissue. When the ultrasonic transducer 50 is energized, the distal end of the blade 79 is configured to move longitudinally in the range of, for example, approximately 10 to 500 microns peak-to-peak, and preferably in the range of about 20 to about 200 microns at a predetermined vibration frequency $f_o$ of, for example, 55,500 Hz.

With particular reference to FIGS. 1-3, therein is illustrated one embodiment of the clamp member 60 for use with the present ultrasonic surgical instrument 100 and which is configured for cooperative action with the blade 79. The clamp member 60 in combination with the blade 79 is commonly referred to as the end effector 81, and the clamp member 60 is also commonly referred to as the jaw. The clamp member 60 includes a pivotally movable clamp arm 56, which is connected to the distal end of the outer sheath 72 and the actuating member 76, in combination with a tissue engaging pad or clamp pad 58. The clamp arm 56 is pivotally movable by a trigger 34 and the end effector 81 is rotatably movable by the rotation knob 29. In one expression of the embodiment, the clamp pad 58 is formed from TEFLON® a trademark name of E. I. Du Pont de Nemours and Company, a low coefficient of friction polymer material, or any other suitable low-friction material. The clamp pad 58 mounts on the clamp arm 56 for cooperation with the blade 79, with pivotal movement of the clamp arm 56 positioning the clamp pad 58 in substantially parallel relationship to, and in contact with, the blade 79, thereby defining a tissue treatment region. By this construction, tissue is grasped between the clamp pad 58 and the blade 79. As illustrated, the clamp pad 58 may be provided with a non-smooth surface, such as a saw tooth-like configuration to enhance the gripping of tissue in cooperation with the blade 79. The saw tooth-like configuration, or teeth, provide traction against the movement of the blade 79. The teeth also provide counter traction to the blade 79 and clamping movement. As would be appreciated by one skilled in the art, the saw tooth-like configuration is just one example of many tissue engaging surfaces to prevent movement of the tissue relative to the movement of the blade 79. Other illustrative examples include bumps, criss-cross patterns, tread patterns, a bead, or sand blasted surface.

Due to sinusoidal motion, the greatest displacement or amplitude of motion is located at the most distal portion of the blade 79, while the proximal portion of the tissue treatment region is on the order of 50% of the distal tip amplitude. During operation, the tissue in the proximal region of the end effector 81 will desiccate and thin, and the distal portion of the end effector 81 will transect tissue in that distal region, thereby allowing the desiccated and thinned tissue within the proximal region to slide distally into the more active region of the end effector 81 to complete the tissue transection.

FIG. 3 illustrates a force diagram and the relationship between the actuation force $F_A$ (provided by the actuating member 76) and transection force $F_T$ (measured at the midpoint of the optimal tissue treatment area).

$$F_T = F_A(X_2/X_1) \quad (1)$$

Where $F_A$ equals the spring preload of a proximal spring 94 (less frictional losses), which, in one embodiment, is about 12.5 pounds, and $F_T$ equals about 4.5 pounds.

$F_T$ is measured in the region of the clamp arm/blade interface where optimal tissue treatment occurs as defined by tissue marks 61a and 61b. The tissue marks 61a, b are etched or raised on the clamp arm 56 to provide a visible mark to the surgeon so the surgeon has a clear indication of the optimal tissue treatment area. The tissue marks 61a, b are about 7 mm apart in distance, and more preferably about 5 mm apart in distance.

Figure 9:
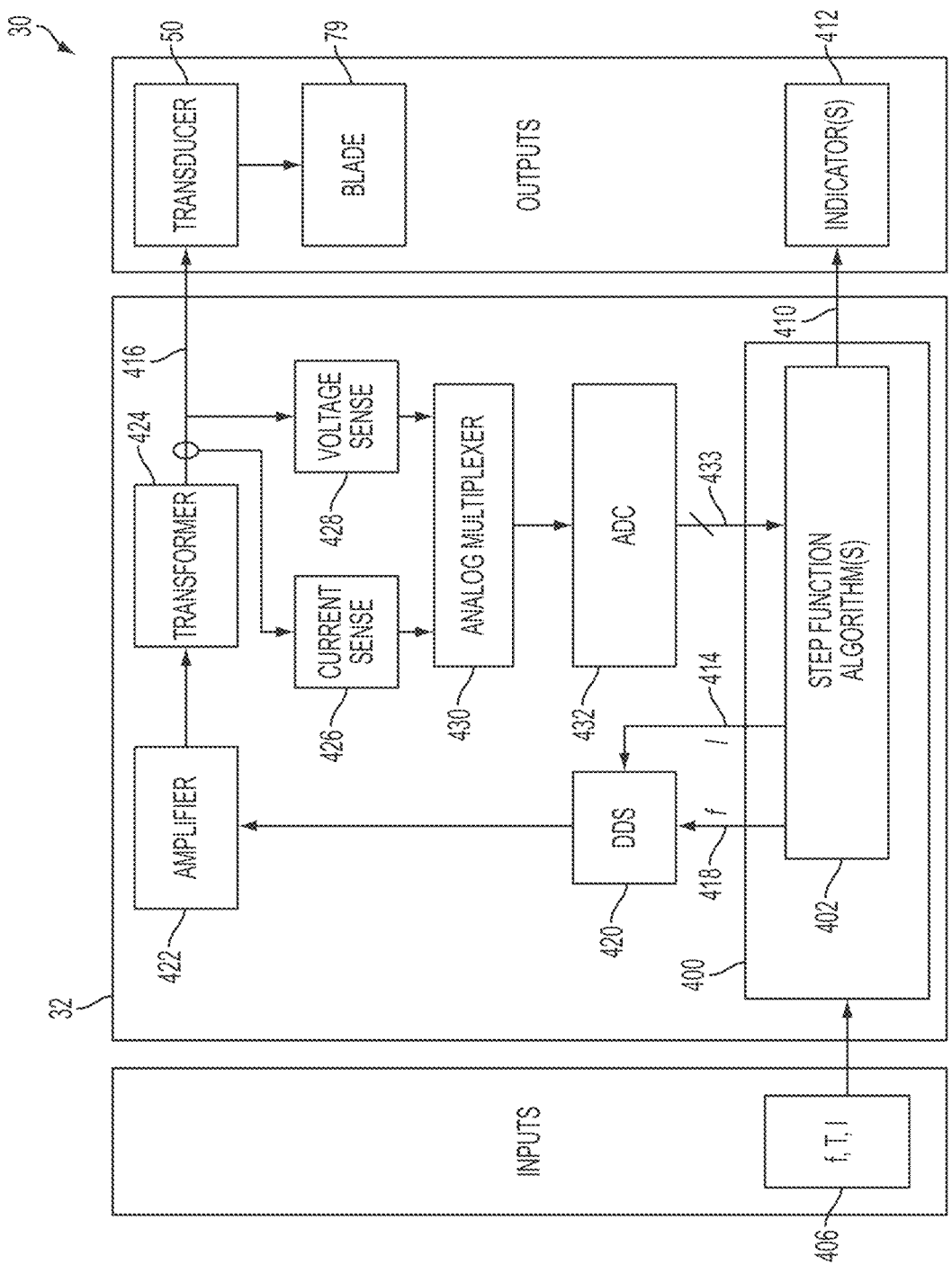
FIG. 9 illustrates one embodiment of a drive system of a generator, which creates the ultrasonic electrical signal for driving an ultrasonic transducer.

FIG. 9 illustrates one embodiment of a drive system 32 of the generator 30, which creates an ultrasonic electrical signal for driving an ultrasonic transducer. The drive system 32 is flexible and can create an ultrasonic electrical drive signal 416 at a desired frequency and power level setting for driving the ultrasonic transducer 50. In various embodiments, the generator 30 may comprise several separate functional elements, such as modules and/or blocks. Although certain modules and/or blocks may be described by way of example, it can be appreciated that a greater or lesser number of modules and/or blocks may be used and still fall within the scope of the embodiments. Further, although various embodiments may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In one embodiment, the generator 30 drive system 32 may comprise one or more embedded applications implemented as firmware, software, hardware, or any combination thereof. The generator 30 drive system 32 may comprise various executable modules such as software, programs, data, drivers, application program interfaces (APIs), and so forth. The firmware may be stored in nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In one embodiment, the generator 30 drive system 32 comprises a hardware component implemented as a processor 400 for executing program instructions for monitoring various measurable characteristics of the ultrasonic surgical instrument 100 (FIG. 1) and generating a step function output signal for driving the ultrasonic transducer 50 in cutting and/or coagulation operating modes. It will be appreciated by those skilled in the art that the generator 30 and the drive system 32 may comprise additional or fewer components and only a simplified version of the generator 30 and the drive system 32 are described herein for conciseness and clarity. In various embodiments, as previously discussed, the hardware component may be implemented as a DSP, PLD, ASIC, circuits, and/or registers. In one embodiment, the processor 400 may be configured to store and execute computer software program instructions to generate the step function output signals for driving various components of the ultrasonic surgical instrument 100, such as the transducer 50, the end effector 81, and/or the blade 79.

In one embodiment, under control of one or more software program routines, the processor 400 executes the methods in accordance with the described embodiments to generate a step function formed by a stepwise waveform of drive signals comprising current (I), voltage (V), and/or frequency (f) for various time intervals or periods (T). The stepwise waveforms of the drive signals may be generated by forming a piecewise linear combination of constant functions over a plurality of time intervals created by stepping the generator 30 drive signals, e.g., output drive current (I), voltage (V), and/or frequency (f). The time intervals or periods (T) may be predetermined (e.g., fixed and/or programmed by the user) or may be variable. Variable time intervals may be defined by setting the drive signal to a first value and maintaining the drive signal at that value until a change is detected in a monitored characteristic. Examples of monitored characteristics may comprise, for example, transducer impedance, tissue impedance, tissue heating, tissue transection, tissue coagulation, and the like. The ultrasonic drive signals generated by the generator 30 include, without limitation, ultrasonic drive signals capable of exciting the ultrasonic transducer 50 in various vibratory modes such as, for example, the primary longitudinal mode and harmonics thereof as well flexural and torsional vibratory modes.

In one embodiment, the executable modules comprise one or more step function algorithm(s) 402 stored in memory that when executed causes the processor 400 to generate a step function formed by a stepwise waveform of drive signals comprising current (I), voltage (V), and/or frequency (f) for various time intervals or periods (T). The stepwise waveforms of the drive signals may be generated by forming a piecewise linear combination of constant functions over two or more time intervals created by stepping the generator's 30 output drive current (I), voltage (V), and/or frequency (f). The drive signals may be generated either for predetermined fixed time intervals or periods (T) of time or variable time intervals or periods of time in accordance with the one or more stepped output algorithm(s) 402. Under control of the processor 400, the generator 30 steps (e.g., increment or decrement) the current (I), voltage (V), and/or frequency (f) up or down at a particular resolution for a predetermined period (T) or until a predetermined condition is detected, such as a change in a monitored characteristic (e.g., transducer impedance, tissue impedance). The steps can change in programmed increments or decrements. If other steps are desired, the generator 30 can increase or decrease the step adaptively based on measured system characteristics.

In operation, the user can program the operation of the generator 30 using the input device 406 located on the front panel of the generator 30 console. The input device 406 may comprise any suitable device that generates signals 408 that can be applied to the processor 400 to control the operation of the generator 30. In various embodiments, the input device 406 includes buttons, switches, thumbwheels, keyboard, keypad, touch screen monitor, pointing device, remote connection to a general purpose or dedicated computer. In other embodiments, the input device 406 may comprise a suitable user interface. Accordingly, by way of the input device 406, the user can set or program the current (I), voltage (V), frequency (f), and/or period (T) for programming the step function output of the generator 30. The processor 400 then displays the selected power level by sending a signal on line 410 to an output indicator 412.

In various embodiments, the output indicator 412 may provide visual, audible, and/or tactile feedback to the surgeon to indicate the status of a surgical procedure, such as, for example, when tissue cutting and coagulating is complete based on a measured characteristic of the ultrasonic surgical instrument 100, e.g., transducer impedance, tissue impedance, or other measurements as subsequently described. By way of example, and not limitation, visual feedback comprises any type of visual indication device including incandescent lamps or light emitting diodes (LEDs), graphical user interface, display, analog indicator, digital indicator, bar graph display, digital alphanumeric display. By way of example, and not limitation, audible feedback comprises any type of buzzer, computer generated tone, computerized speech, voice user interface (VUI) to interact with computers through a voice/speech platform. By way of example, and not limitation, tactile feedback comprises any type of vibratory feedback provided through the instrument housing handle assembly 68.

In one embodiment, the processor 400 may be configured or programmed to generate a digital current signal 414 and a digital frequency signal 418. These signals 414, 418 are applied to a direct digital synthesizer (DDS) circuit 420 to adjust the amplitude and the frequency (f) of the current output signal 416 to the transducer 50. The output of the DDS circuit 420 is applied to an amplifier 422 whose output is applied to a transformer 424. The output of the transformer 424 is the signal 416 applied to the ultrasonic transducer 50, which is coupled to the blade 79 by way of the waveguide 80 (FIG. 2).

In one embodiment, the generator 30 comprises one or more measurement modules or components that may be configured to monitor measurable characteristics of the ultrasonic instrument 100 (FIG. 1). In the illustrated embodiment, the processor 400 may be employed to monitor and calculate system characteristics. As shown, the processor 400 measures the impedance Z of the transducer 50 by monitoring the current supplied to the transducer 50 and the voltage applied to the transducer 50. In one embodiment, a current sense circuit 426 is employed to sense the current flowing through the transducer 50 and a voltage sense circuit 428 is employed to sense the output voltage applied to the transducer 50. These signals may be applied to the analog-to-digital converter 432 (ADC) via an analog multiplexer 430 circuit or switching circuit arrangement. The analog multiplexer 430 routes the appropriate analog signal to the ADC 432 for conversion. In other embodiments, multiple ADCs 432 may be employed for each measured characteristic instead of the multiplexer 430 circuit. The processor 400 receives the digital output 433 of the ADC 432 and calculates the transducer impedance Z based on the measured values of current and voltage. The processor 400 adjusts the output drive signal 416 such that it can generate a desired power versus load curve. In accordance with programmed step function algorithms 402, the processor 400 can step the drive signal 416, e.g., the current or frequency, in any suitable increment or decrement in response to the transducer impedance Z.

To actually cause the surgical blade 79 to vibrate, e.g., actuate the blade 79, the user activates the foot switch 434 (FIG. 1) or the switch 312*a* (FIG. 1) on the handle assembly 68. This activation outputs the drive signal 416 to the transducer 50 based on programmed values of current (I), frequency (f), and corresponding time periods (T). After a predetermined fixed time period (T), or variable time period based on a measurable system characteristic such as changes in the impedance Z of the transducer 50, the processor 400 changes the output current step or frequency step in accordance with the programmed values. The output indicator 412 communicates the particular state of the process to the user.

Figure 6:
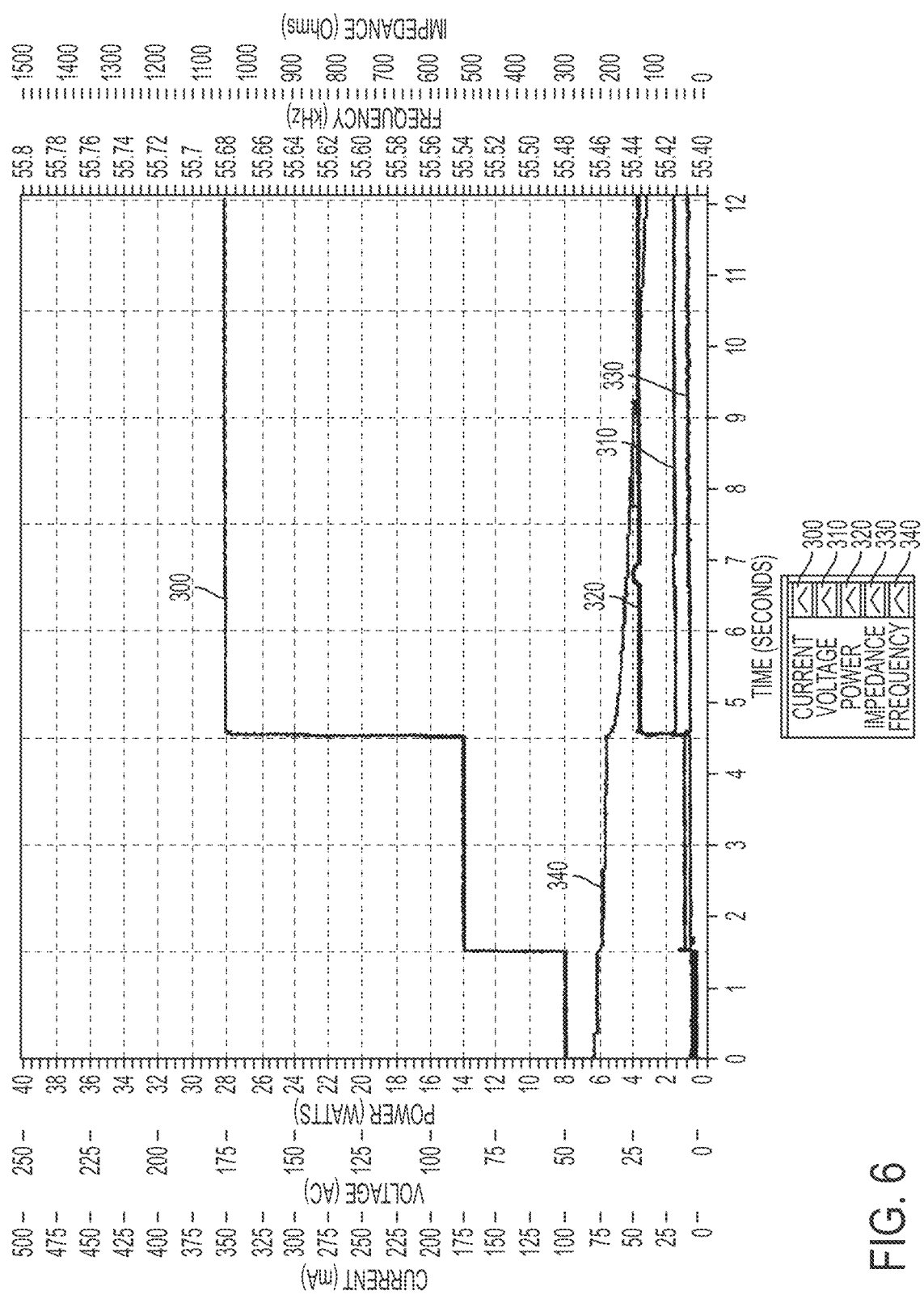
FIG. 6 is a graphical representation of a current step function waveform and voltage, power, impedance, and frequency waveforms of one embodiment of an oscillator and unloaded.

The programmed operation of the generator 30 can be further illustrated with reference to FIGS. 6, 7, and 8, where graphical representations of current 300, voltage 310, power 320, impedance 330, and frequency 340 are shown for the generator 30 in an unloaded state, a lightly loaded state, and a heavily loaded state, respectively. FIG. 6 is a graphical representation of current 300, voltage 310, power 320, impedance 330, and frequency 340 waveforms of one embodiment of the generator 30 in an unloaded state. In the illustrated embodiment, the current 300 output of the generator 30 is stepped. As shown in FIG. 6, the generator 30 is initially activated at about time 0 resulting in the current 300 rising to a first set point $I_1$ of about 100 mA. The current 300 is maintained at the first set point $I_1$, for a first period $T_1$. At the end of the first period $T_1$, e.g., about 1 second in the illustrated embodiment, the current 300 set point $I_1$ is changed, e.g., stepped, by the generator 30 in accordance with the software, e.g., the step function algorithm(s) 402, to a second set point $I_2$ of about 175 mA for a second period $T_2$, e.g., about 2 seconds in the illustrated embodiment. At the end of the second period $T_2$, e.g., at about 3 seconds in the illustrated embodiment, the generator 30 software changes the current 300 to a third set point $I_3$ of about 350 mA. The voltage 310, current 300, power 320, and frequency respond only slightly because there is no load on the system.

Figure 7:
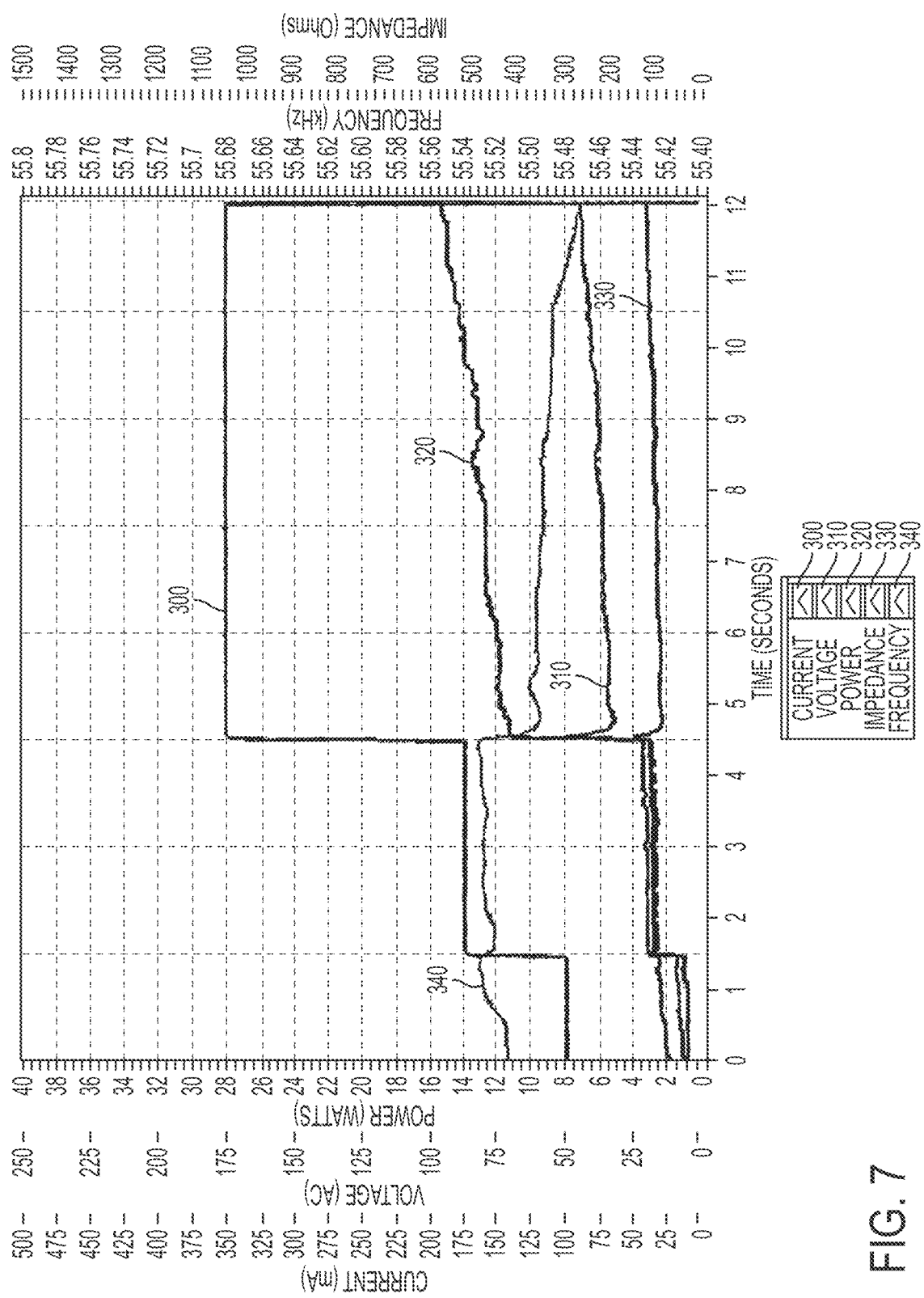
FIG. 7 is a graphical representation of a current step function waveform and voltage, power, impedance, and frequency waveforms of one embodiment of an oscillator and lightly loaded.

FIG. 7 is a graphical representation of the current 300, voltage 310, power 320, impedance 330, and frequency 340 waveforms of one embodiment of the generator 30 under a lightly loaded state. Referring to FIG. 7, the generator 30 is activated at about time 0 resulting in the current 300 rising to the first current 300 set point $I_1$ of about 100 mA. At about 1 second the current 300 set point is changed within the generator 30 by the software to $I_2$ of about 175 mA, and then again at about 3 seconds the generator 30 changes the current 300 set point to $I_3$ of about 350 mA. The voltage 310, current 300, power 320, and frequency 340 are shown responding to the light load similar to that shown in FIG. 4.

Figure 8:
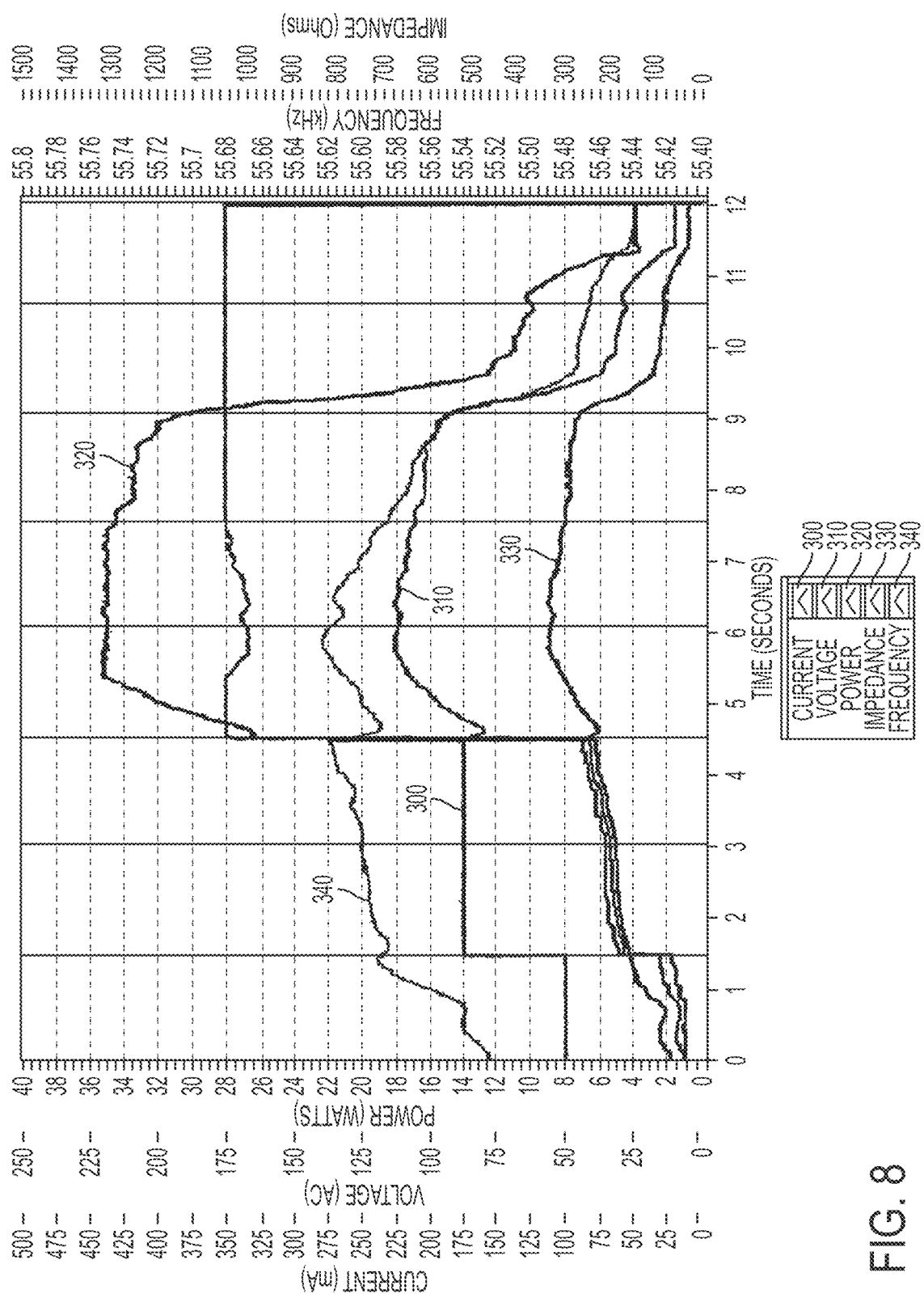
FIG. 8 is a graphical representation of a current step function waveform and voltage, power, impedance, and frequency waveforms of one embodiment of an oscillator and heavily loaded.

FIG. 8 is a graphical representation of the current 300, voltage 310, power 320, impedance 330, and frequency 340 waveforms of one embodiment of the generator 30 under a heavily loaded state. Referring to FIG. 8, the generator 30 is activated at about time 0 resulting in the current 300 rising to the first set point $I_1$ of about 100 mA. At about 1 second the current 300 set point is changed within the generator 30 by the software to $I_2$ of about 175 mA, and then again at about 3 seconds the generator 30 changes the current 300 set point to $I_3$ of about 350 mA. The voltage 310, current 300, power 320, and frequency 340 are shown responding to the heavy load similar to that shown in FIG. 5.

It will be appreciated by those skilled in the art that the current 300 step function set points (e.g., $I_1$, $I_2$, $I_3$) and the time intervals or periods (e.g., $T_1$, $T_2$) of duration for each of the step function set points described in FIGS. 6-8 are not limited to the values described herein and may be adjusted to any suitable value as may be desired for a given set of surgical procedures. Additional or fewer current set points and periods of duration may be selected as may be desired for a given set of design characteristics or performance constraints. As previously discussed, the periods may be predetermined by programming or may be variable based on measurable system characteristics. The embodiments are not limited in this context.

Having described operational details of various embodiments of the surgical system 19, operations for the above surgical system 19 may be further described in terms of a process for cutting and coagulating a blood vessel employing a surgical instrument comprising the input device 406 and the transducer impedance measurement capabilities described with reference to FIG. 9. Although a particular process is described in connection with the operational details, it can be appreciated that the process merely provides an example of how the general functionality described herein can be implemented by the surgical system 19. Further, the given process does not necessarily have to be executed in the order presented herein unless otherwise indicated. As previously discussed, the input device 406 may be employed to program the stepped output (e.g., current, voltage, frequency) to the ultrasonic transducer 50/blade 79 assembly.

Accordingly, with reference now to FIGS. 1-3 and 6-9, one technique for sealing a vessel includes separating and moving the inner muscle layer of the vessel away from the adventitia layer prior to the application of standard ultrasonic energy to transect and seal the vessel. Although conventional methods have achieved this separation by increasing the force applied to the clamp member 60, disclosed is an alternative apparatus and method for cutting and coagulating tissue without relying on clamp force alone. In order to more effectively separate the tissue layers of a vessel, for example, the generator 30 may be programmed to apply a frequency step function to the ultrasonic transducer 50 to mechanically displace the blade 79 in multiple modes in accordance with the step function. In one embodiment, the frequency step function may be programmed by way of the user interface 406, wherein the user can select a stepped-frequency program, the frequency (f) for each step, and the corresponding time period (T) of duration for each step for which the ultrasonic transducer 50 will be excited. The user may program a complete operational cycle by setting multiple frequencies for multiple periods to perform various surgical procedures.

In one embodiment, a first ultrasonic frequency may be set initially to mechanically separate the muscle tissue layer of a vessel prior to applying a second ultrasonic frequency to cut and seal the vessel. By way of example, and not limitation, in accordance with one implementation of the program, initially, the generator 30 is programmed to output a first drive frequency $f_1$ for a first period $T_1$ of time (for example less than approximately 1 second), wherein the first frequency $f_1$ is significantly off resonance, for example, $f_o/2$, $2f_o$ or other structural resonant frequencies, where $f_o$ is the resonant frequency (e.g., 55.5 kHz). The first frequency $f_1$ provides a low level of mechanical vibration action to the blade 79 that, in conjunction with the clamp force, mechanically separates the muscle tissue layer (subtherapeutic) of the vessel without causing significant heating that generally occurs at resonance. After the first period $T_1$, the generator 30 is programmed to automatically switch the drive frequency to the resonant frequency $f_o$ for a second period $T_2$ to transect and seal the vessel. The duration of the second period $T_2$ may be programmed or may be determined by the length of time it actually takes to cut and seal the vessel as determined by the user or may be based on measured system characteristics such as the transducer impedance Z as described in more detail below.

In one embodiment, the tissue/vessel transection process (e.g., separating the muscle layer of the vessel from the adventitia layer and transecting/sealing the vessel) may be automated by sensing the impedance Z characteristics of the transducer 50 to detect when the transection of the tissue/vessel occurs. The impedance Z can be correlated to the transection of the muscle layer and to the transection/sealing of the vessel to provide a trigger for the processor 400 to generate the frequency and/or current step function output. As previously discussed with reference to FIG. 9, the impedance Z of the transducer 50 may be calculated by the processor 400 based on the current flowing through transducer 50 and the voltage applied to the transducer 50 while the blade 79 is under various loads. Because the impedance Z of the transducer 50 is proportional to the load applied to the blade 79, as the load on the blade 79 increases, the impedance Z of the transducer 50 increases, and as the load on the blade 79 decreases the impedance Z of the transducer 50 decreases. Accordingly, the impedance Z of the transducer 50 can be monitored to detect the transection of the inner muscle tissue layer of the vessel from the adventitia layer and can also be monitored to detect when the vessel has been transected and sealed.

In one embodiment, the ultrasonic surgical instrument 110 may be operated in accordance with a programmed step function algorithm responsive to the transducer impedance Z. In one embodiment, a frequency step function output may be initiated based on a comparison of the transducer impedance Z and one or more predetermined thresholds that have been correlated with tissue loads against the blade 79. When the transducer impedance Z transitions above or below (e.g., crosses) a threshold, the processor 400 applies a digital frequency signal 418 to the DDS circuit 420 to change the frequency of the drive signal 416 by a predetermined step in accordance with the step function algorithm(s) 402 responsive to the transducer impedance Z. In operation, the blade 79 is first located at the tissue treatment site. The processor 400 applies a first digital frequency signal 418 to set a first drive frequency f1 that is off resonance (e.g., $f_o/2$, $2f_o$ or other structural resonant frequencies, where $f_0$ is the resonant frequency). The drive signal 416 is applied to the transducer 50 in response to activation of the switch 312a on the handle assembly 68 or the foot switch 434. During this period the ultrasonic transducer 50 mechanically activates the blade 79 at the first drive frequency $f_1$. A force or load may be applied to the clamp member 60 and the blade 79 to facilitate this process. During this period, the processor 400 monitors the transducer impedance Z until the load on the blade 79 changes and the transducer impedance Z crosses a predetermined threshold to indicate that the tissue layer has been transected. The processor 400 then applies a second digital frequency signal 418 to set a second drive frequency $f_2$, e.g., the resonant frequency $f_o$ or other suitable frequency for transecting, coagulating, and sealing tissue. Another portion of the tissue (e.g., the vessel) is then grasped between the clamp member 60 and the blade 79. The transducer 50 is now energized by the drive signal 416 at the second drive frequency $f_2$ by actuating either the foot switch 434 or the switch 312a on the handle assembly 68. It will be appreciated by those skilled in the art that the drive current (I) output also may be stepped as described with reference to FIGS. 6-8 based on the transducer impedance Z.

According to one step function algorithm 402, the processor 400 initially sets a first drive frequency $f_1$ that is significantly off resonance to separate the inner muscle layer of the vessel from the adventitia layer. During this period of operation the processor 400 monitors the transducer impedance Z to determine when the inner muscle layer is transected or separated from the adventitia layer. Because the transducer impedance Z is correlated to the load applied to the blade 79, for example, cutting more tissue decrease the load on the blade 79 and the transducer impedance Z. The transection of the inner muscle layer is detected when the transducer impedance Z drops below a predetermined threshold. When the change in transducer impedance Z indicates that the vessel has been separated from the inner muscle layer, the processor 400 sets the drive frequency to the resonant frequency $f_o$. The vessel is then grasped between the blade 79 and the clamp member 60 and the transducer 50 is activated by actuating either the foot switch or the switch on the handle assembly 68 to transect and seal the vessel. In one embodiment, the impedance Z change may range between about 1.5 to about 4 times a base impedance measurements from an initial point of contact with the tissue to a point just before the muscle layer is transected and sealed.

Figure 10:
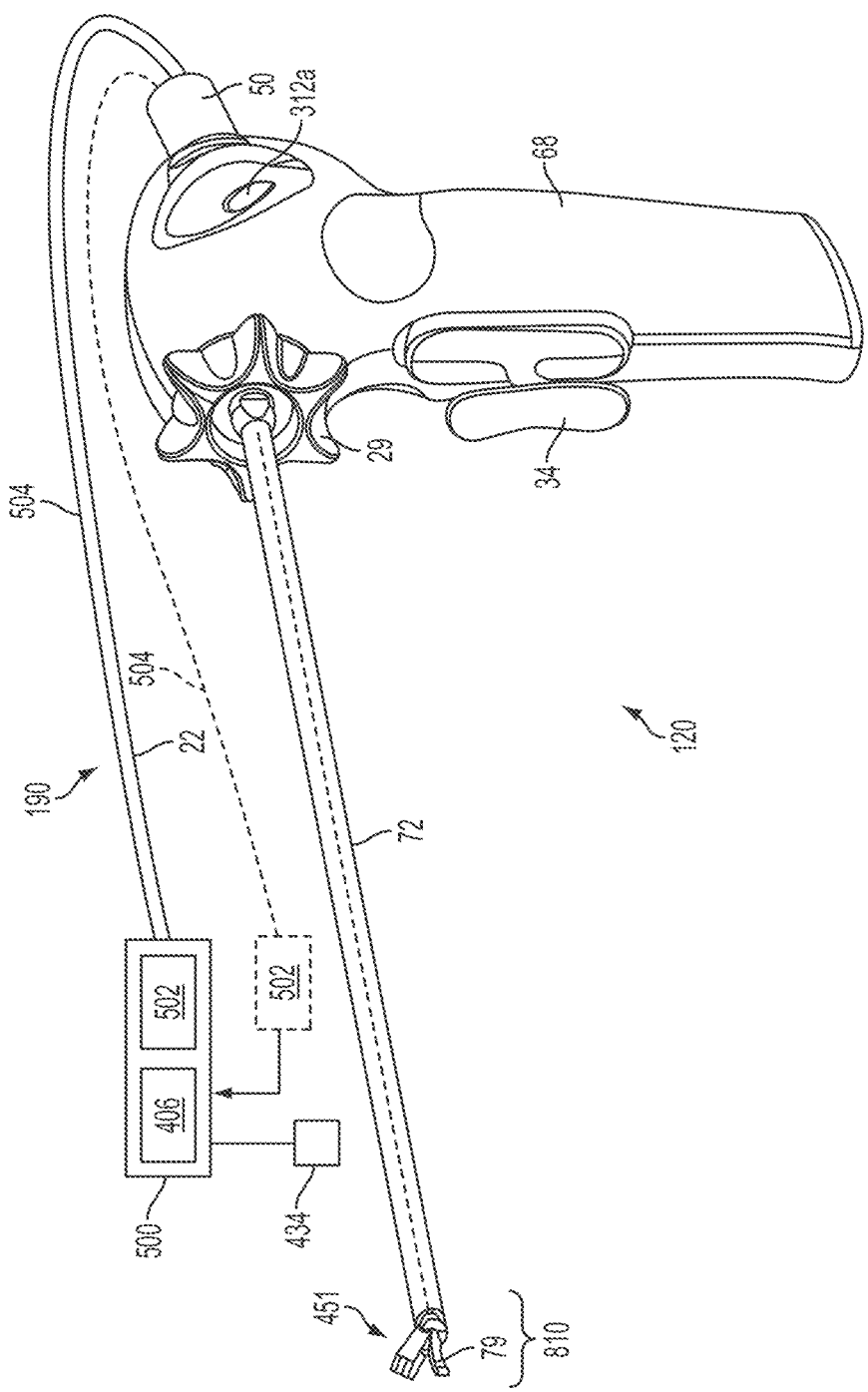
FIG. 10 illustrates one embodiment of a surgical system comprising an ultrasonic surgical instrument and a generator comprising a tissue impedance module.

FIG. 10 illustrates one embodiment of a surgical system 190 comprising an ultrasonic surgical instrument 120 and a generator 500 comprising a tissue impedance module 502. Although in the presently disclosed embodiment, the generator 500 is shown separate from the surgical instrument 120, in one embodiment, the generator 500 may be formed integrally with the surgical instrument 120 to form a unitary surgical system 190. In one embodiment, the generator 500 may be configured to monitor the electrical impedance of the tissue $Z_t$ and to control the characteristics of time and power level based on the tissue impedance $Z_t$. In one embodiment, the tissue impedance $Z_t$ may be determined by applying a subtherapeutic radio frequency (RF) signal to the tissue and measuring the current through the tissue by way of a return electrode on the clamp member 60. In the embodiment illustrated in FIG. 10, an end effector 810 portion of the surgical system 190 comprises a clamp arm assembly 451 connected to the distal end of the outer sheath 72. The blade 79 forms a first (e.g., energizing) electrode and the clamp arm assembly 451 comprises an electrically conductive portion that forms a second (e.g., return) electrode. The tissue impedance module 502 is coupled to the blade 79 and the clamp arm assembly 451 through a suitable transmission medium such as a cable 504. The cable 504 comprises multiple electrical conductors for applying a voltage to the tissue and providing a return path for current flowing through the tissue back to the impedance module 502. In various embodiments, the tissue impedance module 502 may be formed integrally with the generator 500 or may be provided as a separate circuit coupled to the generator 500 (shown in phantom to illustrate this option). The generator 500 is substantially similar to the generator 30 with the added feature of the tissue impedance module 502.

Figure 11:
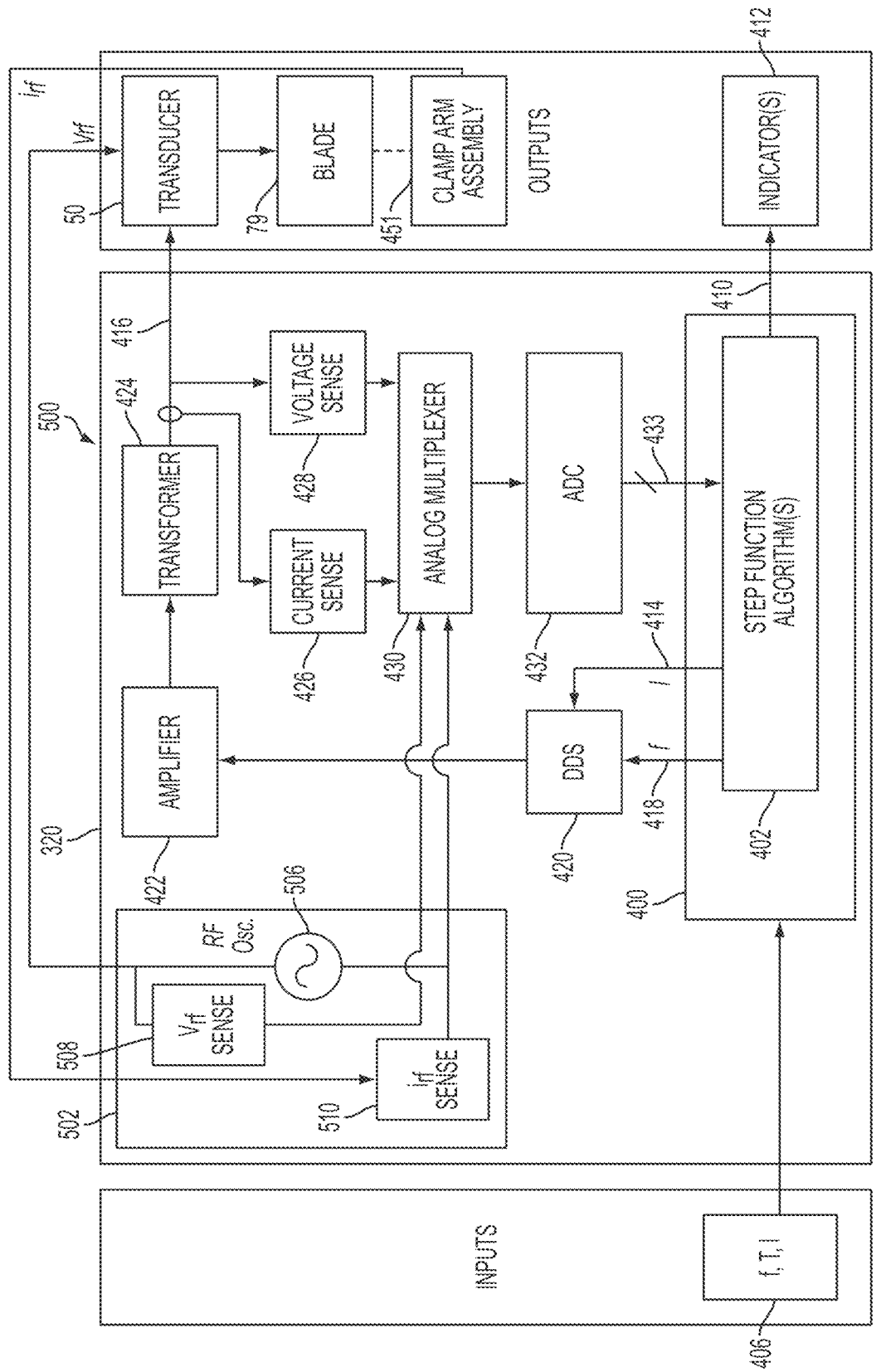
FIG. 11 illustrates one embodiment of a drive system of a generator comprising a tissue impedance module.

FIG. 11 illustrates one embodiment of a drive system 321 of the generator 500 comprising the tissue impedance module 502. The drive system 321 generates the ultrasonic electrical drive signal 416 to drive the ultrasonic transducer 50. In one embodiment, the tissue impedance module 502 may be configured to measure the impedance $Z_t$ of tissue grasped between the blade 79 and the clamp arm assembly 451. The tissue impedance module 502 comprises an RF oscillator 506, a voltage sensing circuit 508, and a current sensing circuit 510. The voltage and current sensing circuits 508, 510 respond to the RF voltage $v_{rf}$ applied to the blade 79 electrode and the RF current $i_{rf}$ flowing through the blade 79 electrode, the tissue, and the conductive portion of the clamp arm assembly 451. The sensed voltage $v_{rf}$ and current $i_{rf}$ are converted to digital form by the ADC 432 via the analog multiplexer 430. The processor 400 receives the digitized output 433 of the ADC 432 and determines the tissue impedance $Z_t$ by calculating the ratio of the RF voltage $v_{rf}$ to current $i_{rf}$ measured by the voltage sense circuit 508 and the current sense circuit 510. In one embodiment, the transection of the inner muscle layer and the tissue may be detected by sensing the tissue impedance $Z_t$. Accordingly, detection of the tissue impedance $Z_t$ may be integrated with an automated process for separating the inner muscle layer from the outer adventitia layer prior to transecting the tissue without causing a significant amount of heating, which normally occurs at resonance.

Figure 12:
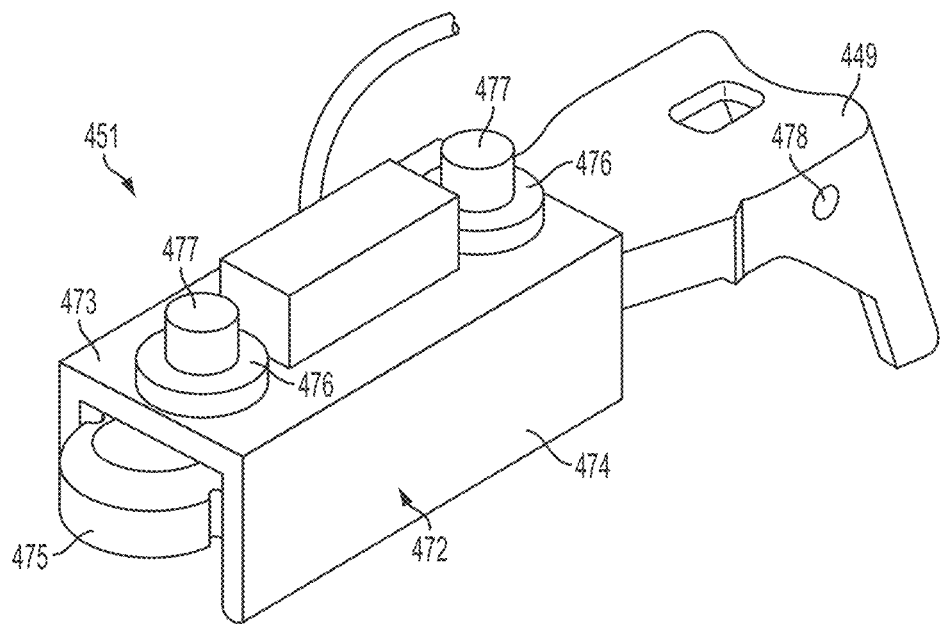
FIG. 12 illustrates one embodiment of a clamp arm assembly that may be employed with a surgical system.

FIG. 12 illustrates one embodiment of the clamp arm assembly 451 that may be employed with the surgical system 190 (FIG. 10). In the illustrated embodiment, the clamp arm assembly 451 comprises a conductive jacket 472 mounted to a base 449. The conductive jacket 472 is the electrically conductive portion of the clamp arm assembly 451 that forms the second, e.g., return, electrode. In one implementation, the clamp arm 56 (FIG. 3) may form the base 449 on which the conductive jacket 472 is mounted. In various embodiments, the conductive jacket 472 may comprise a center portion 473 and at least one downwardly-extending sidewall 474 which can extend below the bottom surface 475 of the base 449. In the illustrated embodiment, the conductive jacket 472 has two sidewalls 474 extending downwardly on opposite sides of the base 449. In other embodiments, the center portion 473 may comprise at least one aperture 476 which can be configured to receive a projection 477 extending from the base 449. In such embodiments, the projections 477 can be press-fit within the apertures 476 in order to secure the conductive jacket 472 to the base 449. In other embodiments, the projections 477 can be deformed after they are inserted into the apertures 476. In various embodiments, fasteners can be used to secure the conductive jacket 472 to the base 449.

In various embodiments, the clamp arm assembly 451 may comprise a non-electrically conductive or insulative material, such as plastic and/or rubber, for example, positioned intermediate the conductive jacket 472 and the base 449. The electrically insulative material can prevent current from flowing, or shorting, between the conductive jacket 472 and the base 449. In various embodiments, the base 449 may comprise at least one aperture 478, which can be configured to receive a pivot pin (not illustrated). The pivot pin can be configured to pivotably mount the base 449 to the sheath 72 (FIG. 10), for example, such that the clamp arm assembly 451 can be rotated between open and closed positions relative to the sheath 72. In the illustrated embodiment, the base 449 includes two apertures 478 positioned on opposite sides of the base 449. In one embodiment, a pivot pin may be formed of or may comprise a non-electrically conductive or insulative material, such as plastic and/or rubber, for example, which can be configured to prevent current from flowing into the sheath 72 even if the base 449 is in electrical contact with the conductive jacket 472, for example. Additional clamp arm assemblies comprising various embodiments of electrodes may be employed. Examples of such clamp arm assemblies are described in commonly-owned and contemporaneously-filed U.S. patent application Ser. Nos. 12/503,769, 12/503,770, and 12/503,766, each of which is incorporated herein by reference in its entirety.

Figure 13:
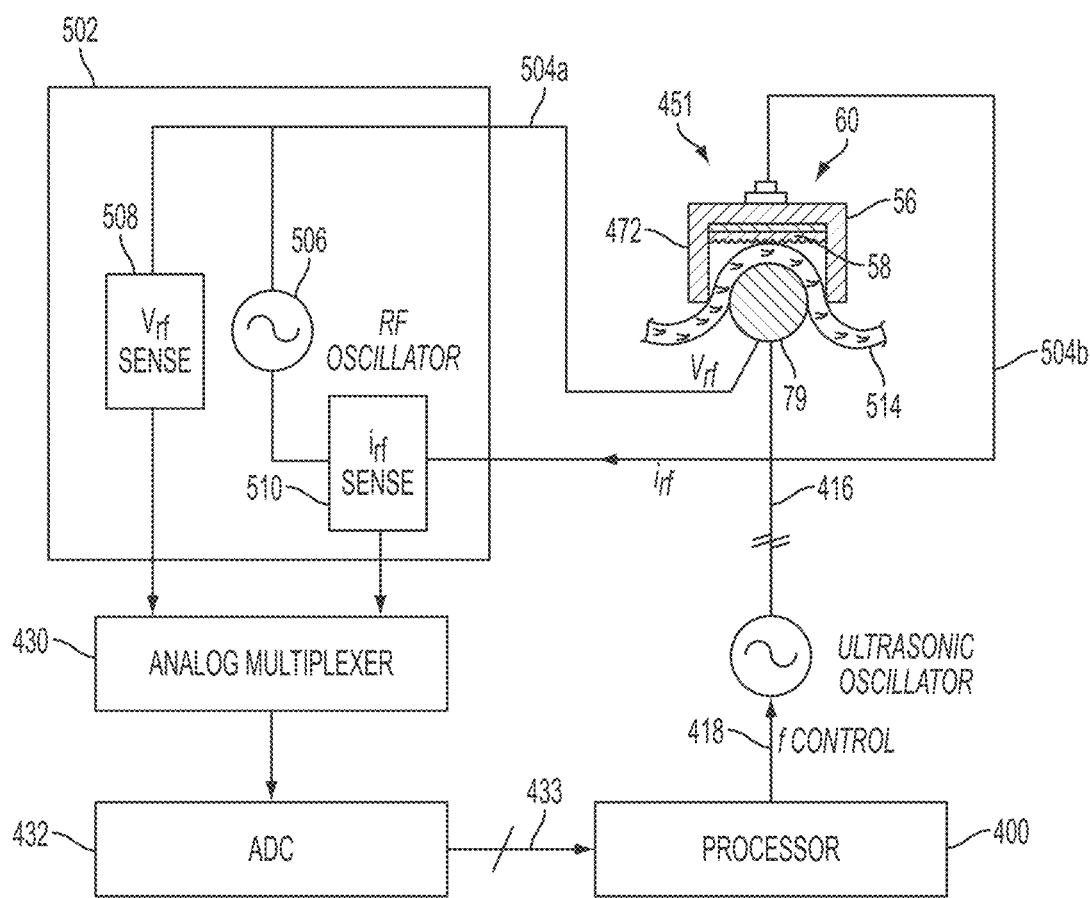
FIG. 13 is a schematic diagram of a tissue impedance module coupled to a blade and a clamp arm assembly with tissue located therebetween.

FIG. 13 is a schematic diagram of the tissue impedance module 502 coupled to the blade 79 and the clamp arm assembly 415 with tissue 514 located therebetween. With reference now to FIGS. 10-13, the generator 500 comprises the tissue impedance module 502 configured for monitoring the impedance of the tissue 514 ($Z_t$) located between the blade 79 and the clamp arm assembly 451 during the tissue transection process. The tissue impedance module 502 is coupled to the ultrasonic surgical instrument 120 by way of the cable 504. The cable 504 includes a first "energizing" conductor 504a connected to the blade 79 (e.g., positive [+] electrode) and a second "return" conductor 504b connected to the conductive jacket 472 (e.g., negative [−] electrode) of the clamp arm assembly 451. In one embodiment, RF voltage $v_{rf}$ is applied to the blade 79 to cause RF current $i_f$ to flow through the tissue 514. The second conductor 504b provides the return path for the current $i_f$ back to the tissue impedance module 502. The distal end of the return conductor 504b is connected to the conductive jacket 472 such that the current $i_{rf}$ can flow from the blade 79, through the tissue 514 positioned intermediate the conductive jacket 472 and the blade 79, and the conductive jacket 472 to the return conductor 504b. The impedance module 502 connects in circuit, by way of the first and second conductors 504a, b. In one embodiment, the RF energy may be applied to the blade 79 through the ultrasonic transducer 50 and the waveguide 80 (FIG. 2). It is worthwhile noting that the RF energy applied to the tissue 514 for purposes of measuring the tissue impedance $Z_t$ is a low level subtherapeutic signal that does not contribute in a significant manner, or at all, to the treatment of the tissue 514.

Having described operational details of various embodiments of the surgical system 190, operations for the above surgical system 190 may be further described with reference to FIGS. 10-13 in terms of a process for cutting and coagulating a blood vessel employing a surgical instrument comprising the input device 406 and the tissue impedance module 502. Although a particular process is described in connection with the operational details, it can be appreciated that the process merely provides an example of how the general functionality described herein can be implemented by the surgical system 190. Further, the given process does not necessarily have to be executed in the order presented herein unless otherwise indicated. As previously discussed, the input device 406 may be employed to program the step function output (e.g., current, voltage, frequency) to the ultrasonic transducer 50/blade 79 assembly.

In one embodiment, a first conductor or wire may be connected to the outer sheath 72 of the instrument 120 and a second conductor or wire may be connected to the blade 79/transducer 50. By nature of the design, the blade 79 and the transducer 50 are electrically isolated from the outer sheath 72 as well as other elements of the actuation mechanism for the instrument 120 including the base 449 and the inner sheath 76. The outer sheath 79 and other elements of the actuation mechanism including the base 449 and the inner sheath 76 are all electrically continuous with one another—that is, they are all metallic and touch one another. Accordingly, by connecting a first conductor to the outer sheath 72 and connecting a second conductor to the blade 79 or the transducer 50 such that the tissue resides between these two conductive pathways, the system can monitor the electrical impedance of the tissue as long as the tissue contacts both the blade 79 and the base 449. To facilitate this contact, the base 449 itself may include outwardly and possibly downwardly protruding features to assure tissue contact while, effectively integrating conductive jacket 472 into base 449.

In one embodiment, the ultrasonic surgical instrument 120 may be operated in accordance with a programmed step function algorithm 402 responsive to the tissue impedance $Z_t$. In one embodiment, a frequency step function output may be initiated based on a comparison of the tissue impedance $Z_t$ and predetermined thresholds that have been correlated with various tissue states (e.g., desiccation, transection, sealing). When the tissue impedance $Z_t$ transitions above or below (e.g., crosses) a threshold, the processor 400 applies a digital frequency signal 418 to the DDS circuit 420 to change the frequency of an ultrasonic oscillator by a predetermined step in accordance with the step function algorithm 402 responsive to the tissue impedance $Z_t$.

In operation, the blade 79 is located at the tissue treatment site. The tissue 514 is grasped between the blade 79 and the clamp arm assembly 451 such that the blade 79 and the conductive jacket 472 make electrical contact with the tissue 514. The processor 400 applies a first digital frequency signal 418 to set a first drive frequency $f_1$ that is off resonance (e.g., $f_o/2$, $2f_o$ or other structural resonant frequencies, where $f_o$ is the resonant frequency). The blade 79 is electrically energized by the low level subtherapeutic RF voltage $v_{rf}$ supplied by the tissue impedance module 502. The drive signal 416 is applied to the transducer 50/blade 79 in response to actuation of the switch 312a on the handle assembly 68 or the foot switch 434 until the tissue impedance $Z_t$ changes by a predetermined amount. A force or load is then applied to the clamp arm assembly 451 and the blade 79. During this period the ultrasonic transducer 50 mechanically activates the blade 79 at the first drive frequency $f_1$ and as a result, the tissue 514 begins to desiccate from the ultrasonic action applied between the blade 79 and the one or more clamp pads 58 of the clamp arm assembly 451 causing the tissue impedance $Z_t$ to increase. Eventually, as the tissue is transected by the ultrasonic action and applied clamp force, the tissue impedance $Z_t$ becomes very high or infinite as the tissue fully transects such that no conductive path exists between the blade 79 and the conductive jacket 472. It will be appreciated by those skilled in the art that the drive current (I) output also may be stepped as described with reference to FIGS. 6-8 based on the tissue impedance $Z_t$.

In one embodiment, the tissue impedance $Z_t$ may be monitored by the impedance module 502 in accordance with the following process. A measurable RF current i1 is conveyed through the first energizing conductor 504a to the blade 79, through the tissue 514, and back to the impedance module 502 through the conductive jacket 472 and the second conductor 504b. As the tissue 514 is desiccated and cut by the ultrasonic action of the blade 79 acting against the one or more clamp pads 58, the impedance of the tissue 514 increases and thus the current i1 in the return path, i.e., the second conductor 504b, decreases. The impedance module 502 measures the tissue impedance $Z_t$ and conveys a representative signal to the ADC 432 whose digital output 433 is provided to the processor 400. The processor 400 calculates the tissue impedance $Z_t$ based on these measured values of $v_{rf}$ and $i_{rf}$. The processor 400 steps the frequency by any suitable increment or decrement in response to changes in tissue impedance $Z_t$. The processor 400 controls the drive signals 416 and can make any necessary adjustments in amplitude and frequency in response to the tissue impedance $Z_t$. In one embodiment, the processor 400 can cut off the drive signal 416 when the tissue impedance $Z_t$ reaches a predetermined threshold value.

Accordingly, by way of example, and not limitation, in one embodiment, the ultrasonic surgical instrument 120 may be operated in accordance with a programmed stepped output algorithm to separate the inner muscle layer of a vessel from the adventitia layer prior to transecting and sealing the vessel. As previously discussed, according to one step function algorithm, the processor 400 initially sets a first drive frequency f1 that is significantly off resonance. The transducer 50 is activated to separate the inner muscle layer of the vessel from the adventitia layer and the tissue impedance module 502 applies a subtherapeutic RF voltage $v_{rf}$ signal to the blade 79. During this period $T_1$ of operation the processor 400 monitors the tissue impedance $Z_t$ to determine when the inner muscle layer is transected or separated from the adventitia layer. The tissue impedance $Z_t$ is correlated to the load applied to the blade 79, for example, when the tissue becomes desiccated or when the tissue is transected the tissue impedance $Z_t$ becomes extremely high or infinite. The change in tissue impedance $Z_t$ indicates that the vessel has been separated or transected from the inner muscle layer and the generator 500 is deactivated for a second period of time $T_2$. The processor 400 then sets the drive frequency to the resonant frequency $f_o$. The vessel is then grasped between the blade 79 and the clamp arm assembly 451 and the transducer 50 is reactivated to transect and seal the vessel. Continuous monitoring of the tissue impedance $Z_t$ provides an indication of when the vessel is transected and sealed. Also, the tissue impedance $Z_t$ may be monitored to provide an indication of the completeness of the tissue cutting and/or coagulating process or to stop the activation of the ultrasonic generator 500 when the tissue impedance $Z_t$ reaches a predetermined threshold value. The threshold for the tissue impedance $Z_t$ may be selected, for example, to indicate that the vessel has been transected. In one embodiment, the tissue impedance $Z_t$ may range between about 10 Ohms to about 1000 Ohms from an initial point to a point just before the muscle layer is transected and sealed.

The applicants have discovered that experiments that run varying current set points (both increasing and decreasing) and dwell times indicate that the described embodiments can be used to separate the inner muscle layer from the outer adventitia layer prior to completing the transection resulting in improved hemostasis and potentially lower total energy (heat) at the transection site. Furthermore, although the surgical instruments 100, 120 have been described in regards to impedance threshold detection schemes to determine when the muscle layer is separated from the adventitia, other embodiments that do not employ any detection scheme are within the scope of the present disclosure. For example, embodiments of the surgical instruments 100, 120 may be employed in simplified surgical systems wherein non-resonant power is applied to separate the layers for a predetermined time of approximately 1 second or less, prior to applying a resonant power to cut the tissue. The embodiments are not limited in this context.

Having described operational details of various embodiments of the surgical systems 19 (FIG. 1) and 190 (FIG. 10), operations for the above surgical systems 19, 190 may be further described generally in terms of a process for cutting and coagulating tissue employing a surgical instrument comprising the input device 406 and the tissue impedance module 502. Although a particular process is described in connection with the operational details, it can be appreciated that the process merely provides an example of how the general functionality described herein can be implemented by the surgical systems 19, 190. Further, the given process does not necessarily have to be executed in the order presented herein unless otherwise indicated. As previously discussed, the input device 406 may be employed to program the stepped output (e.g., current, frequency) to the ultrasonic transducer 50/blade 79 assembly.

Figure 14:
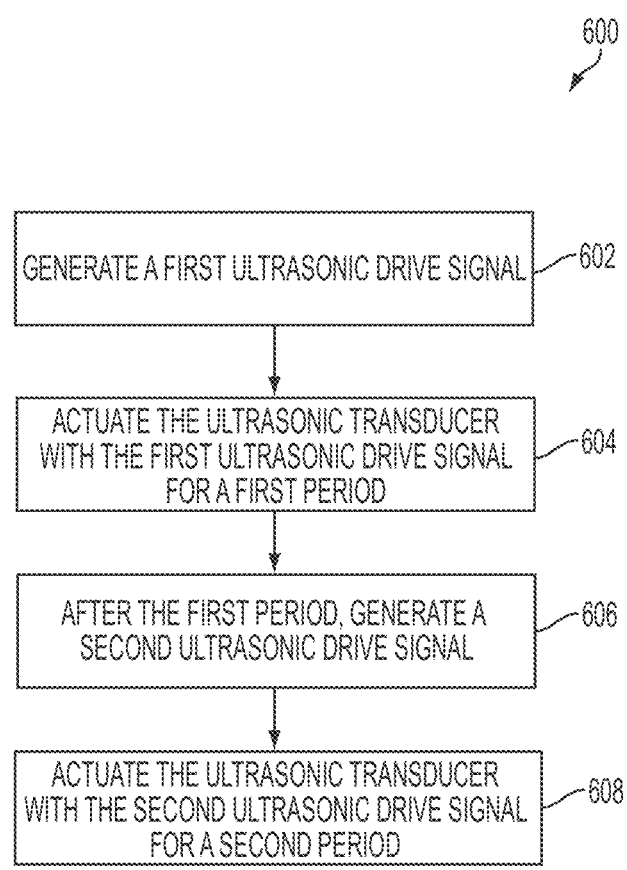
FIG. 14 illustrates one embodiment of a method for driving an end effector coupled to an ultrasonic drive system of a surgical instrument.

FIG. 14 illustrates one embodiment of a method 600 for driving an end effector coupled to an ultrasonic drive system of a surgical instrument. With reference to FIGS. 1-3, and 6-14, by way of example, and not limitation, the ultrasonic surgical instruments 100, 120 may be operated in accordance with the method 600 to separate the inner muscle layer of a vessel from the adventitia layer prior to transecting and sealing the vessel. Accordingly, in various embodiments, an end effector (e.g., end effector 81, 810) of a surgical instrument (e.g., surgical instrument 100, 120) may be driven in accordance with the method 600. A generator (e.g., generator 30, 500) is coupled to an ultrasonic drive system. The ultrasonic drive system comprises an ultrasonic transducer (e.g., ultrasonic transducer 50) coupled to a waveguide (e.g., waveguide 80) and the end effector 81 is coupled to the waveguide 80. The ultrasonic drive system is configured to resonate at a resonant frequency (e.g., 55.5 kHz). In one embodiment, at 602, the generator 30 generates a first ultrasonic drive signal. At 604, the ultrasonic transducer 50 is actuated with the first ultrasonic drive signal for a first period in response to activating a switch (e.g., switch 34) on a handle assembly (e.g., handle assembly 68) or a foot switch (e.g., foot switch 434) connected to the generator 30. After the first period, at 606, the generator 30 generates a second ultrasonic drive signal. At 608, the ultrasonic transducer 50 is actuated with the second ultrasonic drive signal for a second period in response to activating the switch 34 on the handle assembly 68 or the foot switch 434 connected to the generator 30. The first drive signal is different from the second drive signal over the respective first and second periods. The first and second drive signals define a step function waveform over the first and second periods.

In one embodiment, the generator 30 generates a third ultrasonic drive signal. The ultrasonic transducer 50 is actuated with the third ultrasonic drive signal for a third period. The third drive signal is different from the first second drive signals over the first, second, and third periods. The first, second, and third drive signals define a step function waveform over the first, second, and third periods. In one embodiment, generating the first, second, and third ultrasonic drive signals comprises generating a corresponding first, second, and third drive current and actuating the ultrasonic transducer 50 with the first drive current for the first period, actuating the ultrasonic transducer 50 with the second drive current for the second period, and actuating the ultrasonic transducer 50 with the third drive current for the third period.

In one embodiment, the generator 30 generates the first ultrasonic drive signal at a first frequency, which is different from the resonant frequency. The ultrasonic transducer 50 is then actuated with the first ultrasonic drive signal at the first frequency for the first period. Actuation at the first frequency provides a first level of mechanical vibration to the end effector 81 suitable for separating a first tissue from a second tissue, for example, to separate the inner muscle layer of a vessel from the adventitia layer. The generator 30 generates the second ultrasonic drive signal at the resonant frequency, e.g., 55.5 kHz, and the actuates the ultrasonic transducer 50 with the second ultrasonic drive signal at the resonant frequency for the second period subsequent to the first period. Actuation at the second, resonant frequency, provides a second level of mechanical vibration to the end effector 81 suitable for transecting and sealing the first tissue, such as the vessel, once it separated from the inner muscle layer. In one embodiment, the second ultrasonic drive signal at the resonant frequency is generated automatically by the generator 30 after the first period. In one embodiment, the first frequency is substantially different from the resonant frequency and the first period is less than about one second. For example, in one embodiment, the first frequency is defined by the following equation: $f_1=2*f_o$, wherein $f_1$ is the first frequency and $f_o$ is the resonant frequency. In another embodiment, the first frequency is defined by the following equation: $f_1=f_o/2$, wherein $f_1$ is the first frequency and $f_o$ is the resonant frequency. The first, second, and third ultrasonic drive signals are also envisioned to excite be vibratory modes of the ultrasonic transducer 50 in longitudinal, flexural, and torsional modes and harmonics thereof.

In one embodiment, the generator 30 monitors a measurable characteristic of the ultrasonic drive system and generates any one of the first and second drive signals based on the measured characteristic. For example, the generator 30 monitors the impedance Z of the ultrasonic transducer 50. The generator 30 comprises electronic circuitry suitable for measuring the impedance of the transducer 50. For example, a current sense circuit (e.g., current sense circuit 426) senses the current flowing through the transducer 50 and a voltage sense circuit (e.g., voltage sense circuit 428) senses the output voltage applied to the transducer 50. A multiplexer (e.g., multiplexer 430) routes the appropriate analog signal to an analog-to-digital converter (e.g., ADC 432), whose digital output is provided to a processor (e.g., processor 400). The processor 400 calculates the transducer impedance Z based on the measured values of current and voltage.

In one embodiment, the generator 500 comprises an impedance module (e.g., tissue impedance module 502) to measure the impedance of a tissue portion contacting an end effector (e.g., end effector 810). The impedance module 502 includes an RF oscillator (e.g., RF oscillator 506) to generate a subtherapeutic RF signal. The subtherapeutic RF signal is applied to a blade (e.g., blade 79) portion of the end effector 810, which forms an energizing electrode. The tissue portion is grasped between the end effector 810 and a return electrode of a clamp arm assembly (e.g., clamp arm assembly 451) and the impedance of the tissue (e.g., tissue 514). The tissue impedance is then measured by a voltage sense circuit (e.g., voltage sense circuit 508) and current sense circuit (e.g., current sense circuit 510) and of the impedance module 502. These signals are applied to the ADC 432 via the multiplexer 430. The digital output of the ADC 432 is provided to the processor 400, which calculates the tissue impedance Zt based on the measured values of current through the tissue and the voltage applied to the blade 79 portion of the end effector 810.

Figure 15A:
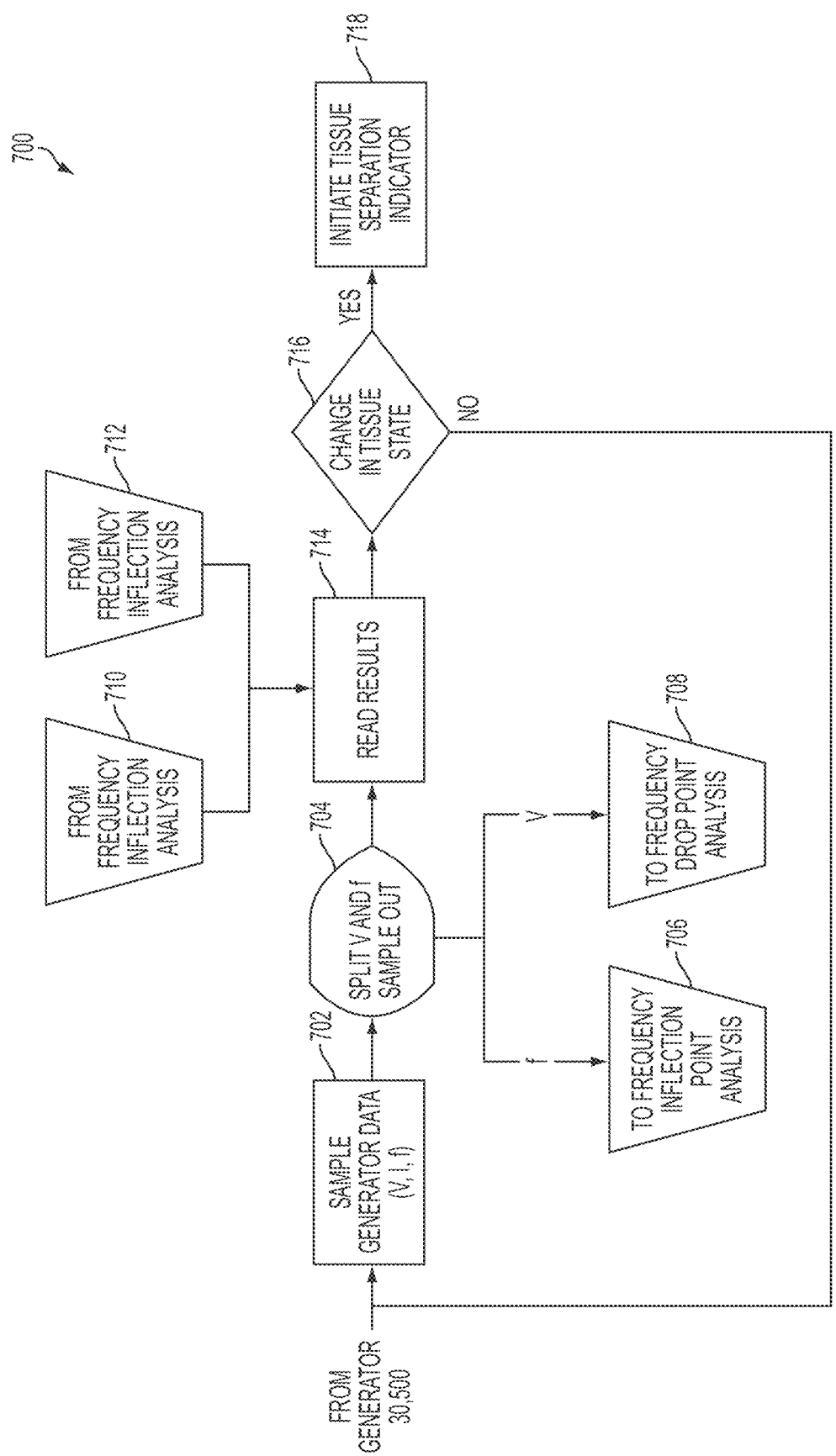
FIG. 15A illustrates a logic flow diagram of one embodiment of determining a change in tissue state and activating an output indicator accordingly.
Figure 15B:
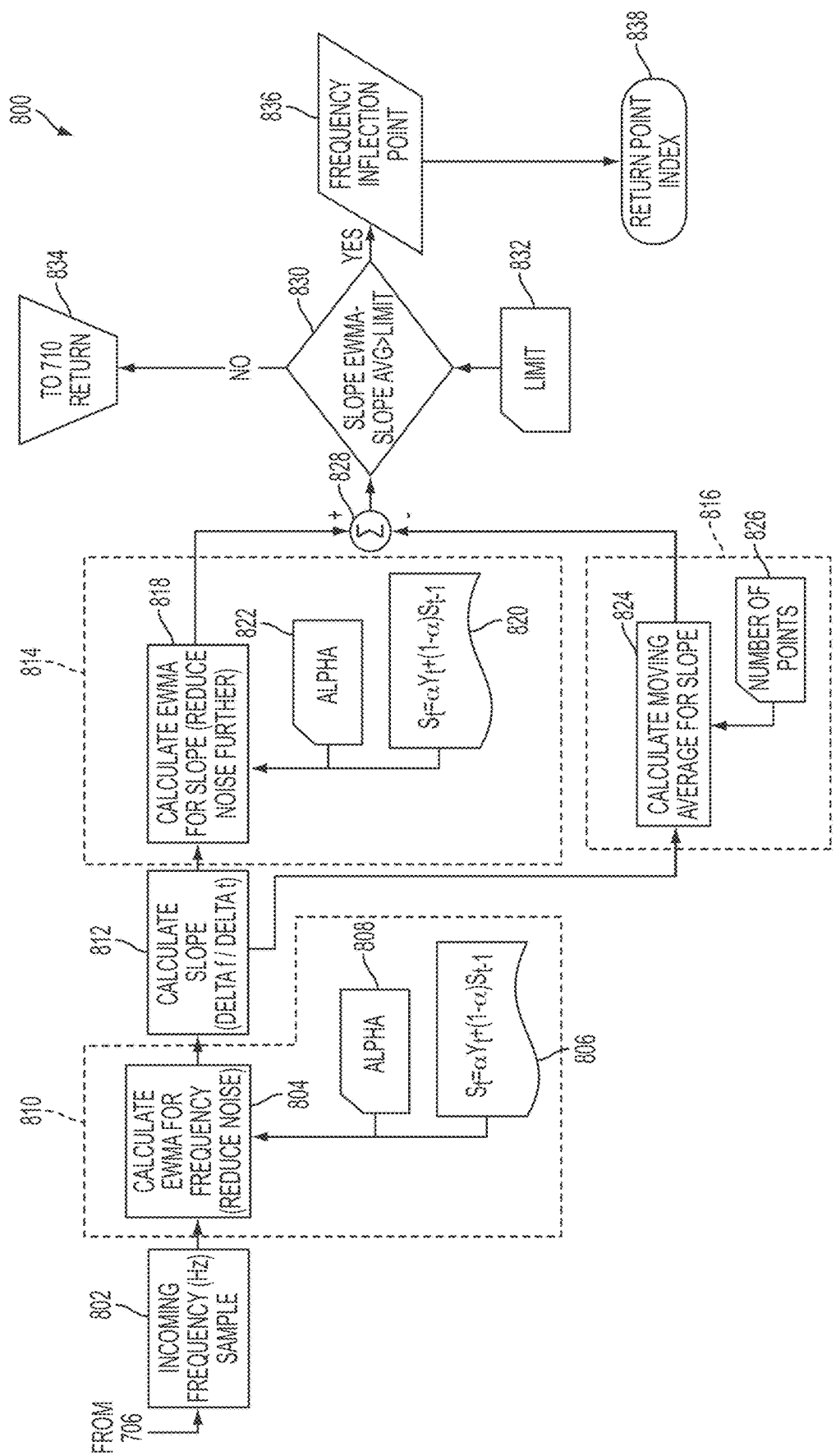
FIG. 15B is a logic flow diagram illustrating one embodiment of the operation of the frequency inflection point analysis module.
Figure 15C:
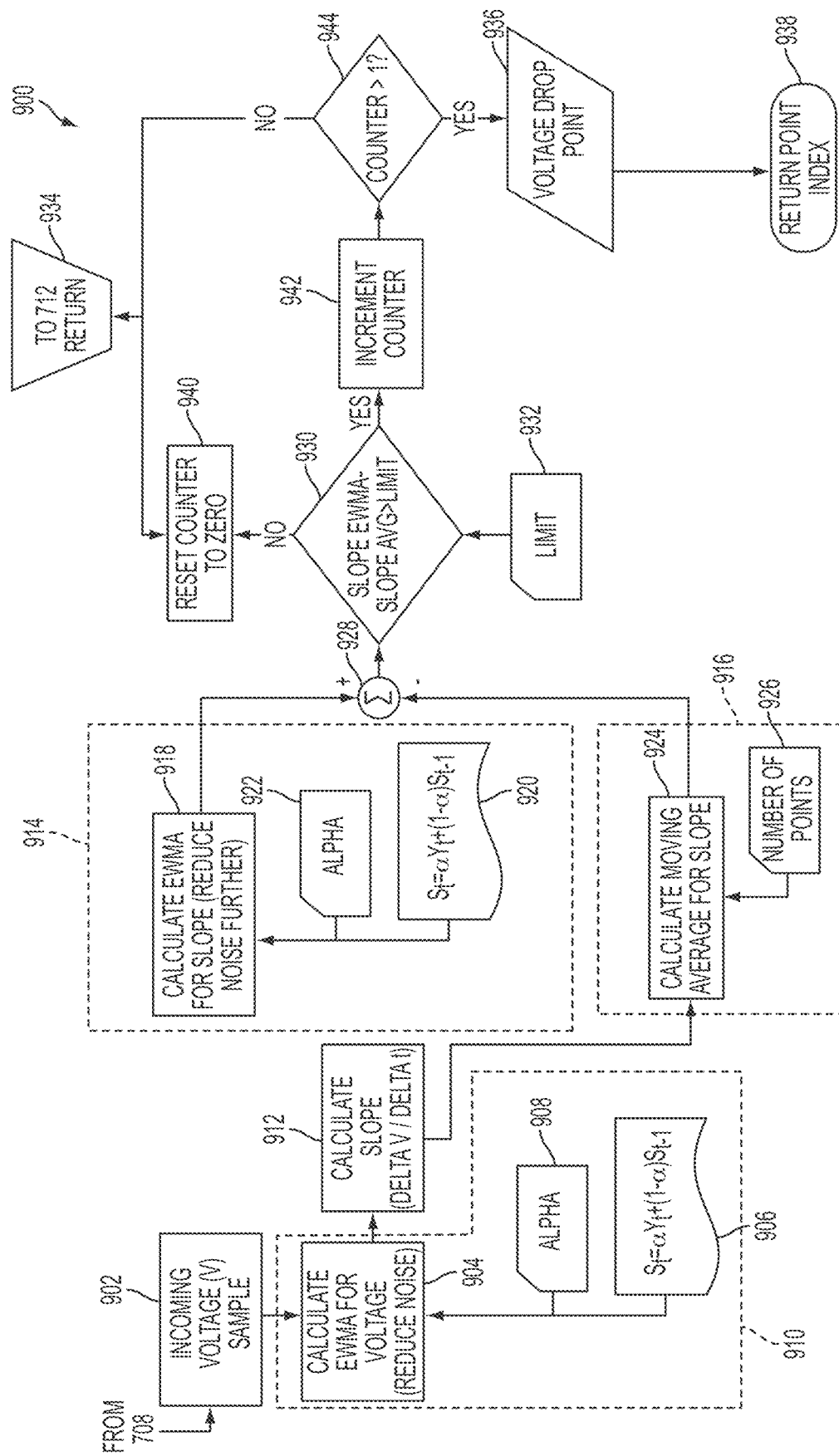
FIG. 15C is a logic flow diagram 900 illustrating one embodiment of the operation of the voltage drop analysis module.

FIGS. 15A-C illustrate various embodiments of logic flow diagrams of 700, 800, 900 of operations for determining a change of state of tissue being manipulated by an ultrasonic surgical instrument and providing feedback to the user to indicate that the tissue has undergone such change of state or that there is a high likelihood that the tissue has undergone such change of state. As used herein, the tissue may undergo a change of state when the tissue is separated from other layers of tissue or bone, when the tissue is cut or transected, when the tissue is coagulated, and so forth while being manipulated with an end effector of an ultrasonic surgical instrument, such as, for example, the end effector 81, 810 of the ultrasonic surgical instrument 100, 120 shown in FIGS. 1 and 10. A change in tissue state may be determined based on the likelihood of an occurrence of a tissue separation event.

In various embodiments, the feedback is provided by the output indicator 412 shown in FIGS. 9 and 11. The output indicator 412 is particularly useful in applications where the tissue being manipulated by the end effector 81, 810 is out of the user's field of view and the user cannot see when a change of state occurs in the tissue. The output indicator 412 communicates to the user that a change in tissue state has occurred as determined in accordance with the operations described with respect to the logic flow diagrams 700, 800, 900. As previously discussed, the output indicator 412 may be configured to provide various types of feedback to the user including, without limitation, visual, audible, and/or tactile feedback to indicate to the user (e.g., surgeon, clinician) that the tissue has undergone a change of state or condition of the tissue. By way of example, and not limitation, as previously discussed, visual feedback comprises any type of visual indication device including incandescent lamps or LEDs, graphical user interface, display, analog indicator, digital indicator, bar graph display, digital alphanumeric display. By way of example, and not limitation, audible feedback comprises any type of buzzer, computer generated tone, computerized speech, VUI to interact with computers through a voice/speech platform. By way of example, and not limitation, tactile feedback comprises any type of vibratory feedback provided through the instrument housing handle assembly 68. The change of state of the tissue may be determined based on transducer and tissue impedance measurements as previously described, or based on voltage, current, and frequency measurements in accordance with the operations described with respect to the logic flow diagrams 700, 800, 900 described below with respect to FIGS. 15A-C.

In one embodiment, the logic flow diagrams 700, 800, 900 may be implemented as executable modules (e.g., algorithms) comprising computer readable instructions to be executed by the processor 400 (FIGS. 9, 11, 14) portion of the generator 30, 500. In various embodiments, the operations described with respect to the logic flow diagrams 700, 800, 900 may be implemented as one or more software components, e.g., programs, subroutines, logic; one or more hardware components, e.g., processors, DSPs, PLDs, ASICs, circuits, registers; and/or combinations of software and hardware. In one embodiment, the executable instructions to perform the operations described by the logic flow diagrams 700, 800, 900 may be stored in memory. When executed, the instructions cause the processor 400 to determine a change in tissue state in accordance with the operations described in the logic flow diagrams 800 and 900 and provide feedback to the user by way of the output indicator 412. In accordance with such executable instructions, the processor 400 monitors and evaluates the voltage, current, and/or frequency signal samples available from the generator 30, 500 and according to the evaluation of such signal samples determines whether a change in tissue state has occurred. As further described below, a change in tissue state may be determined based on the type of ultrasonic instrument and the power level that the instrument is energized at. In response to the feedback, the operational mode of the ultrasonic surgical instrument 100, 120 may be controlled by the user or may be automatically or semi-automatically controlled.

FIG. 15A illustrates a logic flow diagram 700 of one embodiment of determining a change in tissue state and activating the output indicator 412 accordingly. With reference now to the logic flow diagram 700 shown in FIG. 15A and the drive system 32 of the generator 30 shown in FIG. 9, at 702, the processor 400 portion of the drive system 32 samples the voltage (v), current (i), and frequency (f) signals of the generator 30. In the illustrated embodiment, at 704, the frequency and voltage signal samples are analyzed separately to determine the corresponding frequency inflection and/or voltage drop points. In other embodiments, the current signal samples may be separately analyzed in addition to the voltage and frequency signal samples or in place of the voltage signal samples. At 706, the present frequency signal sample is provided to a frequency inflection point analysis module for determining a change in tissue state as illustrated in the logic flow diagram 800 in FIG. 15B. At 708, the present voltage signal sample is provided to a voltage drop point analysis module for determining a change in tissue state as illustrated in the logic flow diagram 900 in FIG. 15C.

The frequency inflection point analysis module and the voltage drop point analysis module determine when a change in tissue state has occurred based on correlated empirical data associated with a particular ultrasonic instrument type and the energy level at which the instrument is driven. At 714, the results 710 from the frequency inflection point analysis module and/or the results 712 from the voltage drop point analysis module are read by the processor 400. The processor 400 determines 716 whether the frequency inflection point result 710 and/or the voltage drop point result 712 indicates a change in tissue state. If the results 710, 714 do not indicate a change in tissue state, the processor 400 continues along the "No" branch to 702 and reads an additional voltage and frequency signal sample from the generator 30. In embodiments that utilize the generator current in the analysis, the processor 400 would now also read an additional current signal sample from the generator 30. If the results 710, 714 indicate a sufficient change in tissue state, the processor 400 continues along the "Yes" branch to 718 and activates the output indicator 412.

As previously discussed, the output indicator 412 may provide visual, audible, and/or tactile feedback to alert the user of the ultrasonic surgical instrument 100, 120 that a change in tissue state has occurred. In various embodiments, in response to the feedback from the output indicator 412, the operational mode of the generator 30, 500 and/or the ultrasonic instrument 100, 120 may be controlled manually, automatically, or semi-automatically. The operational modes include, without limitation, disconnecting or shutting down the output power of the generator 30, 500, reducing the output power of the generator 30, 500, cycling the output power of the generator 30, 500, pulsing the output power of the generator 30, 500, and/or outputting a high-power momentary surge from the generator 30, 500. The operational modes of the ultrasonic instrument in response to the change in tissue state can be selected, for example, to minimize heating effects of the end effector 81, 810, e.g., of the clamp pad 58 (FIGS. 1-3), to prevent or minimize possible damage to the surgical instrument 100, 120 and/or surrounding tissue. This is advantageous because heat is generated rapidly when the transducer 50 is activated with nothing between the jaws of the end effector 81, 810 as is the case when a change in tissue state occurs such as when tissue has substantially separated from the end effector.

FIG. 15B is a logic flow diagram 800 illustrating one embodiment of the operation of the frequency inflection point analysis module. At 802, a frequency sample is received by the processor 400 from 706 of the logic flow diagram 700. At 804, the processor 400 calculates an exponentially weighted moving average (EWMA) for the frequency inflection analysis. The EWMA is calculated to filter out noise from the generator from the frequency samples. The EWMA is calculated in accordance with a frequency moving average equation 806 and an alpha value (α) 808:

$$S_{tf} = \alpha Y_{tf} + (1-\alpha) S_{tf-1} \qquad (2)$$

Where:
  $S_{tf}$=the current moving average of the sampled frequency signal;
  $S_{tf-1}$=the previous moving average of the sampled frequency signal;
  α=the smoothing factor; and
  $Y_{tf}$=current data point of the sampled frequency signal.

The α value 808 may vary from about 0 to about 1 in accordance with a desired filtering or smoothing factor, wherein small α values 808 approaching about 0 provide a large amount of filtering or smoothing and large α values 808 approaching about 1 provide a small amount of filtering or smoothing. The α value 808 may be selected based on the ultrasonic instrument type and power level. In one embodiment, blocks 804, 806, and 808 may be implemented as a variable digital low pass filter 810 with the α value 808 determining the cutoff point of the filter 810. Once the frequency samples are filtered, the slope of the frequency samples is calculated at 812 as:

$$\text{Frequency Slope} = \Delta f / \Delta t \qquad (3)$$

The calculated Frequency Slope data points are provided to a "slow response" moving average filter 814 to calculate the EWMA moving average for the Frequency Slope to further reduce system noise. In one embodiment, the "slow response" moving average filter 814 may be implemented by calculating the EWMA for the Frequency Slope at 818 in accordance with the frequency slope moving average equation 820 and alpha value (α') 822:

$$S'_{tf} = \alpha' Y'_{tf} + (1-\alpha') S'_{tf-1} \qquad (4)$$

Where:

S'$_{tf}$=the current moving average of the frequency slope of the sampled frequency signal;

S'$_{tf-1}$=the previous moving average of the frequency slope of the sampled frequency signal;

α'=the smoothing factor; and

Y'$_{tf}$=current slope data point of the sampled frequency signal.

The α' value 822 varies from about 0 to about 1, as previously discussed with respect to digital filter block 810 in accordance with a desired filtering or smoothing factor, wherein small α' value 822 approaching 0 provide a large amount of filtering or smoothing and large α' value 822 approaching 1 provide a small amount of filtering or smoothing. The α' value 822 may be selected based on the ultrasonic instrument type and power level.

The calculated Frequency Slope data points are provided to a "fast response" filter 816 to calculate the moving average for the Frequency Slope. At 824, the "fast response" filter 816 calculates the moving average for the Frequency Slope based on a number of data points 826.

In the illustrated embodiment, the output of the "slow response" moving average filter 814 "Slope EWMA" is applied to a (+) input of an adder 828 and the output of the "fast response" filter 816 "Slope Avg" is applied to (−) input of the adder 828. The adder 828 computes the difference between the outputs of the "slow response" moving average filter 814 and the "fast response" filter 816. The difference between these outputs is compared at 830 to a predetermined limit 832. The limit 832 is determined based on the type of ultrasonic instrument and the power level at which the particular type of ultrasonic instrument is energized at. The limit 832 value may be predetermined and stored in memory in the form of a look-up table or the like. If the difference between the "Slope EWMA" and the "Slope Avg" is not greater than the limit 832, the processor 400 continues along the "No" branch and returns α value 834 to the results 710 block that indicates that no inflection point was found in the sampled frequency signal and, therefore, no change in tissue state was detected. However, if the difference between the "Slope EWMA" and the "Slope Avg" is greater than the limit 832, the processor 400 continues along the "Yes" branch and determines that a frequency inflection point 836 was found and returns point index 838 to the results 710 block indicating that an inflection point was found in the sampled frequency data and, therefore, a change in tissue state was detected. As previously discussed with reference to FIG. 15A, if a frequency inflection point 836 is found, then, at 718 (FIG. 15A) the processor 400 activates the change in tissue state indicator 718.

FIG. 15C is a logic flow diagram 900 illustrating one embodiment of the operation of the voltage drop analysis module. At 902, a voltage sample is received by the processor 400 from 708 of the logic flow diagram 700. At 904, the processor 400 calculates an exponentially weighted moving average (EWMA) for the frequency inflection analysis. The EWMA is calculated to filter out noise from the generator from the frequency samples. The EWMA is calculated in accordance with a voltage moving average equation 906 and an alpha value (α) 908:

$$S_{tv}=\alpha Y_{tv}+(1-\alpha)S_{tv-1} \quad (5)$$

Where:

S$_{tv}$=the current moving average of the sampled voltage signal;

S$_{tv-1}$=the previous moving average of the sampled voltage signal;

α=the smoothing factor; and

Y$_{tv}$=current data point of the sampled voltage signal.

As previously discussed, the α value 908 may vary from 0 to 1 in accordance with a desired filtering or smoothing factor and may be selected based on the ultrasonic instrument type and power level. In one embodiment, blocks 904, 906, and 908 may be implemented as a variable digital low pass filter 910 with the α value 908 determining the cutoff point of the filter 910. Once the voltage samples are filtered, the slope of the voltage samples is calculated at 912 as:

$$\text{Voltage Slope}=\Delta v/\Delta t \quad (6)$$

The calculated Voltage Slope data points are provided to a "slow response" moving average filter 914 to calculate the EWMA moving average for the Voltage Slope to further reduce system noise. In one embodiment, the "slow response" moving average filter 914 may be implemented by calculating the EWMA for the Voltage Slope at 918 in accordance with the voltage slope moving average equation 920 and alpha value (α') 822:

$$S'_{tv}=\alpha' Y'_{tv}+(1-\alpha')S'_{tv-1} \quad (7)$$

Where:

S'$_{tv}$=the current moving average of the voltage slope of the sampled voltage signal;

S'$_{tv-1}$=the previous moving average of the voltage slope of the sampled voltage signal;

α'=the smoothing factor; and

Y'$_{tv}$=current slope data point of the sampled voltage signal.

The α' value 922 varies from about 0 to about 1, as previously discussed with respect to digital filter block 910 in accordance with a desired filtering or smoothing factor, wherein small α' value 922 approaching about 0 provide a large amount of filtering or smoothing and large α' value 922 approaching about 1 provide a small amount of filtering or smoothing. The α' value 922 may be selected based on the ultrasonic instrument type and power level.

The calculated Voltage Slope data points are provided to a "fast response" filter 916 to calculate the moving average for the Voltage Slope. At 924, the "fast response" filter 916 calculates the moving average for the Voltage Slope based on a number of data points 926.

In the illustrated embodiment, the output of the "slow response" moving average filter 914 "Slope EWMA" is applied to a (+) input of an adder 928 and the output of the "fast response" filter 916 "Slope Avg" is applied to (−) input of the adder 928. The adder 928 computes the difference between the outputs of the "slow response" moving average filter 914 and the "fast response" filter 916. The difference between these outputs is compared at 930 to a predetermined limit 932. The limit 932 is determined based on the type of ultrasonic instrument and the power level at which the particular type of ultrasonic instrument is energized at. The limit 932 value may be predetermined and stored in memory in the form of a look-up table or the like. If the difference between the "Slope EWMA" and the "Slope Avg" is not greater than the limit 932, the processor 400 continues along the "No" branch and resets a counter to zero at 940, then returns α value 934 to the results 710 block that indicates that no voltage drop point was found in the sampled voltage signals and, therefore, no change in tissue state was detected.

However, if the difference between the "Slope EWMA" and the "Slope Avg" is greater than the limit 932, the processor 400 continues along the "Yes" branch and increments a counter at 942. At 944, the processor 400 decides whether the counter is greater than 1, or some other predetermined threshold value for example. In other words, the processor 400 takes at least two data points in regards to the voltage drop point. If the counter is not greater than the threshold (e.g., 1 in the illustrated embodiment) the processor 400 continues along the "No" branch and returns α value 934 to the results 710 block that indicates that no voltage drop point was found in the sampled voltage signals and, therefore, no change in tissue state was detected. If the counter is greater than the threshold (e.g., 1 in the illustrated embodiment) the processor 400 continues along the "Yes" branch and determines that a voltage drop point 936 was found and returns a point index 938 to the results 712 block indicating that a voltage drop point was found in the sampled voltage signals and, therefore, a change in tissue state was detected. As previously discussed with reference to FIG. 15A, if a voltage point 836 is found, then, at 718 (FIG. 15A) the processor 400 activates the change in tissue state indicator 718.

FIG. 16 illustrates one embodiment of a surgical system 1000 comprising a generator 1002 and various surgical instruments usable therewith. The generator 1002 is configurable for use with surgical devices. According to various embodiments, the generator 1002 may be configurable for use with different surgical devices of different types including, for example, the ultrasonic device 1004 and electrosurgical or RF surgical devices, such as, the RF device 1006. Although in the embodiment of FIG. 16, the generator 1002 is shown separate from the surgical devices 1004, 1006, in one embodiment, the generator 1002 may be formed integrally with either of the surgical devices 1004, 1006 to form a unitary surgical system. The generator 1002 comprises an input device 1009 located on a front panel of the generator 1002 console. The input device 1009 may comprise any suitable device that generates signals suitable for programming the operation of the generator 1002.

Figure 17:
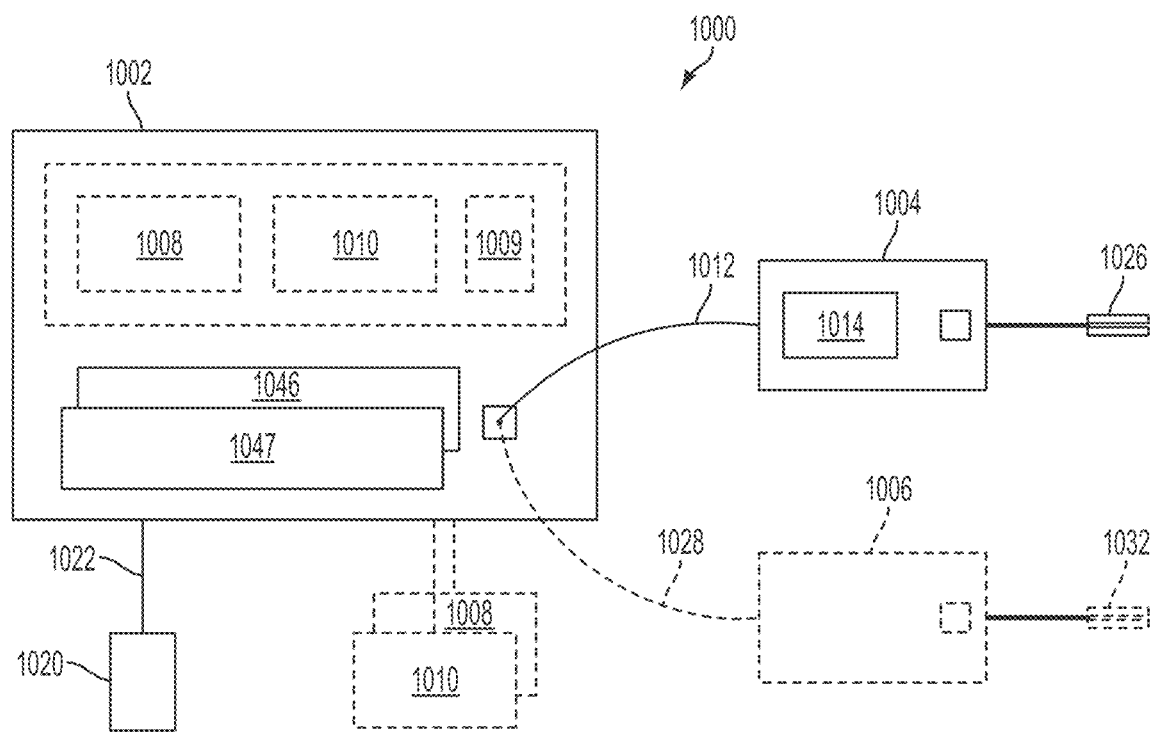
FIG. 17 is a diagram of the surgical system of FIG. 16.

FIG. 17 is a diagram of the surgical system 1000 of FIG. 16. In various embodiments, the generator 1002 may comprise several separate functional elements, such as modules and/or blocks. Different functional elements or modules may be configured for driving the different kinds of surgical devices 1004, 1006. For example, an ultrasonic generator module 1008 may drive ultrasonic devices such as the ultrasonic device 1004. An electrosurgery/RF generator module 1010 may drive the electrosurgical device 1006. For example, the respective modules 1008, 1010 may generate respective drive signals for driving the surgical devices 1004, 1006. In various embodiments, the ultrasonic generator module 1008 and/or the electrosurgery/RF generator module 1010 each may be formed integrally with the generator 1002. Alternatively, one or more of the modules 1008, 1010 may be provided as a separate circuit module electrically coupled to the generator 1002. (The modules 1008 and 1010 are shown in phantom to illustrate this option.) Also, in some embodiments, the electrosurgery/RF generator module 1010 may be formed integrally with the ultrasonic generator module 1008, or vice versa.

In accordance with the described embodiments, the ultrasonic generator module 1008 may produce a drive signal or signals of particular voltages, currents, and frequencies, e.g., 55,500 cycles per second (Hz). The drive signal or signals may be provided to the ultrasonic device 1004, and specifically to the transducer 1014, which may operate, for example, as described above. In one embodiment, the generator 1002 may be configured to produce a drive signal of a particular voltage, current, and/or frequency output signal that can be stepped with high resolution, accuracy, and repeatability.

The generator 1002 may be activated to provide the drive signal to the transducer 1014 in any suitable manner. For example, the generator 1002 may comprise a foot switch 1020 coupled to the generator 1002 via a footswitch cable 1022. A clinician may activate the transducer 1014 by depressing the foot switch 1020. In addition, or instead of the foot switch 1020 some embodiments of the ultrasonic device 1004 may utilize one or more switches positioned on the hand piece that, when activated, may cause the generator 1002 to activate the transducer 1014. In one embodiment, for example, the one or more switches may comprise a pair of toggle buttons 1036a, 1036b (FIG. 16), for example, to determine an operating mode of the device 1004. When the toggle button 1036a is depressed, for example, the ultrasonic generator 1002 may provide a maximum drive signal to the transducer 1014, causing it to produce maximum ultrasonic energy output. Depressing toggle button 1036b may cause the ultrasonic generator 1002 to provide a user-selectable drive signal to the transducer 1014, causing it to produce less than the maximum ultrasonic energy output. The device 1004 additionally or alternatively may comprise a second switch (not shown) to, for example, indicate a position of a jaw closure trigger for operating jaws of the end effector 1026. Also, in some embodiments, the ultrasonic generator 1002 may be activated based on the position of the jaw closure trigger, (e.g., as the clinician depresses the jaw closure trigger to close the jaws, ultrasonic energy may be applied).

Additionally or alternatively, the one or more switches may comprises a toggle button 1036c that, when depressed, causes the generator 1002 to provide a pulsed output. The pulses may be provided at any suitable frequency and grouping, for example. In certain embodiments, the power level of the pulses may be the power levels associated with toggle buttons 1036a, 1036b (maximum, less than maximum), for example.

It will be appreciated that a device 1004 may comprise any combination of the toggle buttons 1036a, 1036b, 1036c. For example, the device 1004 could be configured to have only two toggle buttons: a toggle button 1036a for producing maximum ultrasonic energy output and a toggle button 1036c for producing a pulsed output at either the maximum or less than maximum power level. In this way, the drive signal output configuration of the generator 1002 could be 5 continuous signals and 5 or 4 or 3 or 2 or 1 pulsed signals. In certain embodiments, the specific drive signal configuration may be controlled based upon, for example, EEPROM settings in the generator 1002 and/or user power level selection(s).

In certain embodiments, a two-position switch may be provided as an alternative to a toggle button 1036c. For example, a device 1004 may include a toggle button 1036a for producing a continuous output at a maximum power level and a two-position toggle button 1036b. In a first detented position, toggle button 1036b may produce a continuous output at a less than maximum power level, and in a second detented position the toggle button 1036b may produce a pulsed output (e.g., at either a maximum or less than maximum power level, depending upon the EEPROM settings).

In accordance with the described embodiments, the electrosurgery/RF generator module 1010 may generate a drive signal or signals with output power sufficient to perform bipolar electrosurgery using radio frequency (RF) energy. In bipolar electrosurgery applications, the drive signal may be provided, for example, to electrodes of the electrosurgical device 1006, for example. Accordingly, the generator 1002 may be configured for therapeutic purposes by applying electrical energy to the tissue sufficient for treating the tissue (e.g., coagulation, cauterization, tissue welding).

The generator 1002 may comprise an input device 1045 (FIG. 16) located, for example, on a front panel of the generator 1002 console. The input device 1045 may comprise any suitable device that generates signals suitable for programming the operation of the generator 1002. In operation, the user can program or otherwise control operation of the generator 1002 using the input device 1045. The input device 1045 may comprise any suitable device that generates signals that can be used by the generator (e.g., by one or more processors contained in the generator) to control the operation of the generator 1002 (e.g., operation of the ultrasonic generator module 1008 and/or electrosurgery/RF generator module 1010). In various embodiments, the input device 1045 includes one or more of buttons, switches, thumbwheels, keyboard, keypad, touch screen monitor, pointing device, remote connection to a general purpose or dedicated computer. In other embodiments, the input device 1045 may comprise a suitable user interface, such as one or more user interface screens displayed on a touch screen monitor, for example. Accordingly, by way of the input device 1045, the user can set or program various operating parameters of the generator, such as, for example, current (I), voltage (V), frequency (f), and/or period (T) of a drive signal or signals generated by the ultrasonic generator module 1008 and/or electrosurgery/RF generator module 1010.

The generator 1002 may also comprise an output device 1047 (FIG. 16), such as an output indicator, located, for example, on a front panel of the generator 1002 console. The output device 1047 includes one or more devices for providing a sensory feedback to a user. Such devices may comprise, for example, visual feedback devices (e.g., a visual feedback device may comprise incandescent lamps, light emitting diodes (LEDs), graphical user interface, display, analog indicator, digital indicator, bar graph display, digital alphanumeric display, LCD display screen, LED indicators), audio feedback devices (e.g., an audio feedback device may comprise speaker, buzzer, audible, computer generated tone, computerized speech, voice user interface (VUI) to interact with computers through a voice/speech platform), or tactile feedback devices (e.g., a tactile feedback device comprises any type of vibratory feedback, haptic actuator).

Although certain modules and/or blocks of the generator 1002 may be described by way of example, it can be appreciated that a greater or lesser number of modules and/or blocks may be used and still fall within the scope of the embodiments. Further, although various embodiments may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In one embodiment, the ultrasonic generator drive module 1008 and electrosurgery/RF drive module 1010 may comprise one or more embedded applications implemented as firmware, software, hardware, or any combination thereof. The modules 1008, 1010 may comprise various executable modules such as software, programs, data, drivers, application program interfaces (APIs), and so forth. The firmware may be stored in nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In one embodiment, the modules 1008, 1010 comprise a hardware component implemented as a processor for executing program instructions for monitoring various measurable characteristics of the devices 1004, 1006 and generating a corresponding output control signals for operating the devices 1004, 1006. In embodiments in which the generator 1002 is used in conjunction with the device 1004, the output control signal may drive the ultrasonic transducer 1014 in cutting and/or coagulation operating modes. Electrical characteristics of the device 1004 and/or tissue may be measured and used to control operational aspects of the generator 1002 and/or provided as feedback to the user. In embodiments in which the generator 1002 is used in conjunction with the device 1006, the output control signal may supply electrical energy (e.g., RF energy) to the end effector 1032 in cutting, coagulation and/or desiccation modes. Electrical characteristics of the device 1006 and/or tissue may be measured and used to control operational aspects of the generator 1002 and/or provide feedback to the user. In various embodiments, as previously discussed, the hardware component may be implemented as a DSP, PLD, ASIC, circuits, and/or registers. In one embodiment, the processor may be configured to store and execute computer software program instructions to generate the step function output signals for driving various components of the devices 1004, 1006, such as the ultrasonic transducer 1014 and the end effectors 1026, 1032.

Figure 18:
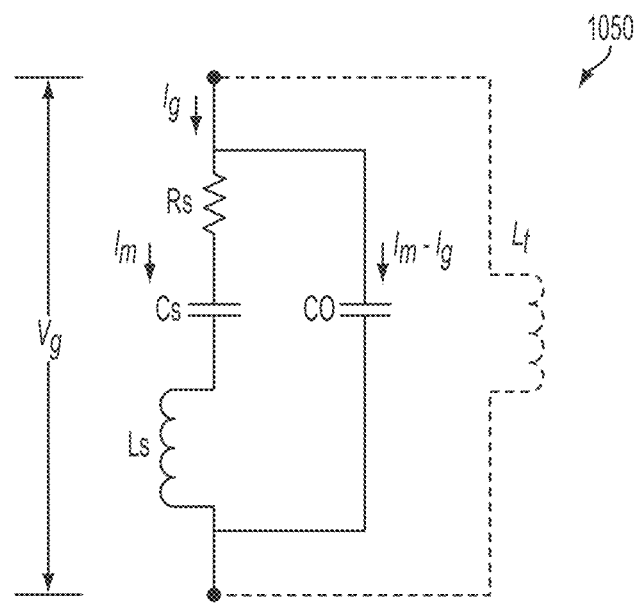
FIG. 18 is a model illustrating motional branch current in one embodiment.

FIG. 18 illustrates an equivalent circuit 1050 of an ultrasonic transducer, such as the ultrasonic transducer 1014, according to one embodiment. The circuit 1050 comprises a first "motional" branch having a serially connected inductance $L_s$, resistance $R_s$ and capacitance $C_s$ that define the electromechanical properties of the resonator, and a second capacitive branch having a static capacitance $C_o$. Drive current $I_g$ may be received from a generator at a drive voltage $V_g$, with motional current $I_m$ flowing through the first branch and current $I_g$-$I_m$ flowing through the capacitive branch. Control of the electromechanical properties of the ultrasonic transducer may be achieved by suitably controlling $I_g$ and $V_g$. As explained above, conventional generator architectures may include a tuning inductor $L_t$ (shown in phantom in FIG. 18) for tuning out in a parallel resonance circuit the static capacitance Co at a resonant frequency so that substantially all of generator's current output $I_g$ flows through the motional branch. In this way, control of the motional branch current $I_m$ is achieved by controlling the generator current output $I_g$. The tuning inductor $L_t$ is specific to the static capacitance $C_o$ of an ultrasonic transducer, however, and a different ultrasonic transducer having a different static capacitance requires a different tuning inductor $L_t$. Moreover, because the tuning inductor $L_t$ is matched to the nominal value of the static capacitance Co at a single resonant frequency, accurate control of the motional branch current $I_m$ is assured only at that frequency, and as frequency shifts down with transducer temperature, accurate control of the motional branch current is compromised.

Embodiments of the generator 1002 do not rely on a tuning inductor $L_t$ to monitor the motional branch current $I_m$. Instead, the generator 1002 may use the measured value of the static capacitance $C_o$ in between applications of power for a specific ultrasonic surgical device 1004 (along with drive signal voltage and current feedback data) to determine values of the motional branch current $I_m$ on a dynamic and ongoing basis (e.g., in real-time). Such embodiments of the generator 1002 are therefore able to provide virtual tuning to simulate a system that is tuned or resonant with any value of static capacitance $C_o$ at any frequency, and not just at single resonant frequency dictated by a nominal value of the static capacitance $C_o$.

Figure 19:
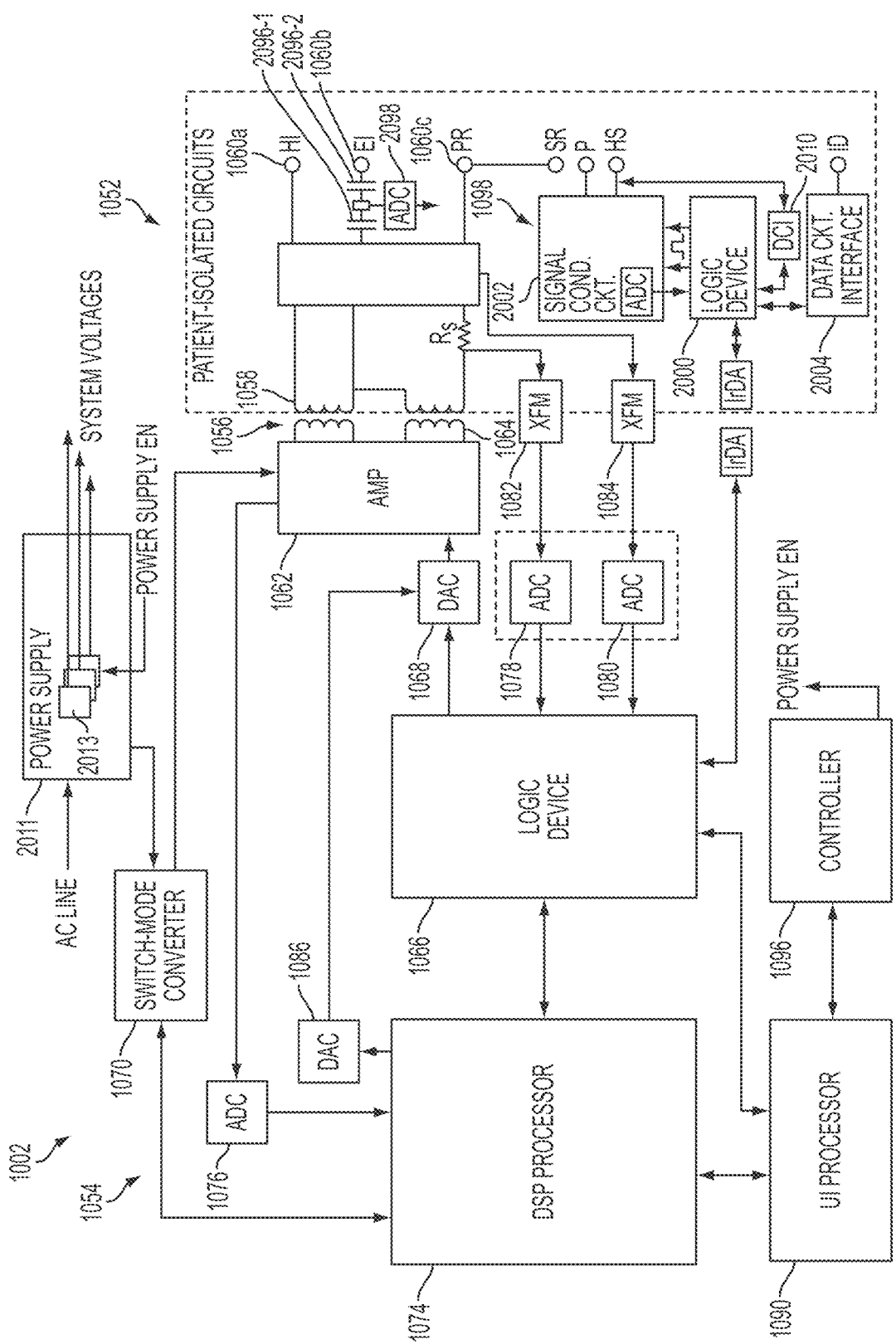
FIG. 19 is a structural view of a generator architecture in one embodiment.

FIG. 19 is a simplified block diagram of one embodiment of the generator 1002 for proving inductorless tuning as described above, among other benefits. Additional details of the generator 1002 are described in commonly assigned and contemporaneously filed U.S. patent application Ser. No. 12/896,360, now U.S. Patent Application Publication No. 2011/0087256 A1, titled "Surgical Generator For Ultrasonic And Electrosurgical Devices," the disclosure of which is incorporated herein by reference in its entirety. With reference to FIG. 19, the generator 1002 may comprise a patient isolated stage 1052 in communication with a non-isolated stage 1054 via a power transformer 1056. A secondary winding 1058 of the power transformer 1056 is contained in the isolated stage 1052 and may comprise a tapped configuration (e.g., a center-tapped or a non-center-tapped configuration) to define drive signal outputs 1060*a*, 1060*b*, 1060*c* for outputting drive signals to different surgical devices, such as, for example, an ultrasonic surgical device 1004 and an electrosurgical device 1006. In particular, drive signal outputs 1060*a*, 1060*c* may output a drive signal (e.g., a 420V RMS drive signal) to an ultrasonic surgical device 1004, and drive signal outputs 1060*b*, 160*c* may output a drive signal (e.g., a 100V RMS drive signal) to an electrosurgical device 1006, with output 1060*b* corresponding to the center tap of the power transformer 1056. The non-isolated stage 1054 may comprise a power amplifier 1062 having an output connected to a primary winding 1064 of the power transformer 1056. In certain embodiments the power amplifier 1062 may be comprise a push-pull amplifier. For example, the non-isolated stage 1054 may further comprise a logic device 1066 for supplying a digital output to a digital-to-analog converter (DAC) 1068, which in turn supplies a corresponding analog signal to an input of the power amplifier 1062. In certain embodiments the logic device 1066 may comprise a programmable gate array (PGA), a field-programmable gate array (FPGA), programmable logic device (PLD), among other logic circuits, for example. The logic device 1066, by virtue of controlling the input of the power amplifier 1062 via the DAC 1068, may therefore control any of a number of parameters (e.g., frequency, waveform shape, waveform amplitude) of drive signals appearing at the drive signal outputs 1060*a*, 1060*b*, 1060*c*. In certain embodiments and as discussed below, the logic device 1066, in conjunction with a processor (e.g., a digital signal processor discussed below), may implement a number of digital signal processing (DSP)-based and/or other control algorithms to control parameters of the drive signals output by the generator 1002.

Power may be supplied to a power rail of the power amplifier 1062 by a switch-mode regulator 1070. In certain embodiments the switch-mode regulator 1070 may comprise an adjustable buck regulator, for example. The non-isolated stage 1054 may further comprise a first processor 1074, which in one embodiment may comprise a DSP processor such as an Analog Devices ADSP-21469 SHARC DSP, available from Analog Devices, Norwood, MA, for example, although in various embodiments any suitable processor may be employed. In certain embodiments the processor 1074 may control operation of the switch-mode power converter 1070 responsive to voltage feedback data received from the power amplifier 1062 by the DSP processor 1074 via an analog-to-digital converter (ADC) 1076. In one embodiment, for example, the DSP processor 1074 may receive as input, via the ADC 1076, the waveform envelope of a signal (e.g., an RF signal) being amplified by the power amplifier 1062. The DSP processor 1074 may then control the switch-mode regulator 1070 (e.g., via a pulse-width modulated (PWM) output) such that the rail voltage supplied to the power amplifier 1062 tracks the waveform envelope of the amplified signal. By dynamically modulating the rail voltage of the power amplifier 1062 based on the waveform envelope, the efficiency of the power amplifier 1062 may be significantly improved relative to a fixed rail voltage amplifier schemes.

In certain embodiments, the logic device 1066, in conjunction with the DSP processor 1074, may implement a direct digital synthesizer (DDS) control scheme to control the waveform shape, frequency and/or amplitude of drive signals output by the generator 1002. In one embodiment, for example, the logic device 1066 may implement a DDS control algorithm by recalling waveform samples stored in a dynamically-updated look-up table (LUT), such as a RAM LUT, which may be embedded in an FPGA. This control algorithm is particularly useful for ultrasonic applications in which an ultrasonic transducer, such as the ultrasonic transducer 1014, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 1002 is impacted by various sources of distortion present in the output drive circuit (e.g., the power transformer 1056, the power amplifier 1062), voltage and current feedback data based on the drive signal may be input into an algorithm, such as an error control algorithm implemented by the DSP processor 1074, which compensates for distortion by suitably pre-distorting or modifying the waveform samples stored in the LUT on a dynamic, ongoing basis (e.g., in real-time). In one embodiment, the amount or degree of pre-distortion applied to the LUT samples may be based on the error between a computed motional branch current and a desired current waveform shape, with the error being determined on a sample-by-sample basis. In this way, the pre-distorted LUT samples, when processed through the drive circuit, may result in a motional branch drive signal having the desired waveform shape (e.g., sinusoidal) for optimally driving the ultrasonic transducer. In such embodiments, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 1054 may further comprise an ADC 1078 and an ADC 1080 coupled to the output of the power transformer 1056 via respective isolation transformers 1082, 1084 for respectively sampling the voltage and current of drive signals output by the generator 1002. In certain embodiments, the ADCs 1078, 1080 may be configured to sample at high speeds (e.g., 80 MSPS) to enable oversampling of the drive signals. In one embodiment, for example, the sampling speed of the ADCs 1078, 1080 may enable approximately 200× (depending on frequency) oversampling of the drive signals. In certain embodiments, the sampling operations of the ADC 1078, 1080 may be performed by a singe ADC receiving input voltage and current signals via a two-way multiplexer. The use of high-speed sampling in embodiments of the generator 1002 may enable, among other things, calculation of the complex current flowing through the motional branch (which may be used in certain embodiments to implement DDS-based waveform shape control described above), accurate digital filtering of the sampled signals, and calculation of real power consumption with a high degree of precision. Voltage and current feedback data output by the ADCs 1078, 1080 may be received and processed (e.g., FIFO buffering, multiplexing) by the logic device 1066 and stored in data memory for subsequent retrieval by, for example, the DSP processor 1074. As noted above, voltage and current feedback data may be used as input to an algorithm for pre-distorting or modifying LUT waveform samples on a dynamic and ongoing basis. In certain embodiments, this may require each stored voltage and current feedback data pair to be indexed based on, or otherwise associated with, a corresponding LUT sample that was output by the logic device 1066 when the voltage and current feedback data pair was acquired. Synchronization of the LUT samples and the voltage and current feedback data in this manner contributes to the correct timing and stability of the pre-distortion algorithm.

In certain embodiments, the voltage and current feedback data may be used to control the frequency and/or amplitude (e.g., current amplitude) of the drive signals. In one embodiment, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the DSP processor 1074, for example, with the frequency control signal being supplied as input to a DDS control algorithm implemented by the logic device 1066.

In another embodiment, for example, the current feedback data may be monitored in order to maintain the current amplitude of the drive signal at a current amplitude setpoint. The current amplitude setpoint may be specified directly or determined indirectly based on specified voltage amplitude and power setpoints. In certain embodiments, control of the current amplitude may be implemented by control algorithm, such as, for example, a PID control algorithm, in the processor 1074. Variables controlled by the control algorithm to suitably control the current amplitude of the drive signal may include, for example, the scaling of the LUT waveform samples stored in the logic device 1066 and/or the full-scale output voltage of the DAC 1068 (which supplies the input to the power amplifier 1062) via a DAC 1086.

The non-isolated stage 1054 may further comprise a second processor 1090 for providing, among other things user interface (UI) functionality. In one embodiment, the UI processor 1090 may comprise an Atmel AT91SAM9263 processor having an ARM 926EJ-S core, available from Atmel Corporation, San Jose, CA, for example. Examples of UI functionality supported by the UI processor 1090 may include audible and visual user feedback, communication with peripheral devices (e.g., via a Universal Serial Bus (USB) interface), communication with the footswitch 1020, communication with an input device 1009 (e.g., a touch screen display) and communication with an output device 1047 (e.g., a speaker). The UI processor 1090 may communicate with the processor 1074 and the logic device 1066 (e.g., via serial peripheral interface (SPI) buses). Although the UI processor 1090 may primarily support UI functionality, it may also coordinate with the DSP processor 1074 to implement hazard mitigation in certain embodiments. For example, the UI processor 1090 may be programmed to monitor various aspects of user input and/or other inputs (e.g., touch screen inputs, footswitch 1020 inputs (FIG. 17), temperature sensor inputs) and may disable the drive output of the generator 1002 when an erroneous condition is detected.

In certain embodiments, both the DSP processor 1074 and the UI processor 1090, for example, may determine and monitor the operating state of the generator 1002. For the DSP processor 1074, the operating state of the generator 1002 may dictate, for example, which control and/or diagnostic processes are implemented by the DSP processor 1074. For the UI processor 1090, the operating state of the generator 1002 may dictate, for example, which elements of a user interface (e.g., display screens, sounds) are presented to a user. The respective DSP and UI processors 1074, 1090 may independently maintain the current operating state of the generator 1002 and recognize and evaluate possible transitions out of the current operating state. The DSP processor 1074 may function as the master in this relationship and determine when transitions between operating states are to occur. The UI processor 1090 may be aware of valid transitions between operating states and may confirm if a particular transition is appropriate. For example, when the DSP processor 1074 instructs the UI processor 1090 to transition to a specific state, the UI processor 1090 may verify that requested transition is valid. In the event that a requested transition between states is determined to be invalid by the UI processor 1090, the UI processor 1090 may cause the generator 1002 to enter a failure mode.

The non-isolated stage 1054 may further comprise a controller 1096 for monitoring input devices 1045 (e.g., a capacitive touch sensor used for turning the generator 1002 on and off, a capacitive touch screen). In certain embodiments, the controller 1096 may comprise at least one processor and/or other controller device in communication with the UI processor 1090. In one embodiment, for example, the controller 1096 may comprise a processor (e.g., a Mega168 8-bit controller available from Atmel) configured to monitor user input provided via one or more capacitive touch sensors. In one embodiment, the controller 1096 may comprise a touch screen controller (e.g., a QT5480 touch screen controller available from Atmel) to control and manage the acquisition of touch data from a capacitive touch screen.

In certain embodiments, when the generator 1002 is in a "power off" state, the controller 1096 may continue to receive operating power (e.g., via a line from a power supply of the generator 1002, such as the power supply 2011 discussed below). In this way, the controller 196 may continue to monitor an input device 1045 (e.g., a capacitive touch sensor located on a front panel of the generator 1002) for turning the generator 1002 on and off. When the generator 1002 is in the power off state, the controller 1096 may wake the power supply (e.g., enable operation of one or more DC/DC voltage converters 2013 of the power supply 2011) if activation of the "on/off" input device 1045 by a user is detected. The controller 1096 may therefore initiate a sequence for transitioning the generator 1002 to a "power on" state. Conversely, the controller 1096 may initiate a sequence for transitioning the generator 1002 to the power off state if activation of the "on/off" input device 1045 is detected when the generator 1002 is in the power on state. In certain embodiments, for example, the controller 1096 may report activation of the "on/off" input device 1045 to the processor 1090, which in turn implements the necessary process sequence for transitioning the generator 1002 to the power off state. In such embodiments, the controller 196 may have no independent ability for causing the removal of power from the generator 1002 after its power on state has been established.

In certain embodiments, the controller 1096 may cause the generator 1002 to provide audible or other sensory feedback for alerting the user that a power on or power off sequence has been initiated. Such an alert may be provided at the beginning of a power on or power off sequence and prior to the commencement of other processes associated with the sequence.

In certain embodiments, the isolated stage 1052 may comprise an instrument interface circuit 1098 to, for example, provide a communication interface between a control circuit of a surgical device (e.g., a control circuit comprising handpiece switches) and components of the non-isolated stage 1054, such as, for example, the programmable logic device 1066, the DSP processor 1074 and/or the UI processor 190. The instrument interface circuit 1098 may exchange information with components of the non-isolated stage 1054 via a communication link that maintains a suitable degree of electrical isolation between the stages 1052, 1054, such as, for example, an infrared (IR)-based communication link. Power may be supplied to the instrument interface circuit 1098 using, for example, a low-dropout voltage regulator powered by an isolation transformer driven from the non-isolated stage 1054.

In one embodiment, the instrument interface circuit 198 may comprise a logic device 2000 (e.g., logic circuit, programmable logic circuit, PGA, FPGA, PLD) in communication with a signal conditioning circuit 2002. The signal conditioning circuit 2002 may be configured to receive a periodic signal from the logic circuit 2000 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical device control circuit (e.g., by using a conductive pair in a cable that connects the generator 102 to the surgical device) and monitored to determine a state or configuration of the control circuit. The control circuit may comprise a number of switches, resistors and/or diodes to modify one or more characteristics (e.g., amplitude, rectification) of the interrogation signal such that a state or configuration of the control circuit is uniquely discernable based on the one or more characteristics. In one embodiment, for example, the signal conditioning circuit 2002 may comprises an ADC for generating samples of a voltage signal appearing across inputs of the control circuit resulting from passage of interrogation signal therethrough. The logic device 2000 (or a component of the non-isolated stage 1054) may then determine the state or configuration of the control circuit based on the ADC samples.

In one embodiment, the instrument interface circuit 1098 may comprise a first data circuit interface 2004 to enable information exchange between the logic circuit 2000 (or other element of the instrument interface circuit 1098) and a first data circuit disposed in or otherwise associated with a surgical device. In certain embodiments, for example, a first data circuit 2006 may be disposed in a cable integrally attached to a surgical device handpiece, or in an adaptor for interfacing a specific surgical device type or model with the generator 1002. In certain embodiments, the first data circuit may comprise a non-volatile storage device, such as an electrically erasable programmable read-only memory (EEPROM) device. In certain embodiments and referring again to FIG. 19, the first data circuit interface 2004 may be implemented separately from the logic device 2000 and comprise suitable circuitry (e.g., discrete logic devices, a processor) to enable communication between the programmable logic device 2000 and the first data circuit. In other embodiments, the first data circuit interface 2004 may be integral with the logic device 2000.

In certain embodiments, the first data circuit 2006 may store information pertaining to the particular surgical device with which it is associated. Such information may include, for example, a model number, a serial number, a number of operations in which the surgical device has been used, and/or any other type of information. This information may be read by the instrument interface circuit 1098 (e.g., by the logic device 2000), transferred to a component of the non-isolated stage 1054 (e.g., to logic device 1066, DSP processor 1074 and/or UI processor 1090) for presentation to a user via an output device 1047 and/or for controlling a function or operation of the generator 1002. Additionally, any type of information may be communicated to first data circuit 2006 for storage therein via the first data circuit interface 2004 (e.g., using the logic device 2000). Such information may comprise, for example, an updated number of operations in which the surgical device has been used and/or dates and/or times of its usage.

As discussed previously, a surgical instrument may be detachable from a handpiece (e.g., instrument 1024 may be detachable from handpiece 1016) to promote instrument interchangeability and/or disposability. In such cases, conventional generators may be limited in their ability to recognize particular instrument configurations being used and to optimize control and diagnostic processes accordingly. The addition of readable data circuits to surgical device instruments to address this issue is problematic from a compatibility standpoint, however. For example, designing a surgical device to remain backwardly compatible with generators that lack the requisite data reading functionality may be impractical due to, for example, differing signal schemes, design complexity, and cost. Embodiments of instruments discussed herein address these concerns by using data circuits that may be implemented in existing surgical instruments economically and with minimal design changes to preserve compatibility of the surgical devices with current generator platforms.

Additionally, embodiments of the generator 1002 may enable communication with instrument-based data circuits. For example, the generator 1002 may be configured to communicate with a second data circuit contained in an instrument (e.g., instrument 1024 or 1034) of a surgical device. The instrument interface circuit 1098 may comprise a second data circuit interface 2010 to enable this communication. In one embodiment, the second data circuit interface 2010 may comprise a tri-state digital interface, although other interfaces may also be used. In certain embodiments, the second data circuit may generally be any circuit for transmitting and/or receiving data. In one embodiment, for example, the second data circuit may store information pertaining to the particular surgical instrument with which it is associated. Such information may include, for example, a model number, a serial number, a number of operations in which the surgical instrument has been used, and/or any other type of information. Additionally or alternatively, any type of information may be communicated to second data circuit for storage therein via the second data circuit interface 2010 (e.g., using the logic device 2000). Such information may comprise, for example, an updated number of operations in which the instrument has been used and/or dates and/or times of its usage. In certain embodiments, the second data circuit may transmit data acquired by one or more sensors (e.g., an instrument-based temperature sensor). In certain embodiments, the second data circuit may receive data from the generator 1002 and provide an indication to a user (e.g., an LED indication or other visible indication) based on the received data.

In certain embodiments, the second data circuit and the second data circuit interface 2010 may be configured such that communication between the logic device 2000 and the second data circuit can be effected without the need to provide additional conductors for this purpose (e.g., dedicated conductors of a cable connecting a handpiece to the generator 1002).

In one embodiment, for example, information may be communicated to and from the second data circuit using a 1-wire bus communication scheme implemented on existing cabling, such as one of the conductors used transmit interrogation signals from the signal conditioning circuit 2002 to a control circuit in a handpiece. In this way, design changes or modifications to the surgical device that might otherwise be necessary are minimized or reduced. Moreover, because different types of communications implemented over a common physical channel can be frequency-band separated, the presence of a second data circuit may be "invisible" to generators that do not have the requisite data reading functionality, thus enabling backward compatibility of the surgical device instrument.

In certain embodiments, the isolated stage 1052 may comprise at least one blocking capacitor 2096-1 connected to the drive signal output 1060*b* to prevent passage of DC current to a patient. A single blocking capacitor may be required to comply with medical regulations or standards, for example. While failure in single-capacitor designs is relatively uncommon, such failure may nonetheless have negative consequences. In one embodiment, a second blocking capacitor 2096-2 may be provided in series with the blocking capacitor 2096-1, with current leakage from a point between the blocking capacitors 2096-1, 2096-2 being monitored by, for example, an ADC 2098 for sampling a voltage induced by leakage current. The samples may be received by the logic circuit 2000, for example. Based changes in the leakage current (as indicated by the voltage samples in the embodiment of FIG. 19), the generator 1002 may determine when at least one of the blocking capacitors 2096-1, 2096-2 has failed. Accordingly, the embodiment of FIG. 19 provides a benefit over single-capacitor designs having a single point of failure.

In certain embodiments, the non-isolated stage 1054 may comprise a power supply 2011 for outputting DC power at a suitable voltage and current. The power supply may comprise, for example, a 400 W power supply for outputting a 48 VDC system voltage. The power supply 2011 may further comprise one or more DC/DC voltage converters 2013 for receiving the output of the power supply to generate DC outputs at the voltages and currents required by the various components of the generator 1002. As discussed above in connection with the controller 1096, one or more of the DC/DC voltage converters 2013 may receive an input from the controller 1096 when activation of the "on/off" input device 1045 by a user is detected by the controller 1096 to enable operation of, or wake, the DC/DC voltage converters 2013.

Having described operational details of various embodiments of the surgical systems 19 (FIG. 1), 190 (FIG. 10), 1000 (FIG. 16) operations for the above surgical systems 19, 190, 1000 may be further described generally in terms of a process for cutting and coagulating tissue employing a surgical instrument comprising an input device 406, 1009 and the generator 1002. Although a particular process is described in connection with the operational details, it can be appreciated that the process merely provides an example of how the general functionality described herein can be implemented by any one of the surgical systems 19, 190, 1000. Further, the given process does not necessarily have to be executed in the order presented herein unless otherwise indicated. As previously discussed, any one the input devices 406, 1009 may be employed to program the output (e.g., impedance, current, voltage, frequency) of the surgical devices 100 (FIG. 1), 120 (FIG. 10), 1002 (FIG. 16), 1006 (FIG. 16).

Figure 20:
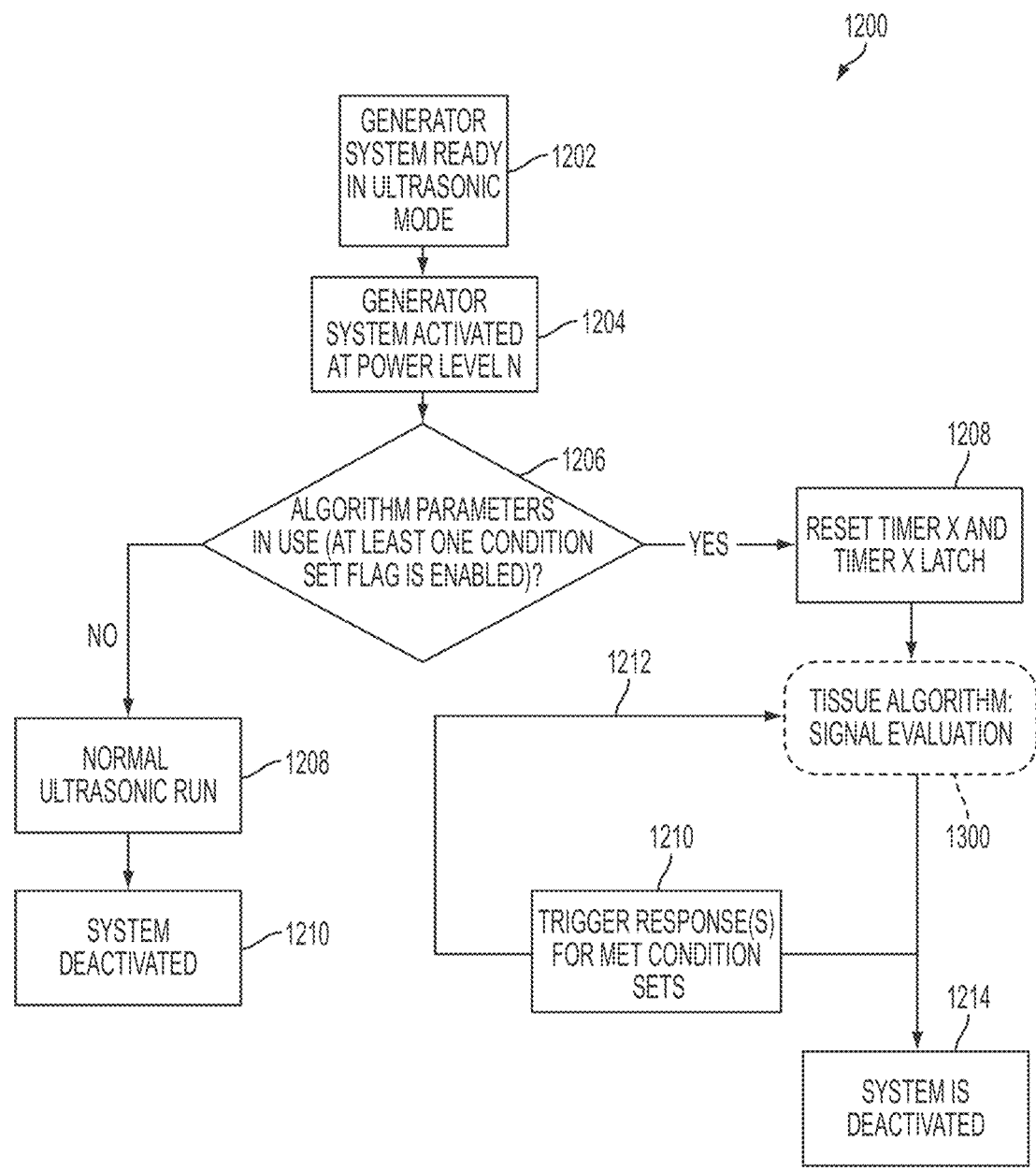
FIG. 20 is a logic flow diagram of a tissue algorithm that may be implemented in one embodiment of a generator.
Figure 21:
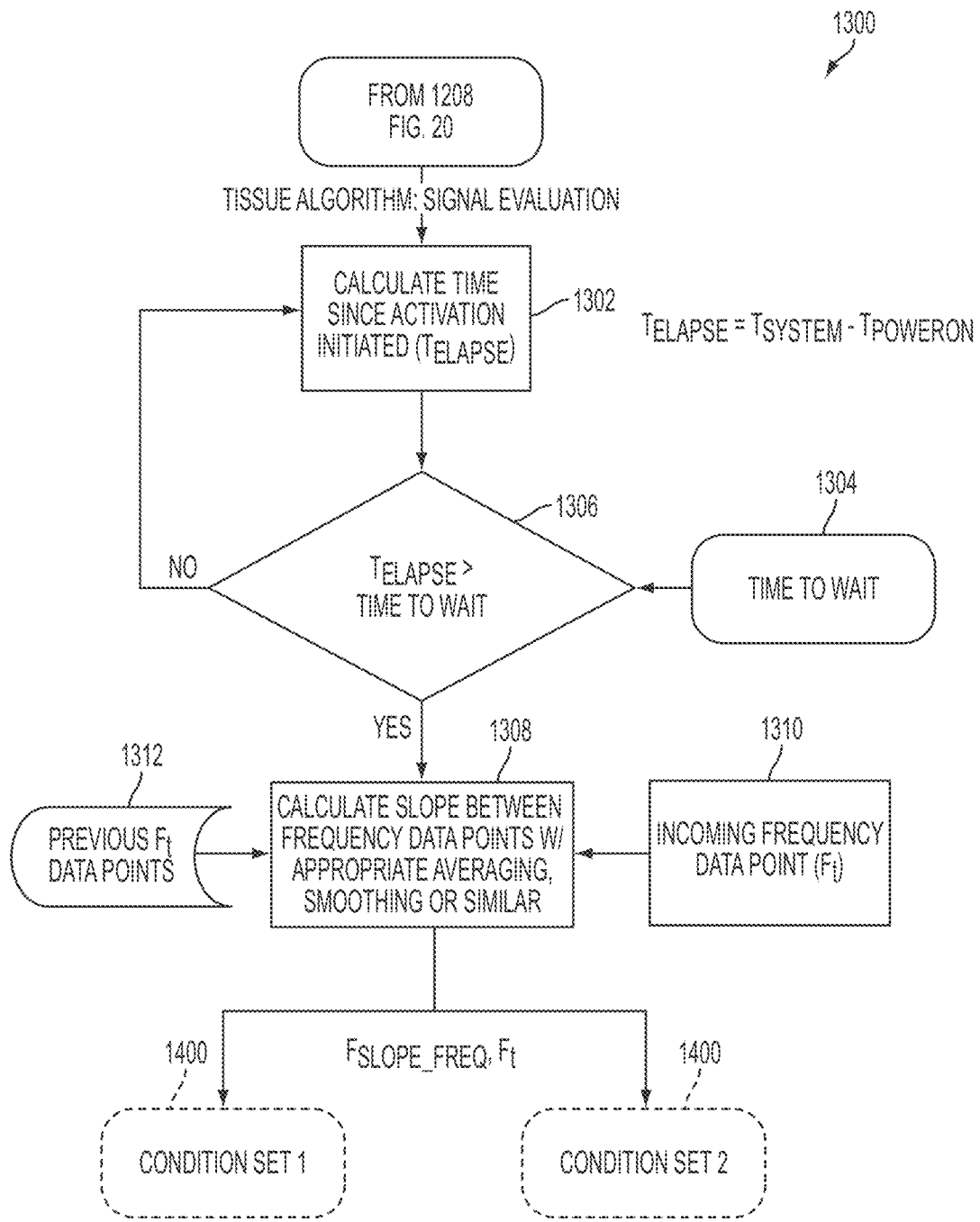
FIG. 21 is a logic flow diagram of a signal evaluation tissue algorithm portion of the tissue algorithm shown in FIG. 20 that may be implemented in embodiment of a generator.
Figure 22:
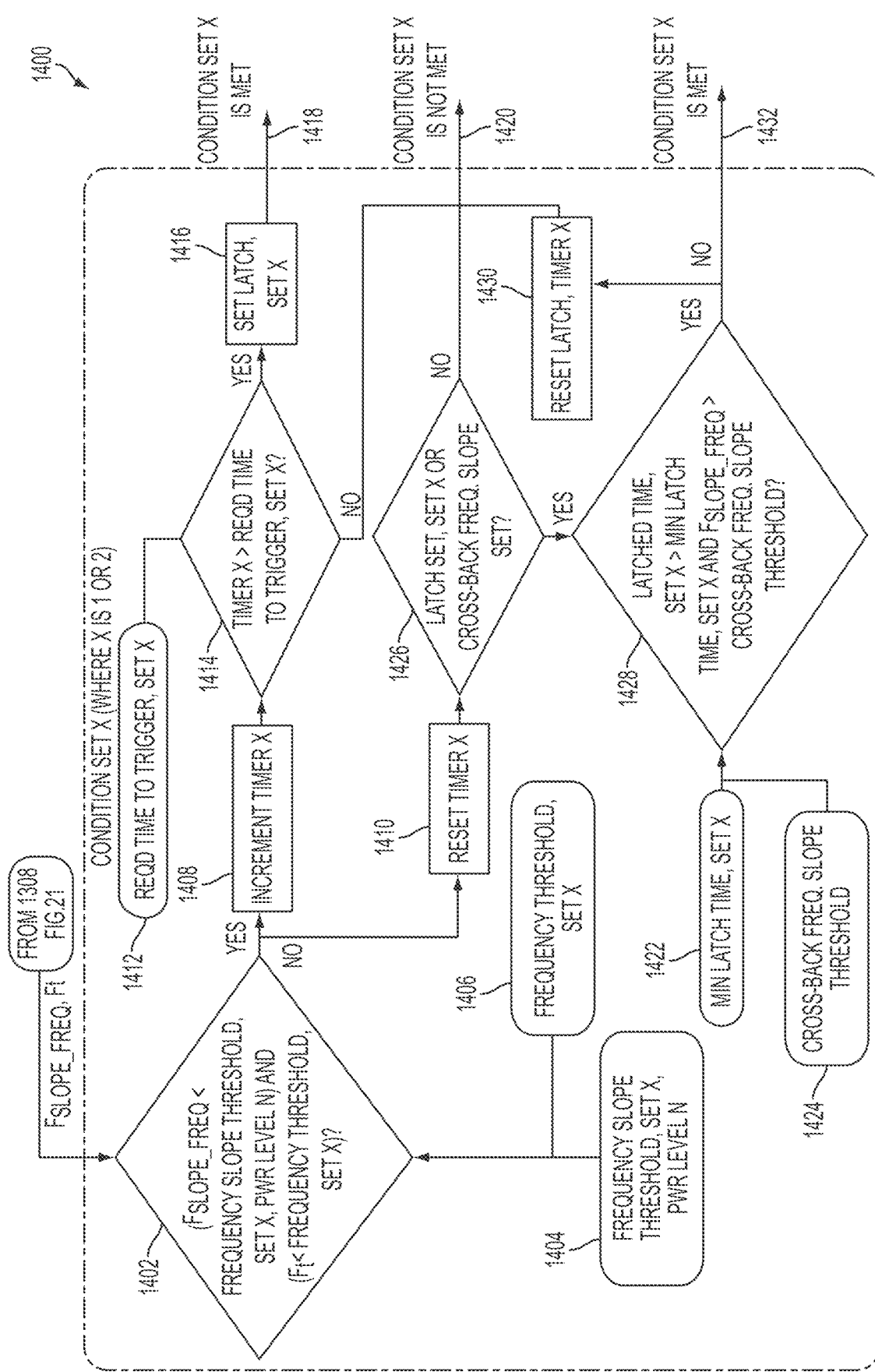
FIG. 22 is a logic flow diagram for evaluating condition sets for the signal evaluation tissue algorithm shown in FIG. 21 that may be implemented in one embodiment of a generator.

FIGS. 20-22 illustrate various embodiments of logic flow diagrams of 1200, 1300, 1400 related to a tissue algorithm for detecting when rapid heating of the ultrasonic end effector 1026 blade occurs and provide the opportunity for responding via the output indicator 412 (FIGS. 9, 11) and/or the output device 1047 (FIG. 16) (e.g., annunciation, modulation of power output and/or display of content). According to the present disclosure, when multiple reference numbers are used to described an element such as "ultrasonic surgical instrument 100, 120, 1004," it should be understood to reference any one of the elements, such as, for example, "ultrasonic surgical instrument 100," or "ultrasonic surgical instrument 120," or "ultrasonic surgical instrument 1004."

In various embodiments, feedback may be provided by the output indicator 412 shown in FIGS. 9 and 11 or the output device 1047 in FIG. 16. These feedback devices (e.g., output indicator 412, output device 1047) are particularly useful in applications where the tissue being manipulated by the end effector 81 (FIG. 1), 810 (FIG. 10), 1026 (FIG. 16) is out of the user's field of view and the user cannot see when a change of state occurs in the tissue. The feedback device communicates to the user that a change in tissue state has occurred as determined in accordance with the operations described with respect to the logic flow diagrams 700, 800, 900, 1200, 1300, 1400 as they relate to corresponding tissue algorithms. The feedback devices may be configured to provide various types of feedback according to the current state or condition of the tissue. A change of state of the tissue may be determined based on transducer and tissue measurements based on voltage, current, and frequency measurements in accordance with the operations described with respect to the logic flow diagrams 700, 800, 900 described above in connection with FIGS. 15A-C and the logic flow diagrams 1200, 1300, 1400 described below in connection with FIGS. 20-22.

In one embodiment, the logic flow diagrams 1200, 1300, 1400 may be implemented as executable modules (e.g., algorithms) comprising computer readable instructions to be executed by the processor 400 (FIGS. 9, 11, 14) portion of the generator 30, 500 or the generator 1002 (FIGS. 16, 17, 19). In various embodiments, the operations described with respect to the logic flow diagrams 1200, 1300, 1400 may be implemented as one or more than one software component, e.g., program, subroutine, logic; one or more than one hardware components, e.g., processor, DSP, PLD, PGA, FPGA, ASIC, circuit, logic circuit, register; and/or combinations of software and hardware. In one embodiment, the executable instructions to perform the operations described by the logic flow diagrams 1200, 1300, 1400 may be stored in memory. When executed, the instructions cause the processor 400, the DSP processor 1074 (FIG. 19) or logic device 1066 (FIG. 19) to determine a change in tissue state in accordance with the operations described in the logic flow diagrams 1200, 1300, and 1400 and provide feedback to the user by way of the output indicator 412 (FIGS. 9, 11) or output indicator 1047 (FIGS. 16, 17). In accordance with such executable instructions, the processor 400, DSP processor 1074, and/or logic device 1066 monitors and evaluates the voltage, current, and/or frequency signal samples available from the generator 30, 500, 1002 and according to the evaluation of such signal samples determines whether a change in tissue state has occurred. As further described below, a change in tissue state may be determined based on the type of ultrasonic instrument and the power level that the instrument is energized at. In response to the feedback, the operational mode of any one of the ultrasonic surgical instruments 100, 120, 1004 may be controlled by the user or may be automatically or semi-automatically controlled.

A brief summary of a tissue algorithm represented by way of the logic flow diagrams 1200, 1300, 1400 will now be described in connection with any one of the ultrasonic surgical instruments 100, 120, 1004 driven by a corresponding generator 30 (FIG. 1), 500 (FIG. 10), 1002 (FIG. 17). In one aspect, the tissue algorithm detects when the temperature of the blade portion (and therefore resonance) of the ultrasonic end effector 81 (FIG. 1), 810 (FIG. 10), 1026 (FIG. 17) is changing rapidly (of most interest is an increasing change). For a clamping or shears type instrument, this change may correspond to a common clinical scenario, among others, when minimal-to-no tissue, tissue debris or fluid is adjacent the blade and the blade is activated against the clamp arm, clamp pad or other suitable tissue biasing member. For non-clamping applications where an instrument with or without a clamp arm and associated mechanisms is used to effect tissue, this change corresponds to conditions where rapid heating occurs such as when the blade is activated against bone or other hard materials or when excessive force is used to couple the blade to tissue targets. These are illustrative cases; one can imagine other clinical scenarios where rapid blade heating may occur and such a tissue algorithm as described here is of benefit.

The tissue algorithm represented by the logic flow diagrams 1200, 1300, 1400 may be employed in conjunction with any of the generators 30, 500, 1002 described herein, and other suitable generators such as the GEN 04, GEN 11 generators sold by Ethicon Endo-Surgery, Inc. of Cincinnati, Ohio, and related devices, systems, that may leverage the algorithm or technology disclosed herein. Accordingly, in the description of the tissue algorithm in conjunction with the flow diagrams 1200, 1300, 1400 reference is made to the generators 30, 500, 1002 described in connection with corresponding FIGS. 1-9, 10-13, and 16-19.

Accordingly, with reference now to FIGS. 1-14, the frequency of the blade/handpiece resonant system of any one of the ultrasonic surgical instruments 100, 120, 1004 is dependent on temperature. When, for example, an ultrasonic shear type end effector cuts through a clamped piece of tissue, the blade heats and thins the tissue until ultimately it cuts through the tissue. At this point, the blade resides against the tissue pad and, if clamp pressure remains between the two, the blade and pad interface will draw power via the mechanical or vibratory motion of the blade relative to the pad. The power "deposited" at the interface will be largely conducted into the blade tip as the pad material is quite insulative. It is this thermal energy that alters the stiffness of the blade tip and the system resonance will change accordingly due to these localized (to the tip) conditions. The generator 30, 500, 1002 tracks this resonance. The shears example illustrates one scenario for which the algorithm is of use. Additional scenarios are back-cutting with a shears device with the clamp arm closed, blade cutting against tough or hard tissue, or any scenario in which knowing the thermal condition of the blade end-effector is desired. A tissue algorithm that applies logic to this tracking of resonance and, therefore, blade tip thermal condition is now described in connection with logic flow diagrams 1200, 1300, 1400 in FIGS. 20-22.

In addition, the description of the tissue algorithm described in connection with logic flow diagrams 1200, 1300, 1400 will be accompanied with illustrative examples via data obtained using any one of the ultrasonic surgical instruments 100, 120, 1004 comprising a corresponding generator 30, 500, 1002 described herein.

The tissue algorithm described in connection with logic flow diagrams 1200, 1300, 1400 relies on the monitoring of electrical drive signals, especially those correlating to the resonant frequency of the drive signal. The algorithm monitors the resonant frequency and its change with time (i.e., the first derivative of frequency with respect to time). Throughout this disclosure, this change in frequency with time is referred to as frequency slope. Frequency slope is calculated locally (from a time perspective) by calculating the change in frequency of adjacent (or relatively near) data points and dividing by the corresponding change in time. Because of signal transients, averaging or any of a multitude of applicable filtering or smoothing techniques (such that trends are more easily discernable and prevents turning on/off condition sets rapidly) may be employed. The data plots shown in FIGS. 62, 63, 64 illustrate the calculation of frequency slope and the use of averaging techniques (e.g., exponentially weighted moving average or EWMA) to obtain frequency slope values useful for control/monitoring. Other descriptions of frequency slope include, without limitation, "first derivative of frequency" and "frequency change with respect to time."

FIG. 20 is a logic flow diagram 1200 of a tissue algorithm that may be implemented in one embodiment of a generator 30, 500, 1002. At a general level, the tissue algorithm described in connection with logic flow diagram 1200 assesses the electrical signals in real time against a set of logic conditions that correlate to events of interest (e.g., blade of ultrasonic instrument is rapidly heating). Accordingly, the generator 30, 500, 1002 determines when a set of logic conditions occur and triggers a corresponding set of responses. The terms "Condition Set" and "Response set" are defined follows:

(1) Condition Set—a set of logic conditions that electrical signals are monitored against in real time.
(2) Response Set—one or more responses of the generator 30, 500, 1002 system to a Condition Set having been met.

At 1202, the generator 30, 500, 1002 is placed in an ultrasonic drive mode in a ready state.

At 1204, the generator 30, 500, 1002 is activated at a predetermined power level N. When the user activates the surgical system 19, 190, 1000, the corresponding generator 30, 500, 1002 responds by seeking the surgical system 19,

190, 1000 resonance and then ramping the output to the end effectors 81, 810, 1026 to the targeted levels for the commanded power level.

At 1206, the tissue algorithm determines whether parameters associated with the tissue algorithm are in use by determining when at least one Condition Sets/Response Sets flag is enabled. When no such flags are enabled, the algorithm proceeds along "NO" path where at 1208 the surgical system 19, 190, 1000 is operated in normal ultrasonic mode and at 1210, the corresponding generator 30, 500, 1002 is deactivated when the tissue procedure is completed.

When at least one flag for setting Condition Sets/Response Sets is enabled, the algorithm proceeds along "YES" path and the generator 30, 500, 1002 utilizes the tissue algorithm 1300 signal evaluation after resetting a Timer X and Timer X latch. In one embodiment, the at least one flag for setting Condition Sets/Response Sets may be stored in an EEPROM image of an instrument 100, 120, 1004 attached to the respective generator 30, 500, 1002. The EEPROM flags for setting the Condition Sets/Response Sets to an enabled state are contained in TABLE 1.

TABLE 1

| Enable/Disable Flag Functions for Tissue Algorithm | | Value to Enable Function | Value for "Normal" Drive |
|---|---|---|---|
| Name | Description | | |
| Condition Set 1 Pulsing flag | If Condition Set 1 is met and this function is enabled, the generator pulses power per the pulsing parameters as a part of Response Set 1 | 1 | 0 |
| Condition Set 1 LCD display flag | If Condition Set 1 is met and this function is enabled, the generator LCD displays an assigned graphics screen as part of Response Set 1 | 1 | 0 |
| Condition Set 1 Audio flag | If Condition Set 1 is met and this function is enabled, the generator plays an assigned audio file as part of Response Set 1 | 1 | 0 |
| Condition Set 2 Pulsing flag | If Condition Set 2 is met and this function is enabled, the generator pulses power per the pulsing parameters as a part of Response Set 2 | 1 | 0 |
| Condition Set 2 LCD display flag | If Condition Set 2 is met and this function is enabled, the generator LCD displays an assigned graphics screen as part of Response Set 2 | 1 | 0 |
| Condition Set 2 Audio flag | If Condition Set 2 is met and this function is enabled, the generator plays an assigned audio file as part of Response Set 2 | 1 | 0 |

In one embodiment, the tissue algorithm 1300 signal evaluation portion of the logic flow diagram 1200 utilizes two Condition Sets and each of these two Conditions Sets has a Response Set, which are described in more detail in connection with logic flow diagrams 1300, 1400. The tissue algorithm 1300 logic may be illustrated as follows: when Condition Set 1 is met, Response Set 1 is triggered. Having two condition sets enables a hierarchical response (differentiated responses based upon condition level) and also provides the ability to manage a complicated series of events.

At 1210, responses for Condition Sets that are met are triggered. Loop 1212 is repeated until the Condition Sets are met and the generator 30, 500, 1002 is deactivated at 1214.

The pulsing response is more detailed and requires further explanation than the relatively simple audio and LCD display responses. When a pulsing response is triggered, the generator 30, 500, 1002 drives a pulsed output as defined by the by the following four parameters:

(1) First Pulse Amplitude (EEPROM parameter, one value for each power level)—the drive amplitude for the first pulse;
(2) First Pulse Time (EEPROM parameter)—the time over which the first pulse amplitude is driven;
(3) Second Pulse Amplitude (EEPROM parameter, one value for each power level)—the drive amplitude for the second pulse; and
(4) Second Pulse Time (EEPROM parameter)—the time over which the second pulse amplitude is driven.

When driving a pulsed output, the generator 30, 500, 1002 drives the first pulse, then the second pulse and then repeats. The pulse amplitude may be expressed in units of: percentage of the commanded power level's output current. The commanded power level may be set by the activation switch (MIN or MAX) and the generator setting when MIN is activated.

FIG. 21 is a logic flow diagram 1300 of a signal evaluation tissue algorithm portion of the tissue algorithm shown in FIG. 20 that may be implemented in one embodiment of a generator. The tissue algorithm signal evaluation flow shown in FIG. 21 shows the application of a "time to wait" parameter 1304 and the calculation of a frequency slope (also referred to as local frequency slope because it is a running calculation).

At 1302, the algorithm calculates the time since activation was initiated at 1204 (FIG. 20). This time is expressed as $T_{Elapse}$, which is $T_{System} - T_{PowerOn}$. As previously discussed, when the user activates the surgical system 19, 190, 1000, the corresponding generator 30, 500, 1002 responds by seeking the resonance of the ultrasonic system 100, 120, 1004 and then ramping the output to the corresponding end effectors 81, 810, 1026 to the targeted levels for the commanded power level.

During this time, the associated signal transients can make the application of algorithm logic difficult. The algorithm, therefore, utilizes the "time to wait" parameter 1304 that is stored in the EEPROM image located in a hand piece portion of the ultrasonic surgical instrument 100, 120, 1004. The "time to wait" parameter 1304 (EEPROM parameter) is defined as the time at the beginning of an activation during which the generator 30, 500, 1002 does not apply the tissue algorithm to lessen the influence of resonance seek and drive ramp signal transients on algorithm logic. A typical "time to wait" parameter 1304 value is about 0.050 to 0.600 seconds (50 to 600 msec).

At 1306, $T_{Elapse}$ is compared to the "time to wait" parameter 1304 value. When $T_{Elapse}$ is less than or equal to the "time to wait" parameter 1304 value, the algorithm proceeds along "NO" path to calculate at 1302 a new $T_{Elapse}$. When $T_{Elapse}$ is greater than the "time to wait" parameter 1304 value, the algorithm proceeds along "YES" path to evaluate the signal.

At 1308, the algorithm performs the Signal Evaluation/Monitoring function. As previously stated, one aspect of the function algorithm is to monitor frequency slope. In a physical sense, frequency slope correlates to heat flux into or out of the resonant system comprising the blade and the handpiece acoustical subassembly, such as the ultrasonic systems 100, 120, 1004 disclosed herein. The changes in frequency and frequency slope during activation on tissue are dominated by the changing conditions occurring at the end-effector (tissue drying out, separating and blade contacting the clamp arm pad). When the blade is being heated (i.e., heat flux into the blade), the frequency slope is negative. When the blade is being cooled (i.e., heat flux out of the blade), the frequency slope is positive. Accordingly, the algorithm calculates the slope between frequency data points, i.e., incoming frequency data points 1310 ($F_t$) and previous $F_t$ data points 1312. The calculated frequency slope also may be referred to as a local frequency slope because it is a running calculation. The local frequency slope may be referred to as $F_{Slope\_Freq}$, $F_t$, which is the frequency slope ($F_{Slope\_Freq}$) at the resonance frequency ($F_t$). The local frequency slope may be routed to a Condition Set 1, Condition Set 2 1400, for example, for evaluation in accordance with the flow diagram 1400 shown in FIG. 22.

FIG. 22 is a logic flow diagram 1400 for evaluating condition sets for the signal evaluation tissue algorithm shown in FIG. 21 that may be implemented in one embodiment of a generator. The logic flow diagram 1400 evaluates Condition Set X, where X is either 1 or 2, for example.

In accordance with the tissue algorithm, at 1402, the local frequency slope calculated at 1308 (FIG. 21) is compared against a frequency slope threshold parameter 1404 value for Condition Set X at Power Level N. The frequency slope threshold parameters 1404 may be stored in an EEPROM located in the attached instrument 100, 120, 1004, where one EEPROM parameter value is stored for each power level. When the local frequency slope calculated at 1308 drops below the frequency slope threshold parameter 1404 value, a first Response Set may be triggered at 1210 (FIG. 20). When the blade is being heated at a relatively rapid rate, the frequency slope will become more negative and the tissue algorithm identifies this condition by way of the frequency slope dropping below the frequency slope threshold parameter 1404 value. Again, the frequency slope indicates the rate of thermal change or heat flux into or out of the blade.

In accordance with the tissue algorithm, also at 1402, the resonant frequency is compared against a frequency threshold parameter 1406 value for Condition set X. The frequency threshold parameter 1406 value may be stored in an EEPROM located in the attached instrument 100, 120, 1004. When the resonant frequency drops below the threshold frequency parameter 1406 value, a second Response Set may be triggered at 1210 (FIG. 20). As a blade is continually heated, the frequency will continue to drop. A frequency threshold parameter 1406 value is intended to improve algorithm robustness by providing additional information about the thermal condition of the blade (in addition to the more dynamic indicator, the frequency slope). Frequency drop from some known condition such as room temperature gives a good indication of the thermal state of the resonant system relative to these known thermal conditions.

At 1402, when the frequency slope ($F_{Slope\_Freq}$) is less than the frequency slope threshold parameter 1404 value and the resonant frequency ($F_t$) is less than the frequency threshold parameter 1406 value, the algorithm proceeds along "YES" path to 1408 to increment a Timer X (where X corresponds to the particular Condition Set being evaluated by the tissue algorithm).

In comparing the electrical signals, e.g., the frequency slope ($F_{Slope\_Freq}$) and the resonant frequency ($F_t$), against respective thresholds parameters 1404, 1406, borderline conditions where the signal bounces back-and-forth across the threshold can be taken into consideration as follows. In one aspect, the tissue algorithm employs a "required time before trigger" parameter 1412 value (which also may be stored in the instrument EEPROM) for the particular Condition Set X to account for this consideration. The "required time before trigger" parameter 1412 value is defined as the time required before trigger (EEPROM parameter)—required time for frequency slope and/or frequency to be less than their respective thresholds for a Response Set to be triggered. This is intended to prevent rapid "back and forth" triggering of a response. It may be useful, however, to track non-rapid "back and forth" triggering, which may occur.

Thus, at 1414 the algorithm determines whether the Timer X value is greater than the "required time before trigger" parameter 1412 value for Condition Set X. When the Timer X value is greater than the "required time before trigger" parameter 1412 value, the algorithm proceeds along "YES" path to set a latch for Condition Set X at 1416. Output 1418 indicates that the Condition Set X is met. When the Timer X value is less than or equal to the "required time before trigger" parameter 1412 value, the algorithm proceeds along "NO" path to indicate at output 1420 that the Condition Set X is not met.

At 1402, when either the frequency slope ($F_{Slope\_Freq}$) is greater than or equal to the frequency slope threshold parameter 1404 value or the resonant frequency ($F_t$) is greater than then or equal to the frequency threshold parameter 1406 value, the algorithm proceeds along "NO" path to reset the Timer X at 1410 (where X corresponds to the particular Condition Set being evaluated by the tissue algorithm).

For additional robustness, two latching parameters are employed by the algorithm. Without the use of latching, the algorithm is configured to end a response set when either (a) the system is deactivated or (b) when the signal or signals are no longer below their respective thresholds. Two latching parameters can be utilized. They are a "minimum latch time" parameter 1422 and a "cross-back frequency slope threshold" parameter 1424. These latch parameters 1422, 1424 are important for robustness around: (a) clamp arm pad surfaces that become more lubricious with elevated temperature and (b) pulsing output where signal transients at the pulse transitions are expected.

The minimum latch time parameter 1422 (EEPROM parameter) can be defined as the minimum amount of time for response(s) to a Condition Set X to be triggered. Considerations for minimum latch time include: (a) the length of time required to play a triggered audible response (e.g., in one embodiment, a "pre-alert" WAV audio file may be about 0.5 seconds long), (b) the typical (about 0.5 to 1.0 sec) or extreme (about 1.5 to 2.0 sec) user response times for an event, or (c) the typical tissue re-grasp time for a multi-cut (known as "marching") application (about 1.1-2.0 seconds with a mean of about 1.6 seconds).

The cross-back frequency slope threshold parameter 1424 (EEPROM parameter) can be defined as the frequency slope threshold above which a triggered response stops (i.e., is no longer triggered). This provides for a higher "cross-backover" frequency slope threshold that is tasked with distinguishing between activating against the pad and jaw opened (versus distinguishing between activating on tissue and activating on the pad).

In accordance with the tissue algorithm portion represented by logic flow diagram 1400, after the Timer X is reset at 1410, at 1426, the tissue algorithm determines whether either the latch for Condition Set X or the Cross-back Frequency Slope Latch is set. When both latches are not set, the algorithm proceeds along "NO" to indicate at output 1420 that the Condition Set X is not met. When either one of the latches is set, the algorithm proceeds along "YES" path to 1428.

At 1428, the algorithm determines whether the Latched Time for Condition Set X is greater than the minimum latch time parameter 1422 value for Condition Set X and whether the frequency slope ($F_{Slope\_Freq}$) is greater than the cross-back frequency slope threshold parameter 1424 value the algorithm proceeds along "YES" path to reset the Latch for Timer X at 1430 and to indicate at output 1420 that the Condition Set X is not met. When the Latched Time for Condition Set X is less than or equal to the minimum latch time parameter 1422 value for Condition Set X and the frequency slope ($F_{Slope\_Freq}$) is less than or equal to the cross-back frequency slope threshold parameter 1424 value the algorithm proceeds along "NO" path to indicate at output 1432 that the Condition Set X is met.

As shown in FIGS. 21 and 22, there are two identical Condition Sets 1 and 2 from a flow perspective. These Conditions Sets 1 and 2 have replicate sets of parameters as contained in TABLE 2. Algorithm parameters that are shared by the Condition Sets 1 and 2 are contained in TABLE 3.

TABLE 2 contains a summary of the replicated algorithm EEPROM parameters for each of the Condition Sets and the number parameters per Condition Set.

TABLE 2

Algorithm EEPROM Parameter Summary, Replicated Parameters for Each of the Condition Sets

| Replicated Parameters for Each of the Condition Sets | # of Parameters per Condition Set |
|---|---|
| Required time before triggered | 1 |
| Minimum latch time | 1 |
| Frequency Slope Thresholds (one for each power level) | 5 |
| Frequency Threshold | 1 |

TABLE 3 contains a summary of the shared algorithm EEPROM parameters for each of the Condition Sets (not replicated) and the number parameters.

TABLE 3

Algorithm EEPROM Parameter Summary, Common Parameters to all Condition Sets

| Parameters Shared by Condition Sets (not replicated) | # of Parameters |
|---|---|
| Time to wait | 1 |
| Cross-back Frequency Slope Threshold | 1 |
| First Pulse Amplitudes (one for each power level) | 5 |
| First Pulse Time | 1 |
| Second Pulse Amplitudes (one for each power level) | 5 |
| Second Pulse Time | 1 |

Figure 27:
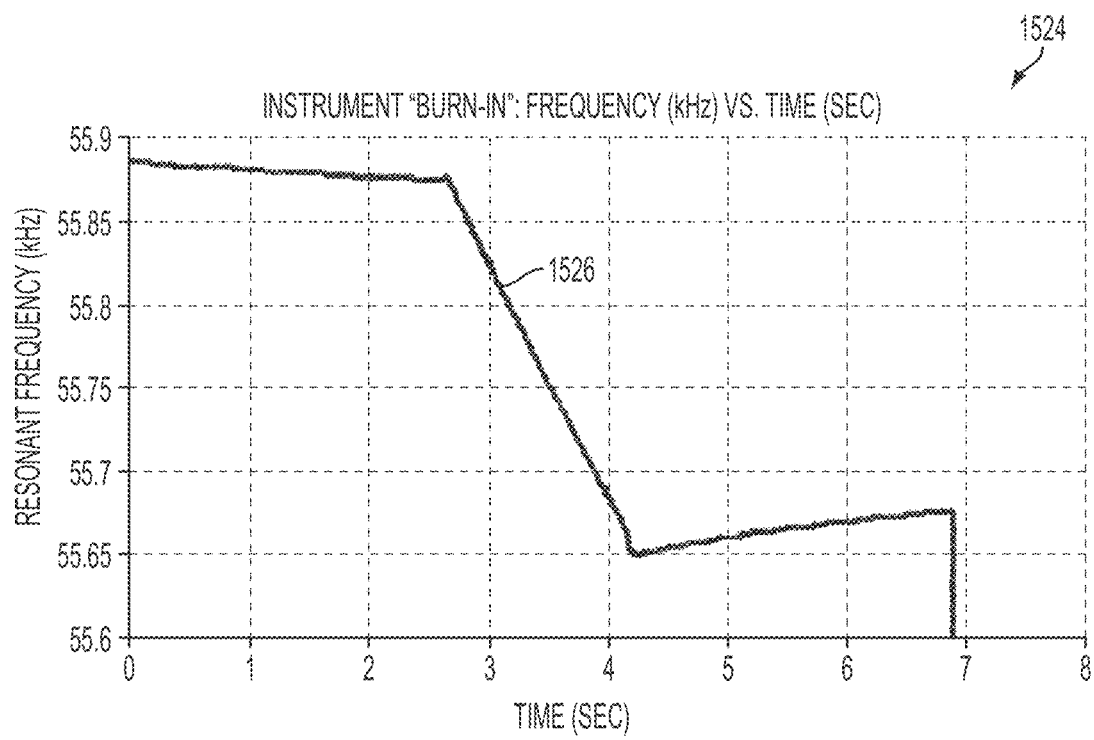
FIG. 27 is a graphical representation of frequency versus time waveform of one embodiment of a generator during a burn-in test as it relates to the graphical representation shown in FIG. 26.
Figure 28:
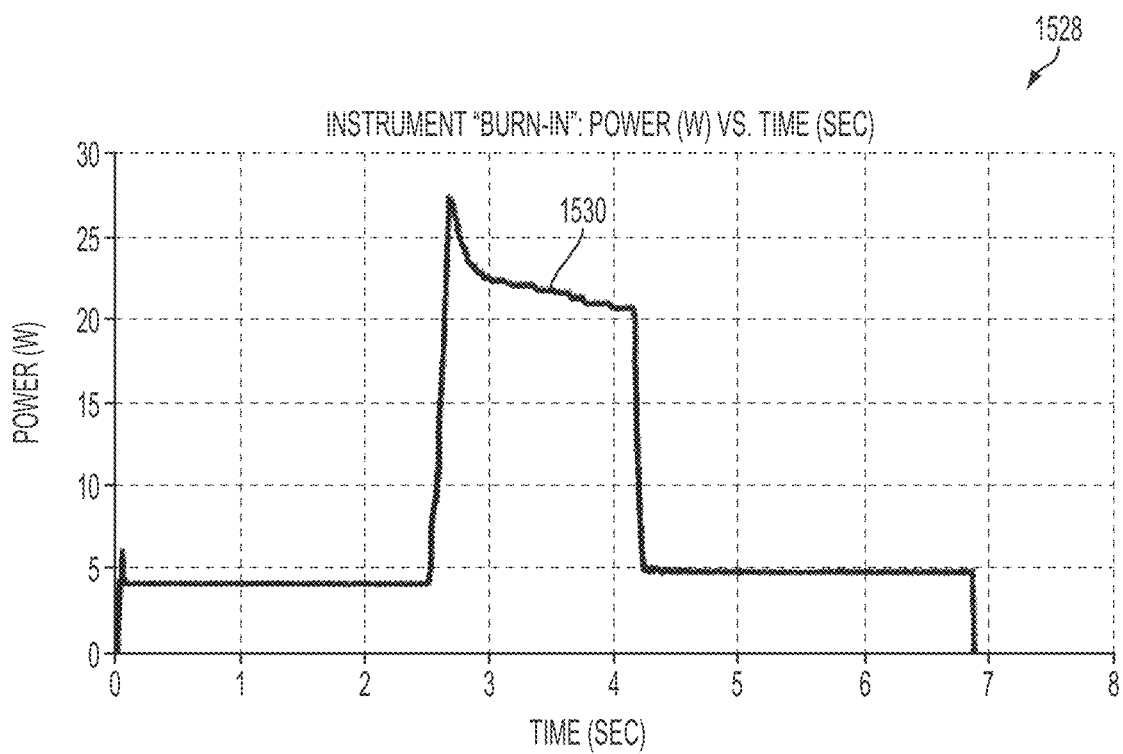
FIG. 28 is a graphical representation of power consumption versus time waveform of one embodiment of a generator during a burn-in test as it relates to the graphical representation shown in FIG. 26.
Figure 29:
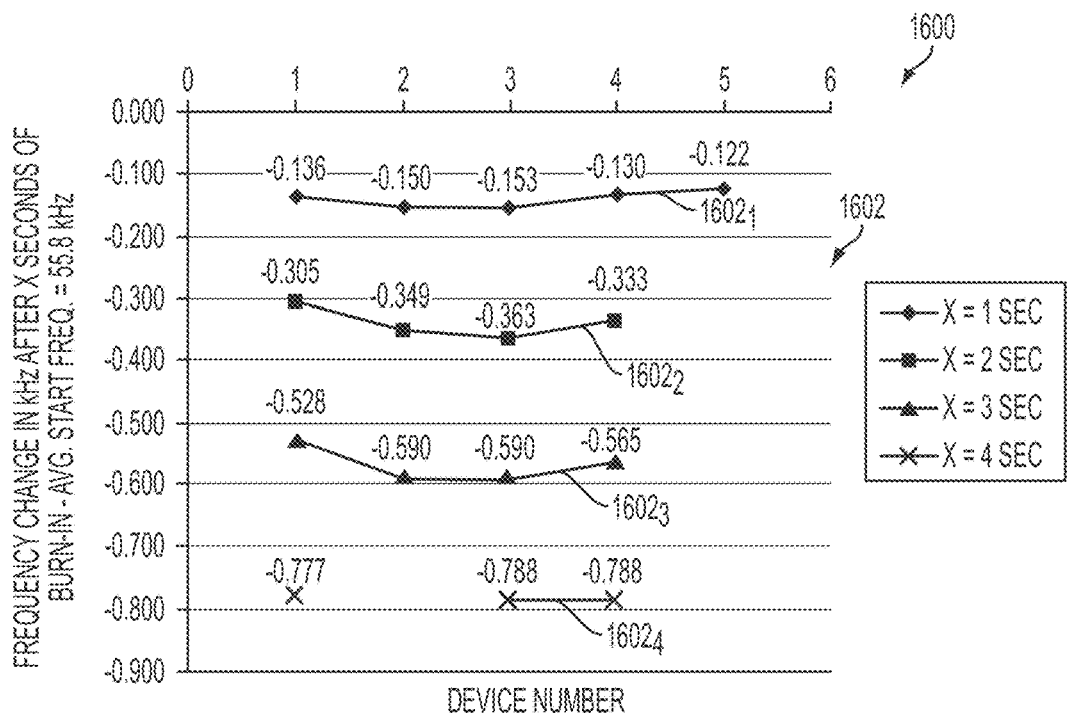
FIG. 29 is a graphical representation of frequency change over time waveform of several generator/instrument combinations during burn-in tests.
Figure 30:
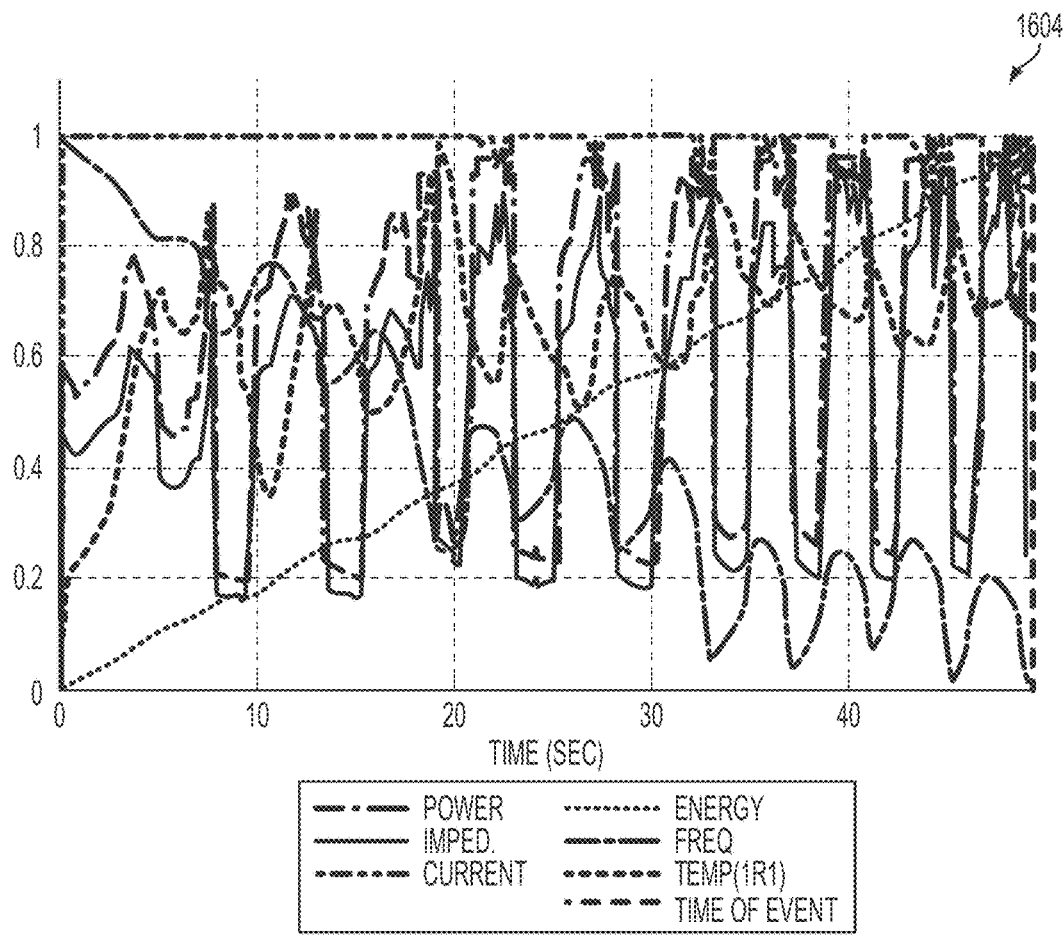
FIG. 30 is a graphical representation of normalized combined impedance, current, frequency, power, energy, and temperature waveforms of one embodiment of a generator coupled to an ultrasonic instrument to make 10 successive cuts on excised porcine jejunum tissue as quickly as possible while keeping the generator running throughout.
Figure 32:
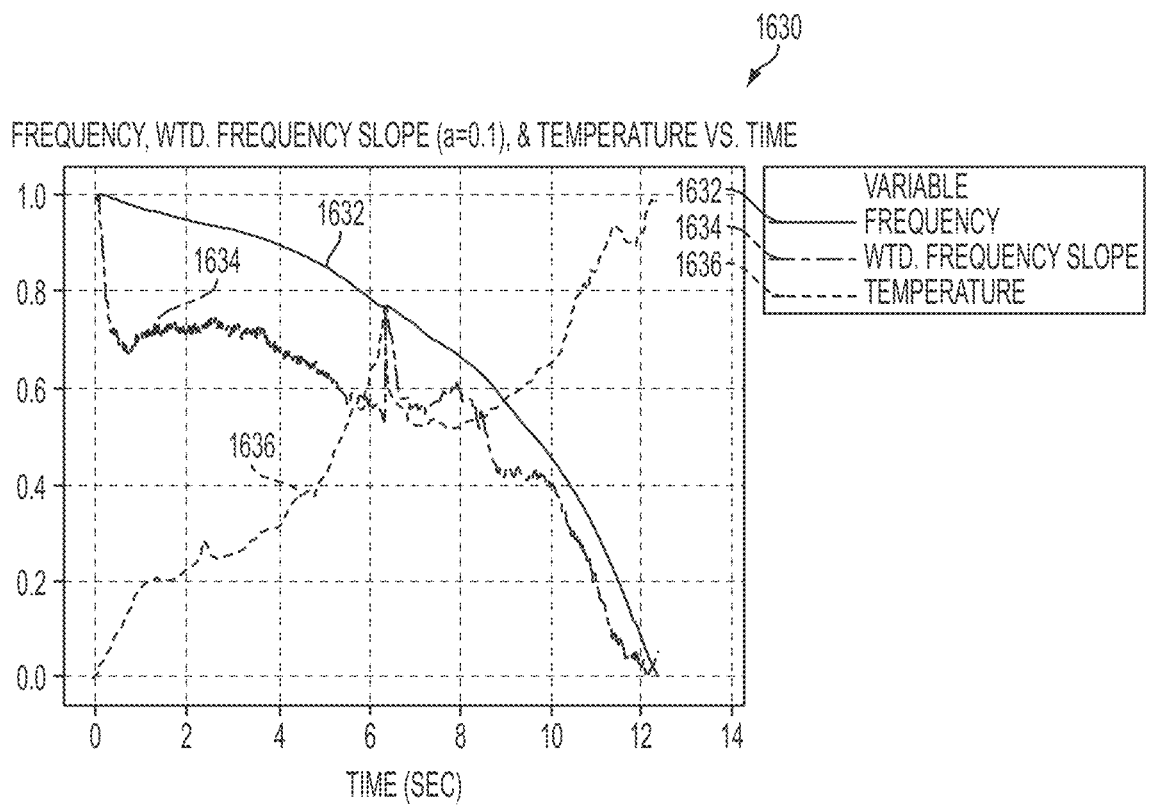
FIG. 32 is a combined graphical representation of frequency, weighted frequency slope waveform calculated via exponentially weighted moving average with an alpha value of 0.1, and temperature versus time waveform of one embodiment of a generator.
Figure 33:
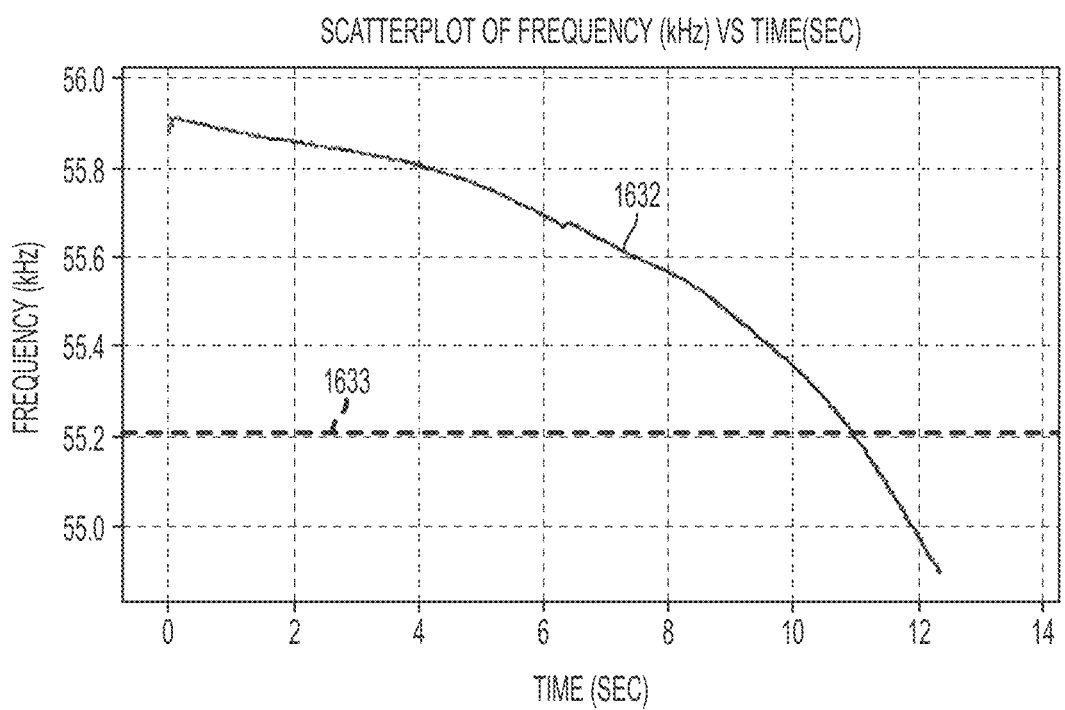
FIG. 33 is a graphical representation of a frequency versus time waveform shown in FIG. 32.
Figure 34:
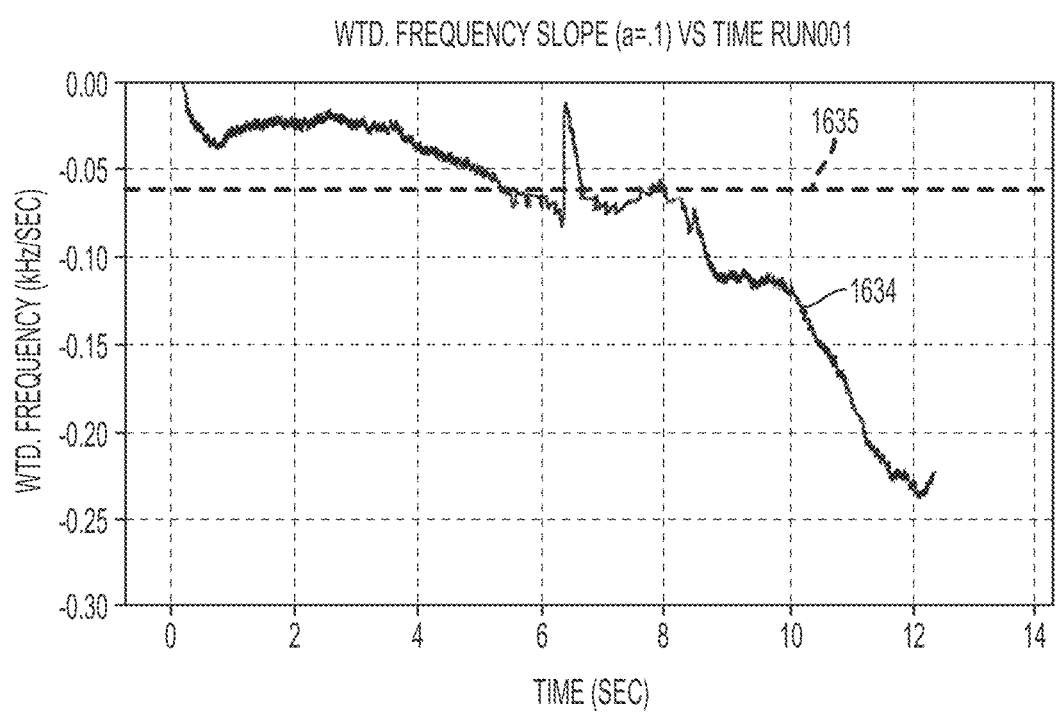
FIG. 34 is a graphical representation of the weighted frequency slope versus time waveform shown in FIG. 32.

For clarity of disclosure, the tissue algorithm described in connection with the logic flow diagrams 1200, 1300, 1400 shown in respective FIGS. 20-22 will now be described in terms of four examples. The basic application of the tissue algorithm includes the monitoring of frequency slope, resonant frequency, or both against their respective thresholds. Accordingly, a first example includes the monitoring of frequency slope against its respective threshold and is illustrated in FIGS. 23-28. A second example includes the monitoring of resonant frequency against its respective threshold and is illustrated in FIGS. 29-31. A third example includes the monitoring both the frequency slope and the resonant frequency, against their respective threshold and is illustrated in FIGS. 32-34. Finally, a fourth example also includes the monitoring both of the frequency slope and the resonant frequency, against their respective threshold.

Example 1: Monitoring Frequency Slope Against Respective Threshold

A first example case includes the monitoring of frequency slope against a respective threshold is illustrated with reference to FIGS. 23-28. The first example, and most simple, is the example of triggering a Response Set based only on the frequency slope. TABLE 4 contains representative parameters for this objective for surgical instruments such as any one of the surgical instruments 19, 190, 1000 disclosed herein comprising a corresponding ultrasonic instrument such as ultrasonic instruments 100, 120, 1004 disclosed herein.

TABLE 4

Representative Parameters for Triggering an Audio Indication by Frequency Slope Threshold Only (one Condition Set utilized)

| Parameter | Value* |
|---|---|
| Condition Set 1 Pulsing flag | 0 |
| Condition Set 1 LCD display flag | 0 |
| Condition Set 1 Audio flag | 1 |
| Required time before triggered, Condition Set 1 | 50 msec |
| Minimum latch time, Condition Set 1 | 0 msec* |
| Frequency Slope Thresholds (one for each power level), Condition Set 1 | level 5: −0.060 kHz/sec<br>level 4: −0.053 kHz/sec<br>level 3: −0.045 kHz/sec<br>level 2: −0.038 kHz/sec<br>level 1: −0.030 kHz/sec |
| Frequency Threshold, Condition Set 1 | 56,000 Hz* |
| Time to wait | 100 msec |
| Cross-back Frequency Slope Threshold | −0.020 kHz/sec |
| First Pulse Amplitudes (one for each power level) | N/A |
| First Pulse Time | N/A |
| Second Pulse Amplitudes (one for each power level) | N/A |
| Second Pulse Time | N/A |

*These parameter values are set to an appropriate extreme such that they do not effectively take part in the logic flow (e.g., set to always be "true").

Figure 23:
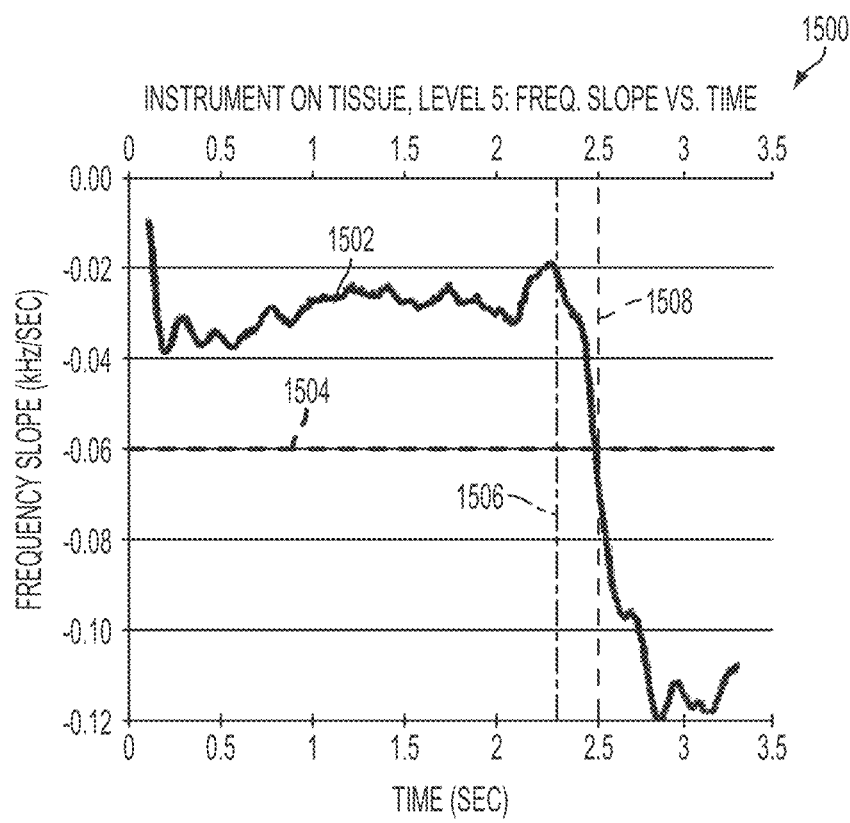
FIG. 23 is a graphical representation of frequency slope (first time derivative of frequency) versus time waveform of one embodiment of a generator during a typical tissue cut.
Figure 24:
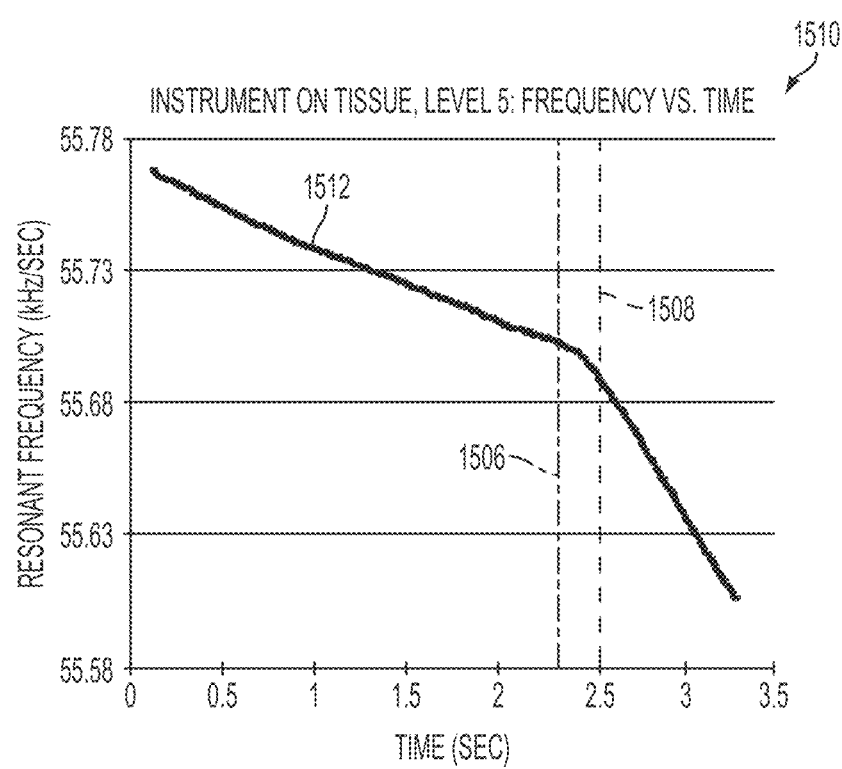
FIG. 24 is a graphical representation of frequency versus time waveform of one embodiment of a generator during a typical tissue cut as it relates to the graphical representation shown in FIG. 23.
Figure 25:
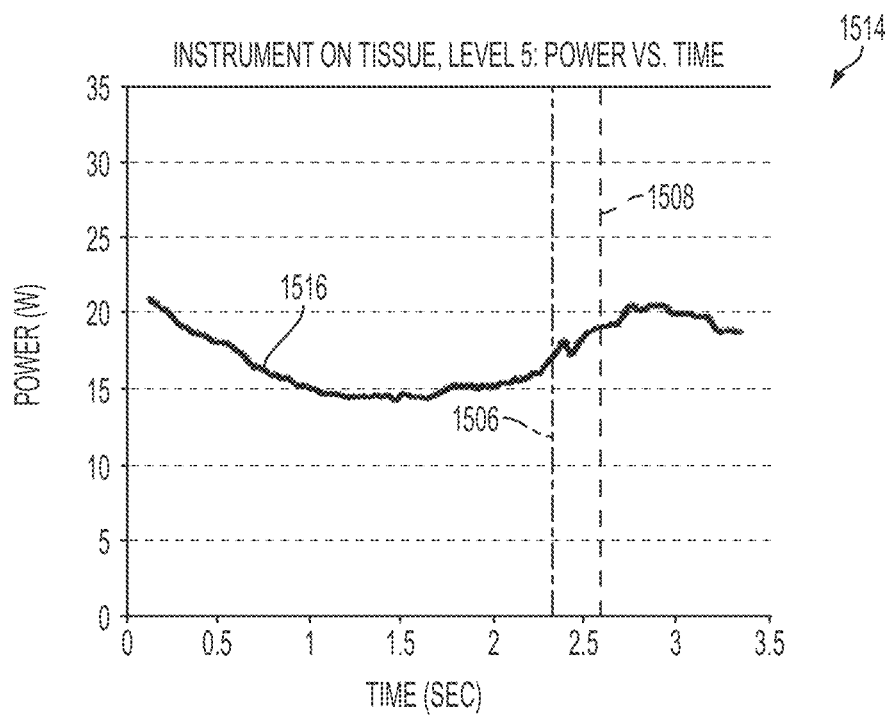
FIG. 25 is a graphical representation of drive power versus time waveform of one embodiment of a generator during a typical tissue cut as it relates to the graphical representation shown in FIG. 23.

FIGS. 23-25 show signal data produced by a generator with the representative/illustrative parameters contained in TABLE 4. The generator may be similar to any one of the generators 30, 500, 1002 disclosed herein, which forms a portion of the respective surgical systems 19, 190, 1000 operating in ultrasonic mode (e.g., ultrasonic system 19, 190, 1000) applied on tissue in accordance with the present disclosure.

Figure 26:
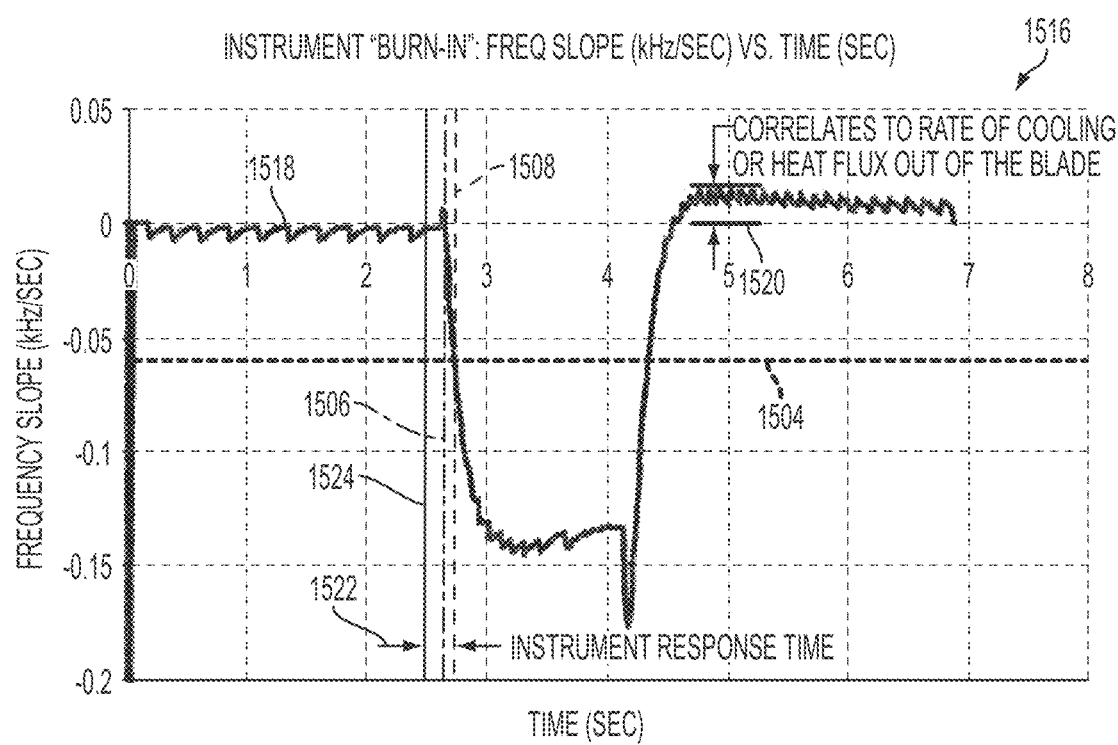
FIG. 26 is a graphical representation of frequency slope versus time waveform of one embodiment of a generator during a burn-in test.

The use of only the frequency slope to trigger a Response Set may be further demonstrated in the "burn-in" scenario or test. FIGS. 26-28 show signal data produced by a generator with the representative/illustrative parameters contained in TABLE 4 during a "burn-in" scenario or test. A "burn-in" simulates the use case where a user activates a shears type ultrasonic surgical instrument without intervening tissue (e.g., back-cutting with jaws closed). This test also may be useful for quantifying device characteristics, such as, for example, "response time."

The response time of an ultrasonic instrument may be defined as the time required for an ultrasonic system (instrument, handpiece, and generator with tissue algorithm) to respond to the clamp arm pad coming into contact with the blade. The ultrasonic system is usually initially activated "in-air" (i.e., unloaded), the clamp arm is closed against the blade and held for a period of time and then the clamp arm is opened and the ultrasonic system is deactivated. The response time is the time between the point at which the quiescent power (power in-air) begins to change due to the clamp arm pad initiating contact with the blade and the point at which the Response Set is triggered. This is also a test that enables quantification of the rate of cooling—the higher the rate of cooling (assuming similar convective boundary conditions) the more thermal energy or residual heat there is in the blade. The rate of cooling is proportional to the frequency slope (to reinforce: a positive frequency slope value correlates to the instantaneous heat flux out of the blade). As will be detailed later, the rate of cooling also may be monitored and used for control purposes so that, for example, if the rate of cooling as defined by a positive frequency slope is greater than a threshold value, one knows that the blade is "carrying" a large amount of thermal energy and is dissipating it rapidly.

FIG. 23 is a graphical representation 1500 of frequency slope versus time of a waveform 1502 of one embodiment of a generator during a typical tissue cut. Frequency slope (kHz/sec) is shown along the vertical axis and time (Sec) is shown along the horizontal axis for a typical tissue cut using any one of the ultrasonic systems comprising corresponding ultrasonic surgical instruments set on power level 5. The frequency slope threshold 1504 used for this application was −0.06 kHz/sec and is shown by the horizontal dashed line. The vertical dash-dot line 1506 shows the time (2.32 seconds) that the tissue began to separate, and the vertical dashed line 1508 shows the time (2.55 seconds) at which the ultrasonic system triggered a Response Set (in this case, per TABLE 4, an audible sound only).

Figure 23A:
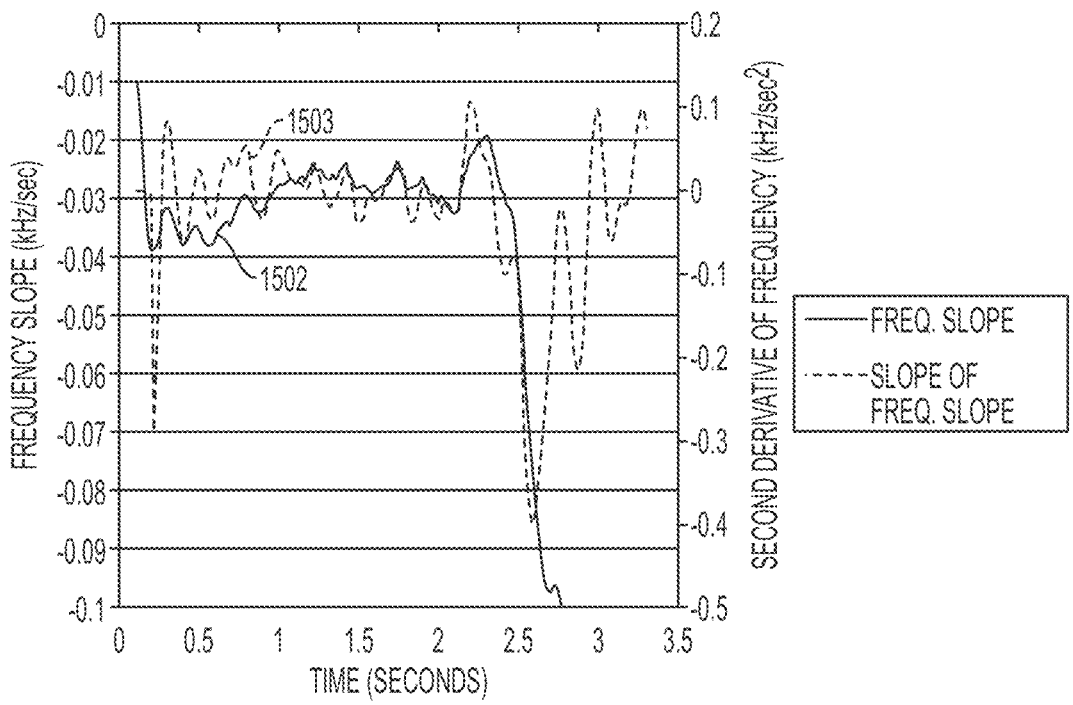
FIG. 23A is a graphical representation of slope of frequency slope (second time derivative of frequency) versus time waveform shown in dashed line superimposed over the waveform shown in FIG. 23 of one embodiment of a generator during a typical tissue cut.

FIG. 23A is a graphical representation of a second time derivative of frequency (slope of frequency slope) versus time waveform 1503 (shown in dashed line) superimposed over the waveform 1502 shown in FIG. 23 of one embodiment of a generator during a typical tissue cut.

FIG. 24 is a graphical representation 1510 of frequency versus time waveform 1512 of one embodiment of a generator during a typical tissue cut as it relates to the graphical representation 1500 shown in FIG. 23. Resonant frequency (kHz) is shown along the vertical axis and time (Sec) is shown along the horizontal axis for the typical tissue cut using any one of the ultrasonic systems set on power level 5. The vertical dash-dot line 1506 shows the time (2.32 seconds) that the tissue began to separate, and the vertical dashed line 1508 shows the time (2.55 seconds) at which the ultrasonic system triggered a Response Set (in this case, an audible sound only).

FIG. 25 is a graphical representation 1514 of power consumption versus time waveform 1514 of one embodiment of a generator during a typical tissue cut as it relates to the graphical representation 1500 shown in FIG. 23. Power (W) is shown along the vertical axis and time (Sec) is shown along the horizontal axis for the typical tissue cut using any one of the ultrasonic systems set on power level 5. The vertical dash-dot line 1506 shows the time (2.32 seconds) that the tissue began to separate, and the vertical dashed line 1508 shows the time (2.55 seconds) at which the ultrasonic system triggered a Response Set (in this case, an audible sound only).

FIG. 26 is a graphical representation 1516 of frequency slope versus time waveform 1518 of one embodiment of a generator during a burn-in test. The parameters for this test are consistent with those contained in TABLE 4. Frequency slope (kHz/sec) is shown along the vertical axis and time (Sec) is shown along the horizontal axis for a typical tissue cut using any one of the ultrasonic systems set on power level 5. The frequency slope threshold 1504 used for this application was −0.06 kHz/sec as is shown by the horizontal dashed line. The vertical dotted line 1524 shows the point in time (2.49 seconds) that the quiescent power begins to change due to clamping, the vertical dash-dot line 1506 shows the time (2.66 seconds) at which power has completed ramp-up, and the vertical dashed line 1508 shows the time (2.72 seconds) that the ultrasonic system triggered a Response Set (in this case, an audible sound only). As shown in the graphical representation 1516, the frequency slope at 1520 correlates to the rate of cooling or heat flux out of the blade. Also, the response time 1522 of the ultrasonic system is measured as the time lapse between the point in time (2.49 seconds) that the quiescent power begins to change due to clamping and the time (2.72 seconds) that the ultrasonic system triggered a Response Set.

FIG. 27 is a graphical representation 1524 of a frequency versus time waveform 1526 of one embodiment of a generator during a burn-in test as it relates to the graphical representation 1516 shown in FIG. 26. Resonant frequency (kHz) is shown along the vertical axis and time (Sec) is shown along the horizontal axis for the typical tissue cut using any one of the ultrasonic systems set on power level 5.

FIG. 28 is a graphical representation 1528 of a power consumption versus time waveform 1530 of one embodiment of a generator during a burn-in test as it relates to the graphical representation 1516 shown in FIG. 26. Power (W) is shown along the vertical axis and time (Sec) is shown along the horizontal axis for the typical tissue cut using any one of the ultrasonic systems set on power level 5.

Example 2: Triggering a Response Set Based Only on the Frequency Threshold

A second example case includes triggering a Response Set based only on the frequency threshold with reference to FIGS. 29-35. TABLE 5 contains representative parameters for this objective in connection with surgical instruments such as any one of the surgical instruments 19, 190, 1000 disclosed herein comprising corresponding ultrasonic instruments such as the ultrasonic instrument 100, 120, 1004 disclosed herein. It will be appreciated that triggering via frequency threshold may be of limited utility as it is less indicative of dynamic end-effector conditions and is presented herein for completeness of disclosure. The inclusion of frequency slope in the tissue algorithm discussed in connection with logic flow diagrams 1200, 1300, 1400 is intended for use in combination logic (combined with use of the frequency slope threshold) which is covered in the next section of this specification.

TABLE 5

Representative Parameters for Triggering an Audio Indication by Frequency Threshold Only (one Condition Set utilized)

| Parameter | Value* |
| --- | --- |
| Condition Set 1 Pulsing flag | 0 |
| Condition Set 1 LCD display flag | 0 |
| Condition Set 1 Audio flag | 1 |
| Required time before triggered, Condition Set 1 | 50 msec |
| Minimum latch time, Condition Set 1 | 0 msec* |
| Frequency Slope Thresholds (one for each power level), Condition Set 1 | level 5: 1.00 kHz/sec* |
| | level 4: 1.00 kHz/sec* |
| | level 3: 1.00 kHz/sec* |

TABLE 5-continued

Representative Parameters for Triggering an Audio Indication by Frequency Threshold Only (one Condition Set utilized)

| Parameter | Value* |
|---|---|
| | level 2: 1.00 kHz/sec* |
| | level 1: 1.00 kHz/sec* |
| Frequency Threshold, Condition Set 1 | 55,100 Hz |
| Time to wait | 100 msec |
| Cross-back Frequency Slope Threshold | −1.00 kHz/sec* |
| First Pulse Amplitudes (one for each power level) | N/A |
| First Pulse Time | N/A |
| Second Pulse Amplitudes (one for each power level) | N/A |
| Second Pulse Time | N/A |

*These parameter values are set to an appropriate extreme such that they do not effectively take part in logic flow (e.g., set to always be "true")

FIGS. 29-34 show waveforms produced by a generator with the representative/illustrative parameters contained in TABLE 5. The generator may be similar to any one of the generators 30, 500, 1002 disclosed herein, which forms a portion of the respective surgical systems 19, 190, 1000 operating in ultrasonic mode (e.g., ultrasonic system 19, 190, 1000) applied on tissue in accordance with the present disclosure.

The selection of 55,100 Hz as the frequency threshold in TABLE 5 was based on test data for two abuse cases: (1) where an ultrasonic instrument is activated against the tissue pad for a prolonged period of time; and (2) where an ultrasonic instrument is used to make 10 successive cuts on excised porcine jejunum tissue as quickly as possible while keeping the generator running throughout. Each of these two abuse cases will be discussed in more detail with reference to respective FIG. 29 and FIGS. 30-31A-C.

FIG. 29 is a graphical representation 1600 of frequency change 1602 over time of waveforms of several generators during a burn-in test. Frequency change (kHz) after X seconds of burn-in is shown along the vertical axis and ultrasonic surgical instrument device number is shown along the horizontal axis. FIG. 29 shows frequency change data after prolonged burn-ins of an ultrasonic surgical instrument where the ultrasonic surgical instrument is activated against the tissue pad for a prolonged period of time (a prolonged burn-in). The selection of 55,100 Hz limits this condition to no more than a 4 second time span or a frequency drop of about a 700 Hz from a nominal room temperature resonant frequency of 55,800 Hz. Frequency change data 16021, 16022, 16023, 16024 was pulled from the generator 30, 500, 1002 data at corresponding 1, 2, 3, and 4 seconds into the burn-in. The nominal start frequency for the five ultrasonic surgical instruments was 55.8 kHz (blades started at room temperature). The second and fifth devices did not run long enough to generate a full set of data for all times.

FIG. 30 is a graphical representation 1604 of normalized combined impedance, current, and frequency versus time waveforms of and power consumption, energy supplied, and temperature for one embodiment of a generator coupled to a corresponding ultrasonic instrument used to make 10 successive cuts on tissue (e.g., on excised porcine jejunum tissue) as quickly as possible while keeping the generator running throughout. This data and the methods used to obtain it represent abusive use conditions.

Figure 31A:
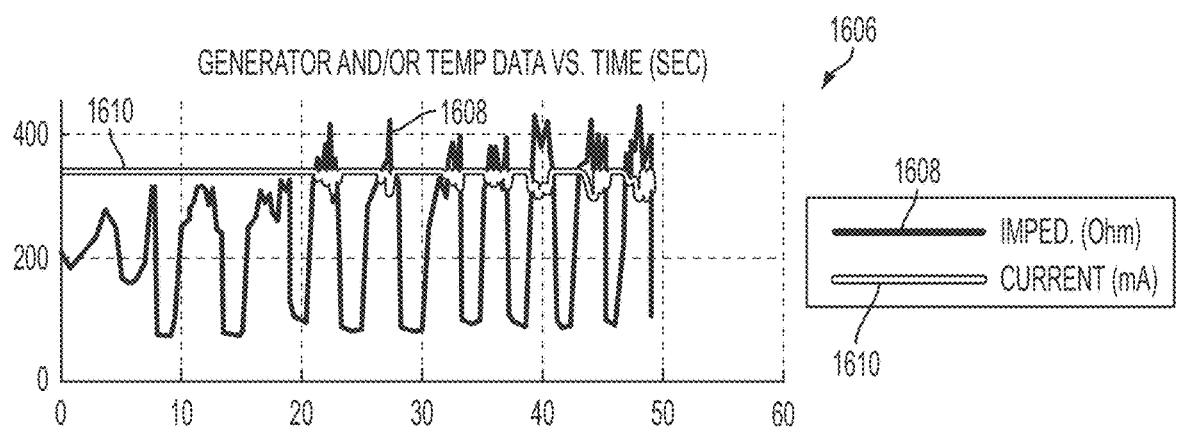
FIG. 31A is a graphical representation of impedance and current versus time waveforms of one embodiment of a generator during successive tissue cuts over a period of time.
Figure 31B:
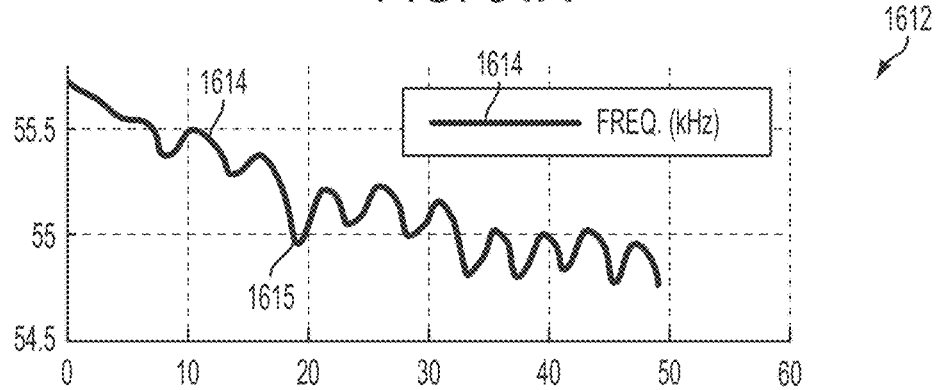
FIG. 31B is a graphical representation of frequency versus time waveform of one embodiment of a generator during successive tissue cuts over a period of time.
Figure 31C:
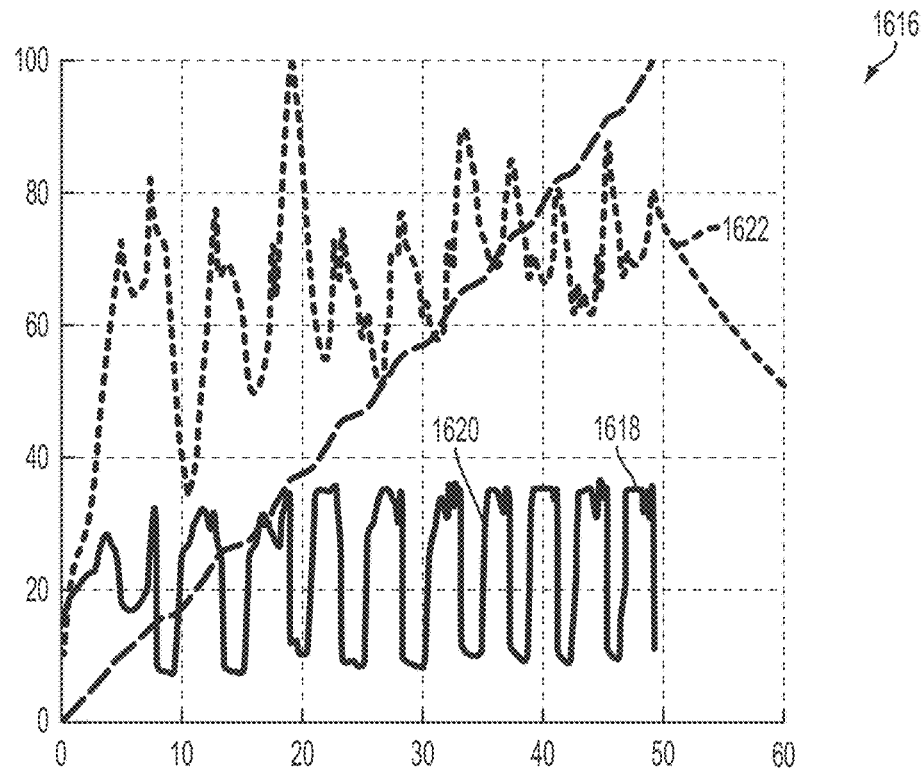
FIG. 31C is a graphical representation of power, energy, and temperature versus time waveforms of one embodiment of a generator during successive tissue cuts over a period of time.

The representative data in FIG. 30 is shown more clearly with reference to FIGS. 31A-C. FIG. 31A is a graphical representation 1606 of impedance versus time waveform 1608 and current versus time waveform 1610 of one embodiment of a generator during successive tissue cuts over a period of time. Impedance (Ohm) and Current (mA) are shown along the vertical axis and time (Sec) along the horizontal axis.

FIG. 31B is a graphical representation 1612 of resonant frequency waveform 1614 versus time of a signal of one embodiment of a generator during successive tissue cuts over a period of time. Resonant frequency (kHz) is shown along the vertical axis and time (Sec) along the horizontal axis.

FIG. 31C is a graphical representation 1616 of a power waveform 1618, energy waveform 1620, and temperature waveform 1622 versus time of one embodiment of a generator during successive tissue cuts over a period of time. Power (W), Energy (J), and Temp (C) are shown along the horizontal axis and time (Sec) along the horizontal axis.

Accordingly, with reference now to FIGS. 31A-C, as shown in the graphical representation 1612, it can be seen that after the resonant frequency curve 1614 has dropped 700 Hz (from 55.8 kHz to 55.1 kHz) at 1615 on the third cut (which is a particularly abusive cut wherein the tissue was tip loaded. After the resonance frequency waveform 1614 has dropped 700 Hz (from 55.8 kHz to 55.1 kHz) on the third cut, the ultrasonic instrument begins to saturate the generator and the current waveform 1610 dips slightly in all successive cuts. Since the drive current waveform 1610 is proportional to blade tip displacement, a dipping current waveform 1610 results in slower speed of tissue effect and therefore a lower energy deposition rate (and lower rate of heating, i.e., frequency slope is less negative). Management of this change due to dipping current waveform 1610 within an application sequence is possible using both frequency change and frequency slope change as will be described in connection with Examples 3 and 4 in subsequent sections of this specification.

FIG. 32 is a combined graphical representation 1630 of a frequency waveform 1632, weighted frequency slope waveform 1634 (calculated via exponentially weighted moving average with an alpha value of 0.1), and temperature waveform 1636 versus time generated by a generator similar to one embodiment of the generators described herein. The ultrasonic system had a room temperature resonant frequency (longitudinal mode) slightly higher than that for which TABLE 5 was constructed. Therefore, the frequency threshold 1633 was increased accordingly from the 55,100 Hz shown in TABLE 5 to about 55,200 Hz shown in FIG. 33 as indicated by the dashed line. The activation was performed on tissue (e.g., on excised porcine jejunum tissue) with an ultrasonic system having a room temperature resonance of about 55.9 kHz set on power level 5. Tissue separation occurs at 6.25 seconds; one side of the tissue separates from the blade at about 8 seconds; and full separation occurs at about 10 seconds. FIG. 33 is a graphical representation of a frequency versus time waveform 1632 of one embodiment of a generator 30, 500, 1002. Frequency (kHz) is shown along the vertical axis and Time (Sec) is shown along the horizontal axis. FIG. 33 shows the example of using a frequency threshold 1633 only using parameters consistent with those shown in TABLE 5, but adjusted to about 55,200 Hz as indicated by the dashed line 1633. The resonant frequency 1632 crosses the frequency threshold 1633 (dashed horizontal line—set at 700 Hz below room temperature resonance) at about 11 seconds and a Response Set may be triggered at this time.

FIG. 34 is a graphical representation 1634 of weighted frequency slope versus time waveform 1634 of one embodiment of a generator. Weighted frequency slope (kHz/Sec) is shown along the vertical axis and Time (Sec) is shown along the horizontal axis. The frequency slope waveform 1634 is calculated via exponentially weighted moving average with an alpha value of 0.1. In FIG. 34, the frequency slope waveform 1634 crosses the frequency slope threshold 1635 (dashed horizontal line) and a Response Set may be triggered at about 5.8 seconds.

The remaining Examples 3 and 4 relate to the use of multiple Condition Sets, which require a more complex application of the tissue algorithm and includes the monitoring of frequency slope and/or frequency against their respective thresholds and may include a hierarchical approach to triggering response sets.

Example 3: Triggering a Response Set Based on Both the Frequency Slope Threshold and the Frequency Threshold A third example case includes triggering a Response Set based on both the frequency slope threshold and the frequency threshold. TABLE 6 contains representative parameters for this objective in connection with surgical instruments such as any one of the surgical instruments 19, 190, 1000 disclosed herein comprising corresponding ultrasonic instruments such as the ultrasonic instruments 100, 120, 1004 disclosed herein.

TABLE 6

Representative Parameters for Triggering Audio Indications by Frequency Slope and Frequency Thresholds (two Condition Sets utilized)

| Parameter | Value* |
| --- | --- |
| Condition Set 1 Pulsing flag | 0 |
| Condition Set 1 LCD display flag | 0 |
| Condition Set 1 Audio flag | 1 |
| Condition Set 2 Pulsing flag | 0 |
| Condition Set 2 LCD display flag | 0 |
| Condition Set 2 Audio flag | 1 |
| Required time before triggered, Condition Set 1 | 50 msec |
| Minimum latch time, Condition Set 1 | 0 msec* |
| Frequency Slope Thresholds (one for each power level), Condition Set 1 | level 5: −0.060 kHz/sec<br>level 4: −0.053 kHz/sec<br>level 3: −0.045 kHz/sec<br>level 2: −0.038 kHz/sec<br>level 1: −0.030 kHz/sec |
| Frequency Threshold, Condition Set 1 | 56,000 Hz* |
| Required time before triggered, Condition Set 2 | 50 msec |
| Minimum latch time, Condition Set 2 | 0 msec* |
| Frequency Slope Thresholds (one for each power level), Condition Set 2 | level 5: 1.00 kHz/sec*<br>level 4: 1.00 kHz/sec*<br>level 3: 1.00 kHz/sec*<br>level 2: 1.00 kHz/sec*<br>level 1: 1.00 kHz/sec* |
| Frequency Threshold, Condition Set 2 | 55,100 Hz |
| Time to wait | 100 msec |
| Cross-back Frequency Slope Threshold | −0.020 kHz/sec |
| First Pulse Amplitudes (one for each power level) | N/A |
| First Pulse Time | N/A |
| Second Pulse Amplitudes (one for each power level) | N/A |
| Second Pulse Time | N/A |

*These parameter values are set to an appropriate extreme such that they do not effectively take part in logic flow (e.g. set to always be "true")

In this case of Example 3, a tiered or hierarchical response is demonstrated. The combined logic of the frequency slope threshold and the frequency threshold will be illustrated using the same graphical representations shown in FIGS. 32-34. In FIG. 34, Condition Set 1 is triggered by the frequency slope waveform 1634 crossing the frequency slope threshold 1635 value at about 6 seconds. The Response Set for Condition Set 1 may include a low level audible indicator, for example. As the user continues to activate the instrument with minimal intervening tissue, Condition Set 2 is triggered as the resonant frequency drops below the frequency threshold 1633 at about 11 seconds as shown in FIG. 33. The Response Set for Condition Set 2 may be an elevated audible indicator, for example.

Example 4: Triggering a Response Set Based on Both the Frequency Slope Threshold and the Frequency Threshold A fourth example extends to the application of both frequency and frequency slope thresholds during abusive conditions of the surgical instrument. For various reasons, the frequency slope signal levels may diminish (i.e., become less negative) with extended application.

In abusive conditions, frequency, frequency slope, and current waveforms may deviate from normal operation may be generated while the ultrasonic instrument is constantly activated at a power level 5, where the jaws of the ultrasonic instrument were opened for 1 second, then closed for 1 second and repeated for 17 cycles.

When an ultrasonic instrument is activated multiple times directly against the pad, the characteristic frequency slope waveform in a first region before the generator saturates becomes less negative than in a second after the generator saturates due, in large part, to the system efficiency and resulting displacement/current drop. In the non-saturation region of the frequency slope waveform, the ultrasonic system has not yet saturated and current is maintained at or near the target current for power level 5. In the saturation region of the frequency slope waveform, the current (and therefore blade tip displacement) continually drops causing the frequency slope to increase (rate of heating drops). Note that at after several abusive cycles, e.g., the fourth abuse cycle, which is the approximate demarcation between the non-saturation and saturation regions, the resonant frequency drops consistent with FIGS. 29-31A-C. Separate Conditions Sets for each of the non-saturation and saturation regions may be applied. A first frequency slope threshold may be employed in the non-saturation region when resonant frequency conditions are above a predetermined frequency threshold and a second, less negative frequency slope threshold may be employed in the saturation region when resonant frequency conditions are below the same predetermined frequency threshold.

A weighted frequency slope (kHz/sec) versus time waveform may be of one embodiment of a generator. When the instrument is used abusive conditions against the pad, the characteristic frequency slope waveform in the non-saturation region becomes less negative than in the saturation region due to material softening and a corresponding reduction in pad coefficient of friction. In the non-saturation region of the frequency slope waveform corresponds to when the tissue pad has not yet begun to heat significantly. In the saturation region of the frequency slope waveform, the pad begins to soften and the interface between the blade and the pad becomes more lubricious causing the frequency slope waveform to increase (rate of heating drops). Separate Conditions Sets for each of the non-saturation and saturation regions may be warranted. A first frequency slope threshold may be employed in the non-saturation region when resonant frequency conditions are above a predetermined frequency slope threshold and a second, less negative frequency slope threshold may be employed in the saturation region when the resonant frequency is below the same predetermined frequency slope threshold.

Another example case is now considered. TABLE 7 contains parameters for an ultrasonic instrument where two Condition Sets are used to account for diminishing frequency slope signal levels due to system saturation and dropping current.

TABLE 7

Representative Parameters for Triggering Audio Indications by Frequency Slope and Frequency Thresholds, accounting for diminishing frequency slope due to system saturation (two Condition Sets utilized)

| Parameter | Value* |
|---|---|
| Condition Set 1 Pulsing flag | 0 |
| Condition Set 1 LCD display flag | 0 |
| Condition Set 1 Audio flag | 1 |
| Condition Set 2 Pulsing flag | 0 |
| Condition Set 2 LCD display flag | 0 |
| Condition Set 2 Audio flag | 1 |
| Required time before triggered, Condition Set 1 | 50 msec |
| Minimum latch time, Condition Set 1 | 0 msec* |
| Frequency Slope Thresholds (one for each power level), Condition Set 1 | level 5: −0.060 kHz/sec<br>level 4: −0.053 kHz/sec<br>level 3: −0.045 kHz/sec<br>level 2: −0.038 kHz/sec<br>level 1: −0.030 kHz/sec |
| Frequency Threshold, Condition Set 1 | 56,000 Hz* |
| Required time before triggered, Condition Set 2 | 50 msec |
| Minimum latch time, Condition Set 2 | 0 msec* |
| Frequency Slope Thresholds (one for each power level), Condition Set 2 | level 5: −0.045 kHz/sec<br>level 4: −0.038 kHz/sec<br>level 3: −0.030 kHz/sec<br>level 2: −0.024 kHz/sec<br>level 1: −0.020 kHz/sec |
| Frequency Threshold, Condition Set 2 | 55,100 Hz |
| Time to wait | 100 msec |
| Cross-back Frequency Slope Threshold | −0.020 kHz/sec |
| First Pulse Amplitudes (one for each power level) | N/A |
| First Pulse Time | N/A |
| Second Pulse Amplitudes (one for each power level) | N/A |
| Second Pulse Time | N/A |

*These parameter values are set to an appropriate extreme such that they do not effectively take part in logic flow (e.g., set to always be "true")

The data generated for this example run were generated using an ultrasonic instrument to make ten successive cuts in jejunum tissue as quickly as possible. Using the parameter values from TABLE 7, the Frequency vs. Time plots for the example sample case are shown in FIGS. 35-36.

Figure 35:
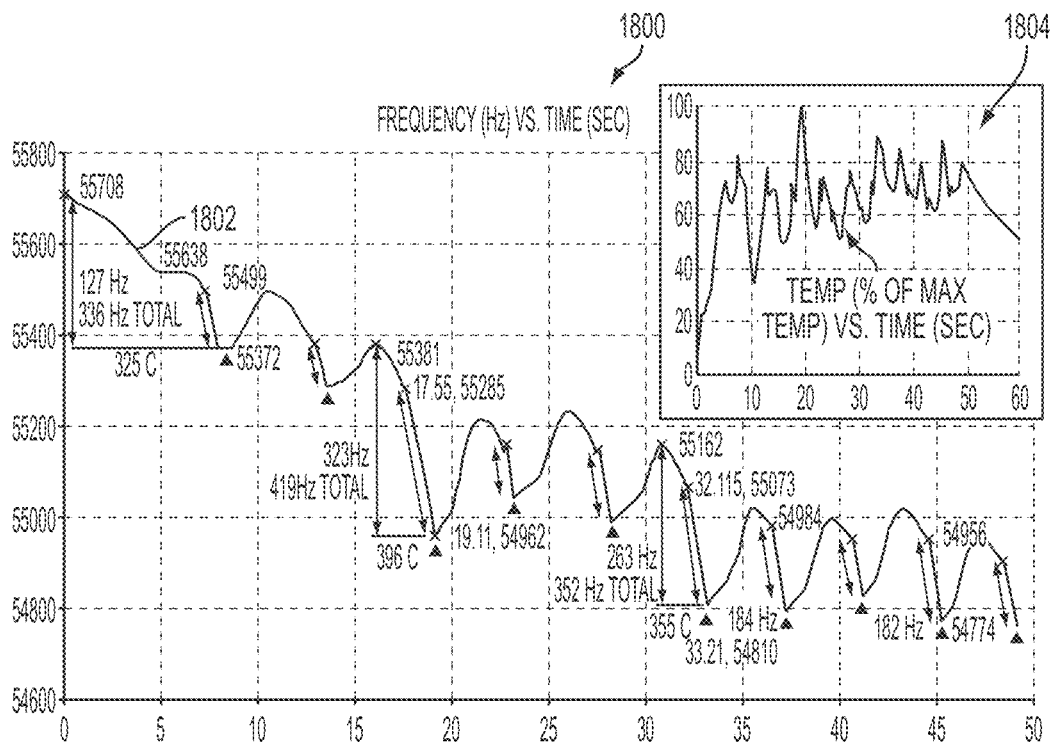
FIG. 35 is a graphical representation of a frequency versus time waveform of one embodiment of a generator over ten cuts on jejunum tissue and a graphical representation of a temperature versus time signal.

FIG. 35 is a graphical representation 1800 of a frequency versus time waveform 1802 of one embodiment of a generator over ten cuts on tissue (e.g., jejunum tissue) and a graphical representation 1804 of a temperature versus time waveform 1805. For the graphical representation 1800, Frequency (Hz) is shown along the vertical axis and Time (Sec) is shown along the horizontal axis. For the graphical representation 1804, Temperature (° F.) is shown along the vertical axis and Time (Sec) is shown along the horizontal axis.

Figure 36:
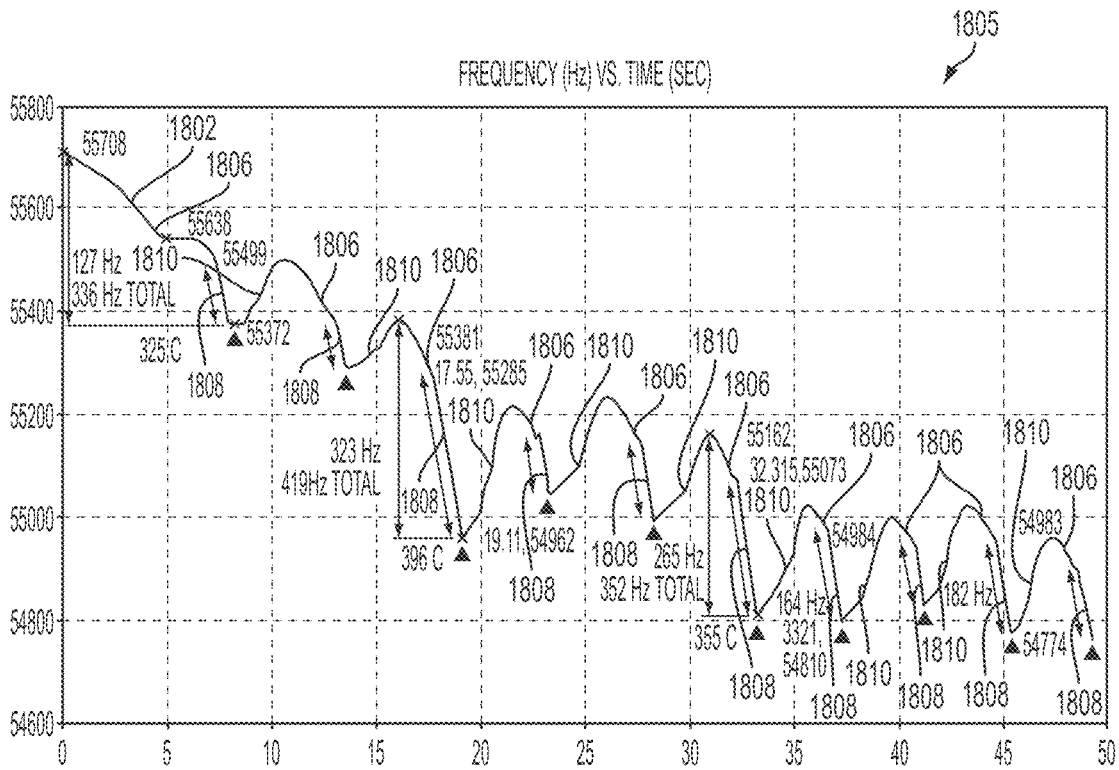
FIG. 36 is a graphical representation of the frequency versus time waveform shown in FIG. 35 of one embodiment of a generator over ten cuts on jejunum tissue with activation of intervening tissue.

FIG. 36 is a graphical representation 1805 of the frequency versus time waveform 1802 shown in FIG. 35 of one embodiment of a generator over ten cuts on tissue (e.g., jejunum tissue) with activation of intervening tissue at portions indicated by reference number 1806. Frequency (Hz) is shown along the vertical axis and Time (Sec) is shown along the horizontal axis.

The frequency waveform 1802 shown in FIGS. 35 and 36 is for the example case using two Condition Sets to account for diminishing frequency slope due to electrical system saturation (diminishing displacement). Note that this is the same test run as is shown in FIGS. 29-31A-C. In FIG. 36, the highlighted portions 1806 indicates activation with intervening tissue (frequency drops, shape of local frequency curve related to dryness of tissue—shallow start slope, steepens as tissue dries), the highlighted portions 1808 indicate activation with minimal or no intervening tissue (local frequency slope very steep, curve shape is more linear, steepens gradually), the section of the curve with no highlighted portions 1810 indicates time within which the device is being repositioned for the next cut, blade cools in air and cools rapidly when placed on tissue (frequency rises).

Figure 37:
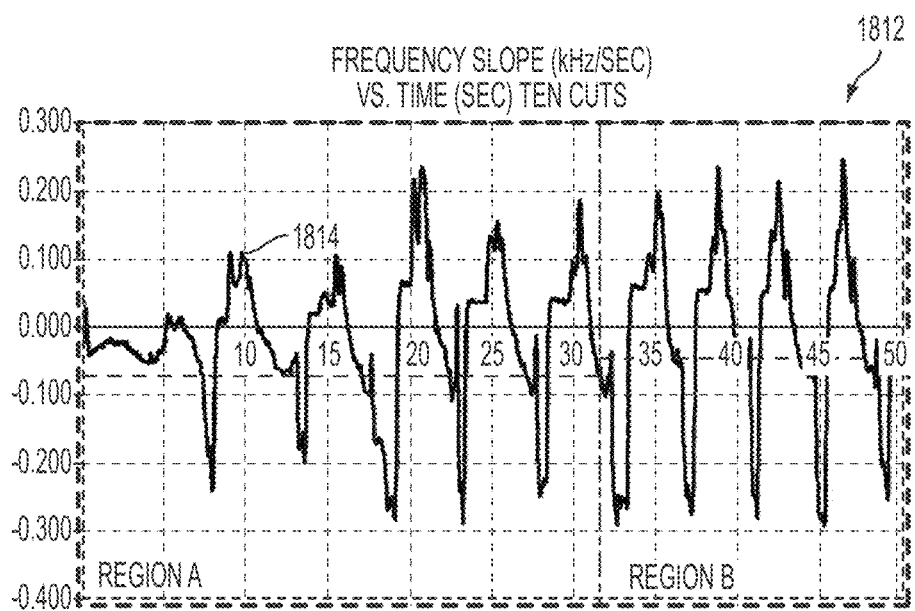
FIG. 37 is a graphical representation of a frequency slope versus time waveform of one embodiment of a generator over ten cuts on jejunum tissue.

FIG. 37 is a graphical representation 1812 of a frequency slope versus time waveform 1814 of one embodiment of a generator over ten cuts on jejunum tissue. Frequency slope (kHZ/Sec) is shown along the vertical axis and Time (Sec) is shown along the horizontal axis. Region B of the frequency slope waveform 1814 shows the area of the ten cut run where Condition Set 2 is triggered prior to Condition Set 1 for the first time during the ten cut run (frequency is below 55.1 kHz and frequency slope is less than −0.045 kHz/sec). The condition illustrated in Region B, where Condition Set 2 is triggered prior to Condition Set 1, is desired because the ultrasonic system is consistently saturating by this point in the run (voltage is saturating and current is diminished resulting in diminished displacement and, therefore, diminished rate of heating requiring a greater frequency slope threshold).

Figure 38:
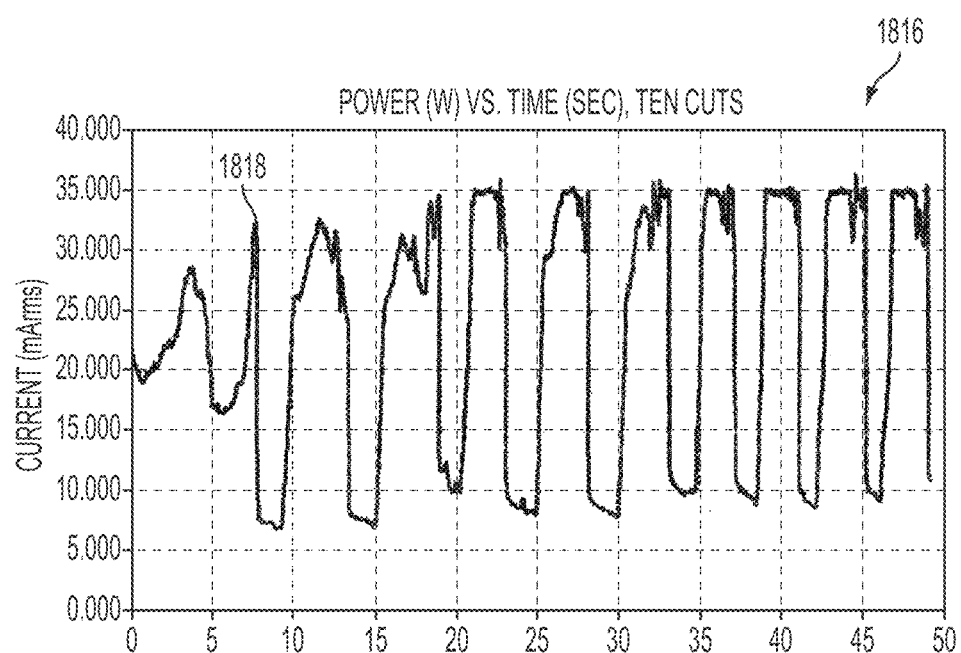
FIG. 38 is a graphical representation of a power versus time waveform representative of power consumed by a one embodiment of a generator over ten cuts on jejunum tissue.

FIG. 38 is a graphical representation 1816 of a power versus time waveform 1818 representative of power consumed by a one embodiment of a generator over ten cuts on tissue (e.g. jejunum tissue). Power (W) is shown along the vertical axis and Time (Sec) is shown along the horizontal axis.

Figure 39:
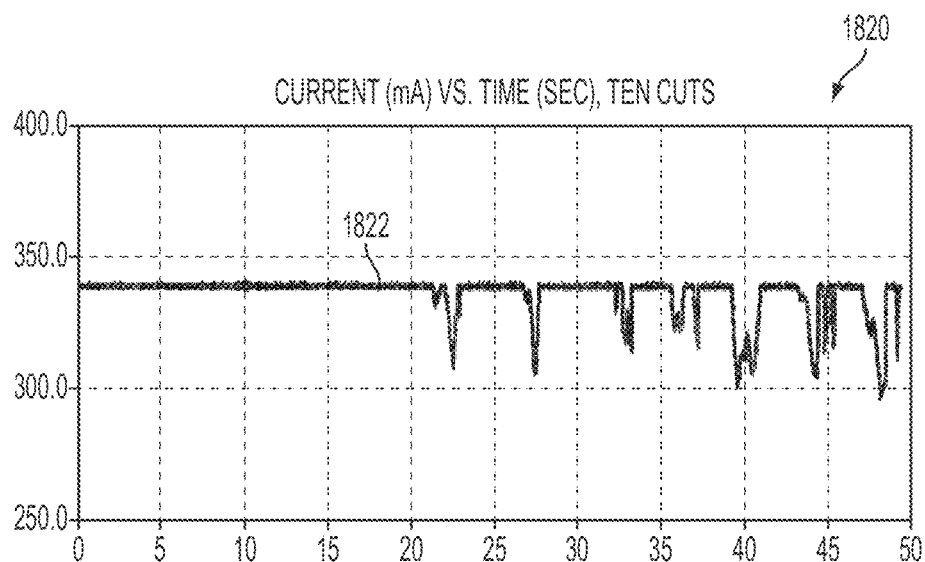
FIG. 39 is a graphical representation of a current versus time waveform of one embodiment of a generator over ten cuts on jejunum tissue.

FIG. 39 is a graphical representation 1820 of a current versus time waveform 1822 of one embodiment of a generator over ten cuts on jejunum tissue. Current (mA) is shown along the vertical axis and Time (Sec) is shown along the horizontal axis.

Figure 48:
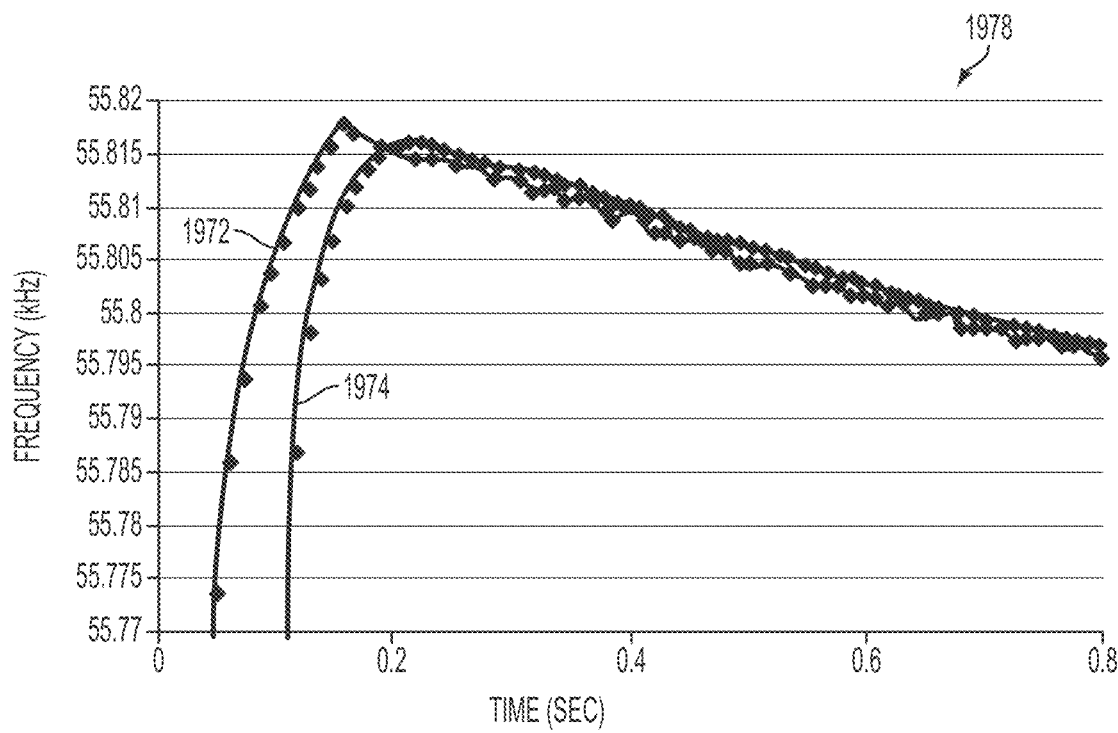
FIG. 48 is a zoomed in view of the resonant frequency and averaged resonant frequency versus time waveforms shown in FIG. 47.
Figure 49:
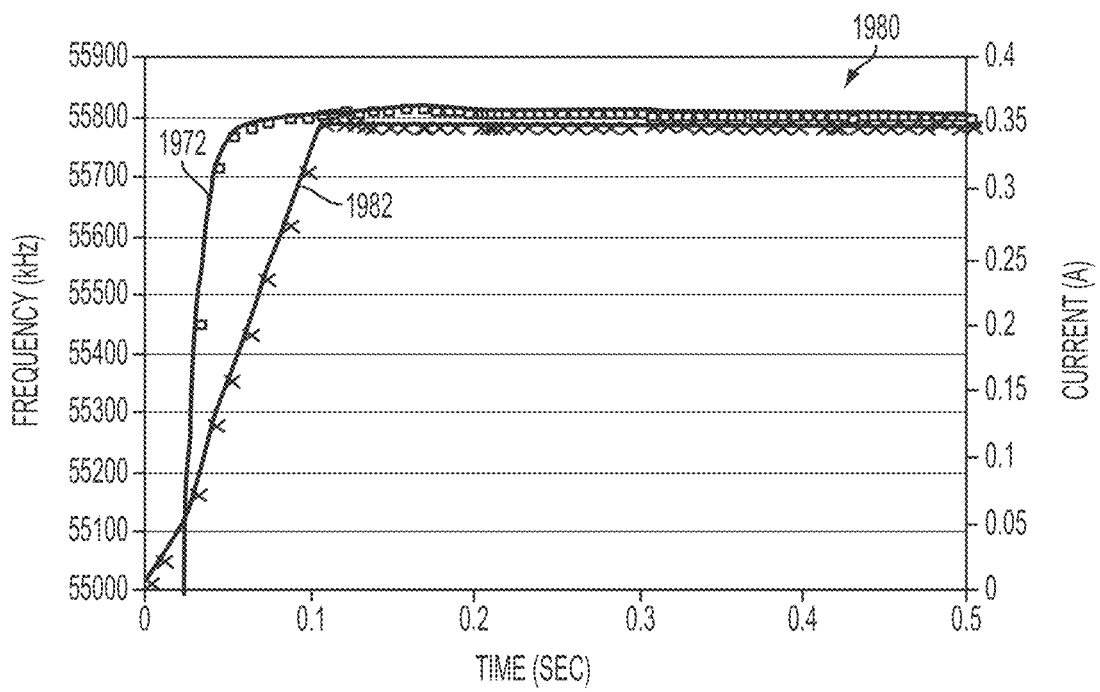
FIG. 49 is a zoomed in view of the resonant frequency and current versus time waveforms of one embodiment of a generator.

Having described the basic application of the tissue algorithm discussed in connection with the logic flow diagrams 1200, 1300, 1400 shown in FIGS. 20-22 in terms of monitoring the frequency slope, resonant frequency, or both against their respective thresholds, the discussion now turns to a description of the latching logic and corresponding use as it relates to the tissue algorithm. The motivations for adding the latching logic to the tissue algorithm are: (a) to prevent a Condition Set from resetting (Condition Set changes from true to false) due to a blade/pad interface becoming more lubricious during a blade on pad abuse condition; and (b) to prevent a Condition Set from resetting (Condition Set changes from true to false) due to pulsed activation where periods of rapid heating are interweaved with periods of less rapid heating (sections of heat flux into the blade and sections of heat flux out of the blade are interweaved). The first and second of these motivations are shown in FIGS. 48 and 49 illustrate, respectively. As defined earlier in this disclosure, the two latch parameters addressing these motivations are "cross-back frequency slope threshold" as shown in FIG. 40 and "minimum latch time." For completeness of disclosure, FIG. 43 shows calculated frequency slope curves for the pulsed run shown in FIGS. 41 and 42A-C.

Figure 40:
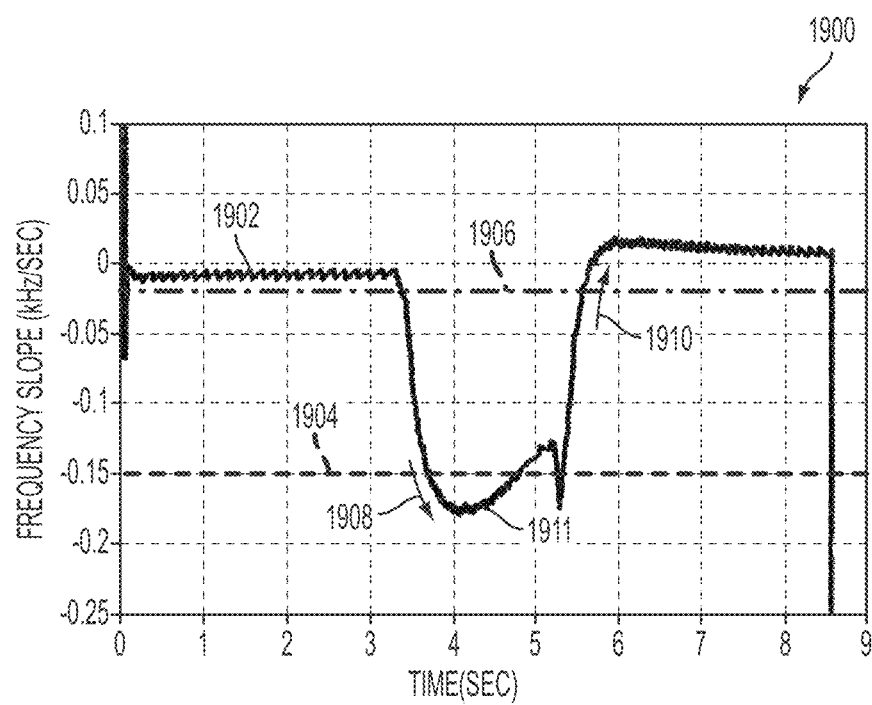
FIG. 40 is a graphical representation of a "cross-back frequency slope threshold" parameter in connection with a frequency slope vs. time waveform of one embodiment of a generator.

FIG. 40 is a graphical representation 1900 of a "cross-back frequency slope threshold" parameter in connection with frequency slope versus time waveform 1902. As shown in FIG. 40, the "frequency slope threshold" 1904 is shown by the horizontal dashed line at −0.15 kHz/sec. The "cross-back frequency slope threshold" 1906 is shown by the horizontal dash-dot line at −0.02 kHz/sec. In this instance, the Condition Set is met and a Response Set is triggered when the local calculated frequency slope crosses the "frequency slope threshold" as shown by arrow 1908 pointing down. The Condition Set is not met (Response Set is no longer triggered) when the local calculated frequency slope crosses over the "cross-back frequency slope threshold" as shown by arrow 1910 pointing up. Note that without using the "cross-back over frequency slope threshold" in this case, the Response Set would not have been triggered when the local frequency slope crossed back over the horizontal dashed line 1904 at about 4.7 seconds shown at cross over point 1911.

Figure 41:
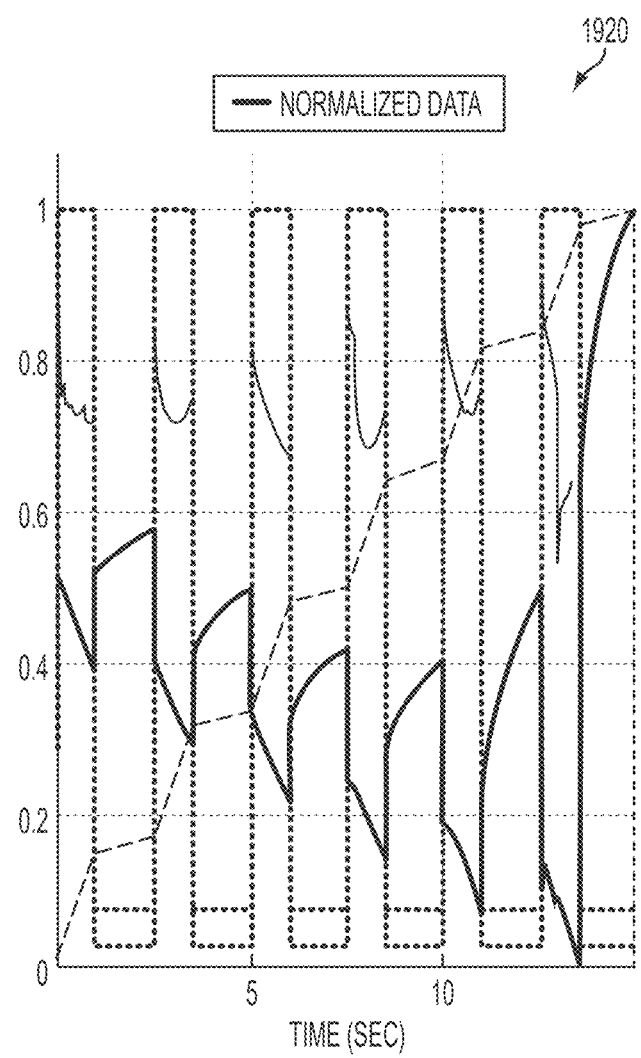
FIG. 41 is a combined graphical representation of a pulsed application of one embodiment of an ultrasonic instrument on an excised carotid artery showing normalized power, current, energy, and frequency waveforms versus time.

FIG. 41 is a combined graphical representation 1920 of a pulsed application of one embodiment of an ultrasonic instrument on an excised carotid artery showing normalized power, current, energy, and frequency data plotted versus time.

Figure 42A:
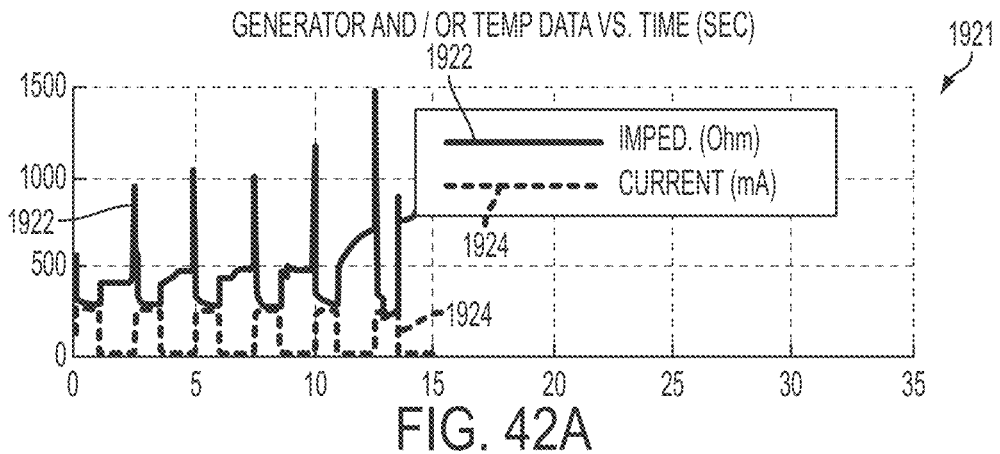
FIG. 42A is a graphical representation of impedance and current versus time waveforms of one embodiment of a generator during successive tissue cuts over a period of time.
Figure 43:
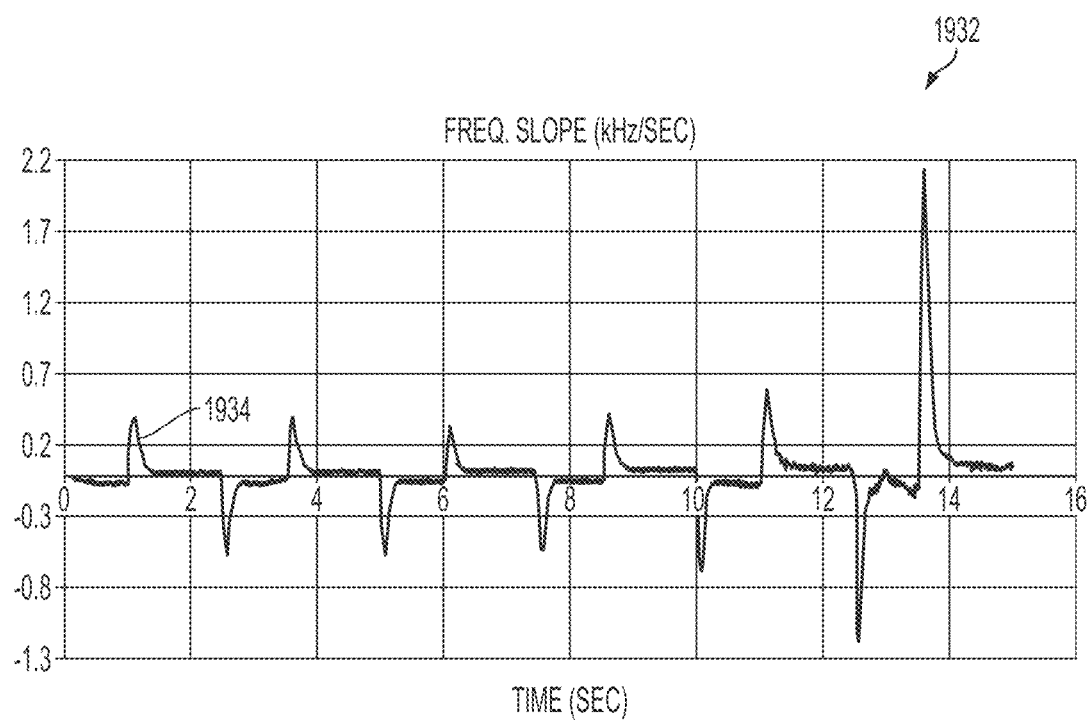
FIG. 43 is a graphical representation of a calculated frequency slope waveform for the pulsed application shown in FIG. 41 and FIGS. 50A-C plotted on a gross scale.

FIG. 42A is a graphical representation 1921 of an impedance versus time waveform 1922 and a current versus time waveform 1924 of one embodiment of a generator during successive tissue cuts over a period of time. The impedance (Ohms) and current (mA) is shown along the vertical axis and Time (Sec) is shown along the horizontal axis.

Figure 42B:
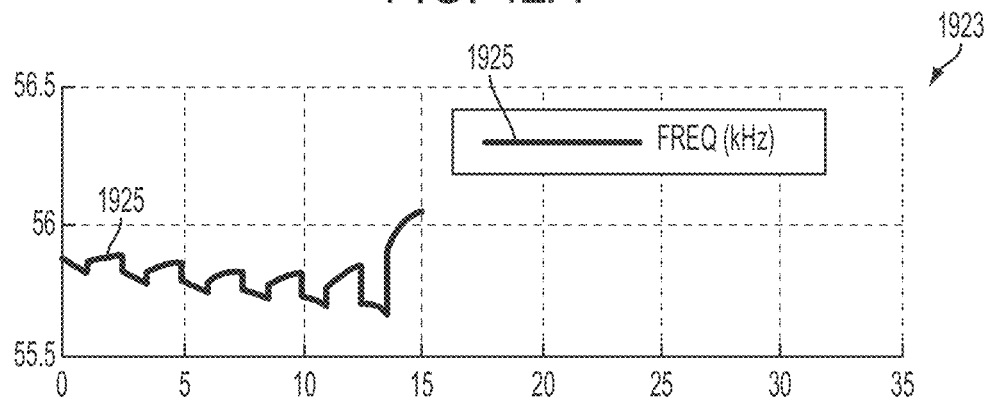
FIG. 42B is a graphical representation of a frequency versus time waveform of one embodiment of a generator during successive tissue cuts over a period of time.

FIG. 42B is a graphical representation 1923 of a frequency versus time waveform 1925 of one embodiment of a generator during successive tissue cuts over a period of time. Frequency (kHz) is shown along the vertical axis and Time (Sec) is shown along the horizontal axis.

Figure 42C:
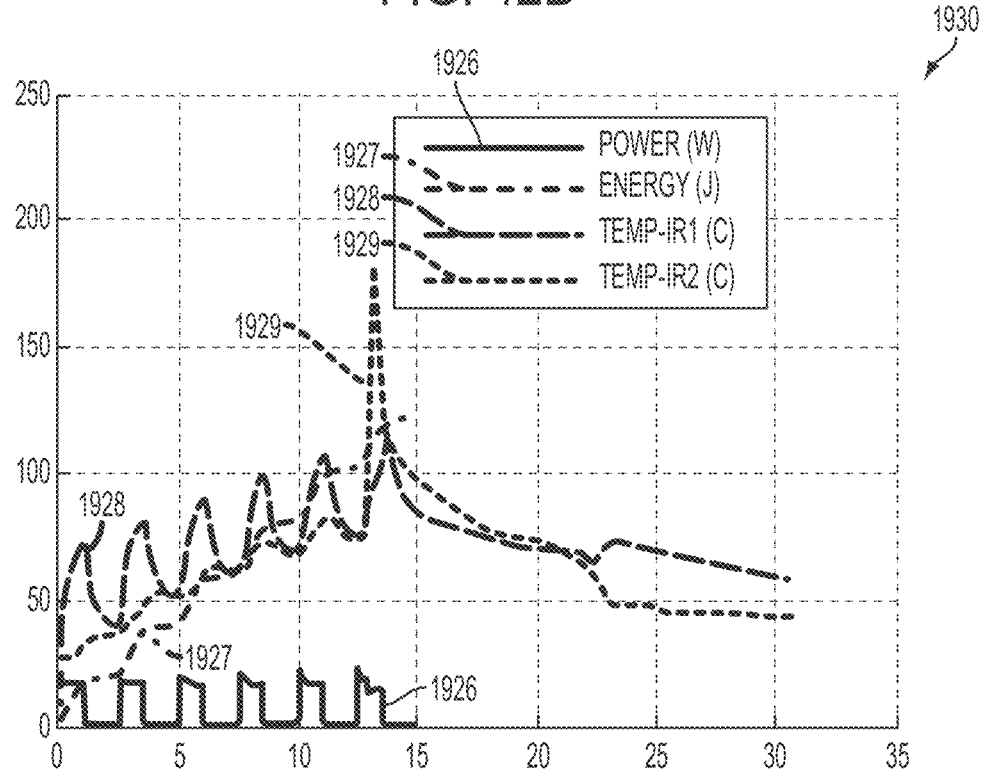
FIG. 42C is a graphical representation of power, energy, and temperature versus time waveforms of one embodiment of a generator during successive tissue cuts over a period of time.

FIG. 42C is a graphical representation 1930 of power waveform 1926, energy waveform 1927, a first temperature waveform 1928 and a second temperature waveform 1929 plotted versus time as of one embodiment of a generator during successive tissue cuts over a period of time. Power (W), Energy (J), and Temperature (° C.) are shown along the vertical axis and Time (Sec) is shown along the horizontal axis.

FIGS. 42A-C show a pulsed application of an ultrasonic instrument on an excised carotid artery where the First Pulse Time is 1 second, the First Pulse Amplitude is 100% of power level 3 output current. The Second Pulse Time is 1.5 seconds and the Second Pulse Amplitude is less than 10% of power level 3 output current. Of note, the resonant frequency waveform 1925 exhibits sections of both heating (heat flux into the blade) and cooling (heat flux out of the blade). The "minimum latch time" parameter, defined herein as the minimum amount of time for response(s) to a Condition Set X to be triggered, is intended to maintain triggering of a Response Set during pulsed application (one example of a latch time may be about 1 second). Of additional note, as shown in FIG. 42A, the load or impedance waveform 1922 does not drop below 200 Ohms throughout the run sequence. This may be favorable considering that the impedance waveform 1922 for a marching application consistently drops below about 150 Ohms while operating in air between cuts implying that an impedance limit may be used for resetting Condition Sets. In one aspect this impedance limit may be used for implementation of the "low drive in air" concept as disclosed in U.S. Pat. No. 5,026,387 to Thomas.

Figure 44:
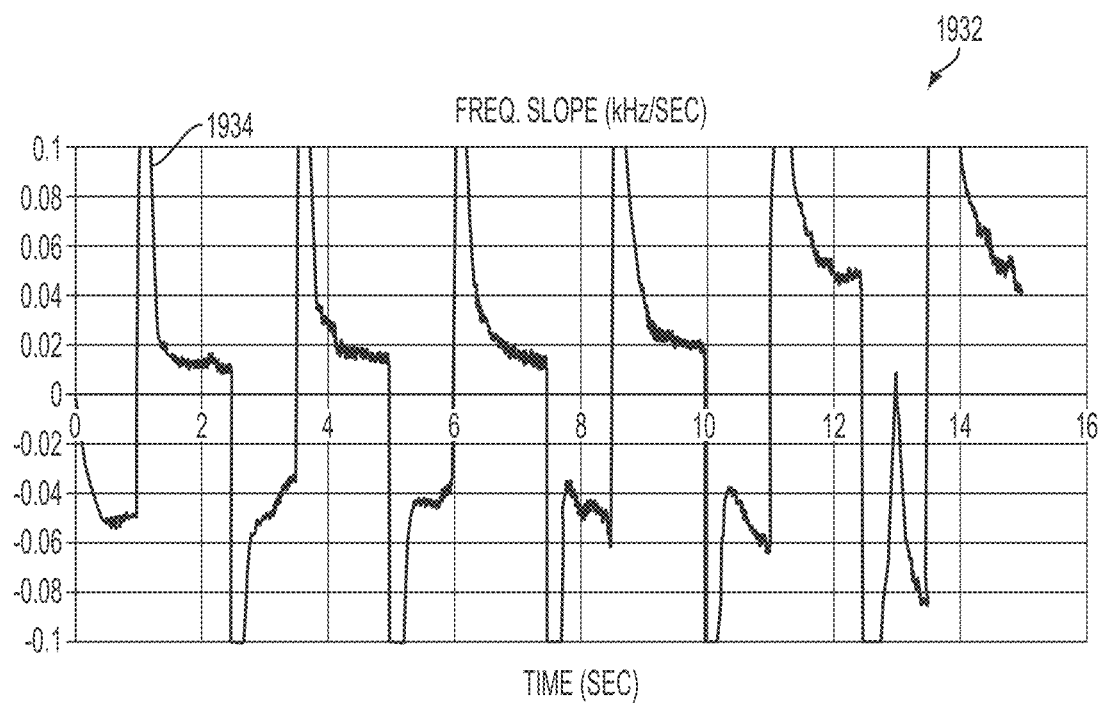
FIG. 44 is a zoomed in view of the graphical representation of the calculated frequency slope waveform for the pulsed application shown in FIG. 43.

FIG. 43 is a graphical representation 1932 of a calculated frequency slope waveform 1934 for the pulsed application shown in FIG. 41 and FIGS. 42A-C plotted on a gross scale. FIG. 44 is a zoomed in view of the graphical representation of the calculated frequency slope waveform 1934 for the pulsed application shown in FIG. 43. Both FIGS. 43 and 44 show the calculated frequency slope waveform 1934 for the pulsed application shown in FIG. 41 and FIGS. 42A-C. Frequency slope (kHz/Sec) is shown along the vertical axis and Time (Sec) is shown along the horizontal axis. Two scales are shown, where FIG. 43 shows a gross scale for frequency slope and FIG. 44 shows a "zoomed in" view. For frequency slope, the same trends seen under continuous drive are shown in pulsed drive including values that correlate well to heat flux into (negative frequency slope) and out of the blade (positive frequency slope). The transient nature of the frequency curve and frequency slope curve due to pulsing, combined with the moving average calculation of frequency slope make use of the frequency slope curve during pulsing difficult. Of note, the tissue separated at 13 seconds. As can be seen in FIG. 43 and especially FIG. 44, the rate of cooling can be used to trigger a response correlating rapid cooling in the dwell portions of pulsed outputs to the completion of a tissue transection using logic (not shown by logic flows in FIGS. 20-22) where frequency slope waveform 1934 exceeds a threshold value, in this case of about 0.04 kHz/sec when sampled at the ends (i.e., the settled regions) of the dwell periods. As can be seen in FIG. 42A, the impedance waveform 1922 can be used to trigger a response correlating high impedance (high resistance to mechanical motion or vibration) to the completion of a tissue transection using logic (again, not shown by logic flows in FIGS. 20-22) where transducer impedance waveform 1922 exceeds a threshold value, in this case of about 700 Ohms when sampled at the beginnings (i.e., the settled regions) of the dwell periods.

Figure 45:
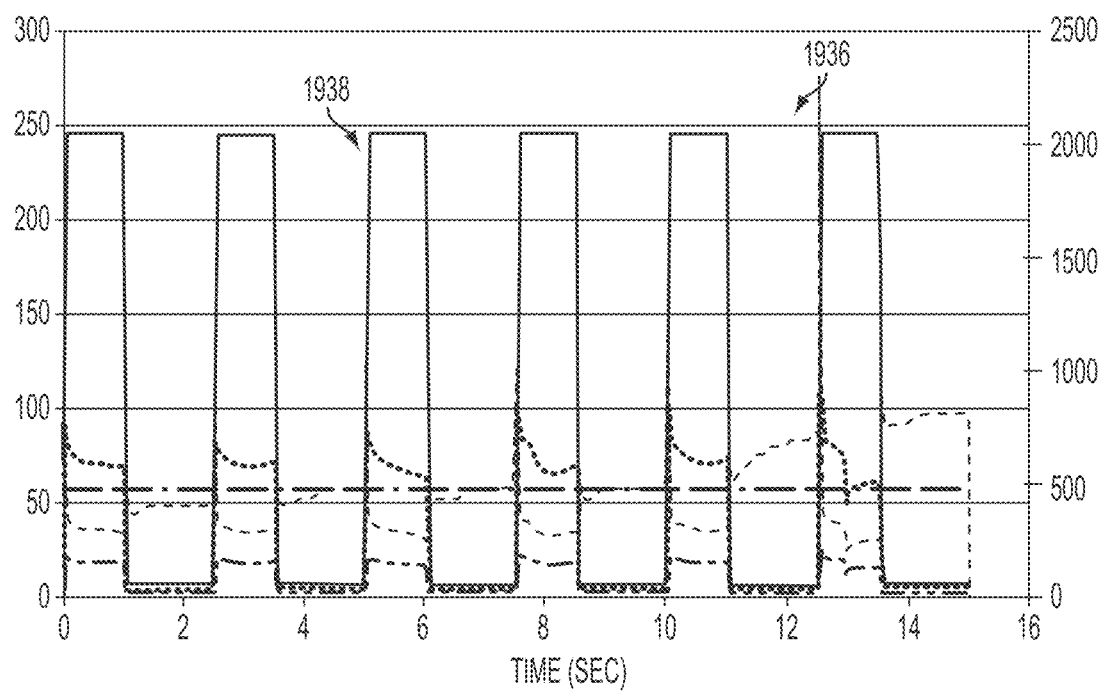
FIG. 45 is a graphical representation of other data waveforms of interest such as impedance, power, energy, temperature.

FIG. 45 is a graphical representation 1936 of other data waveforms 1938 of interest such as impedance, power, energy, temperature. In FIG. 45, the vertical scale to the right applies to the impedance curve only.

The present disclosure now turns to considerations for power level and clamp pressure profile in an ultrasonic instrument. The rate of heating of a blade to pad interface is proportional to blade displacement, interface coefficient of friction and load (clamp pressure or normal force). Testing was performed to assess the tissue algorithm at a range of displacements (power levels) and device specific combinations of clamp pressure and coefficient of friction (defined largely by pad materials and blade coatings).

Figure 46:
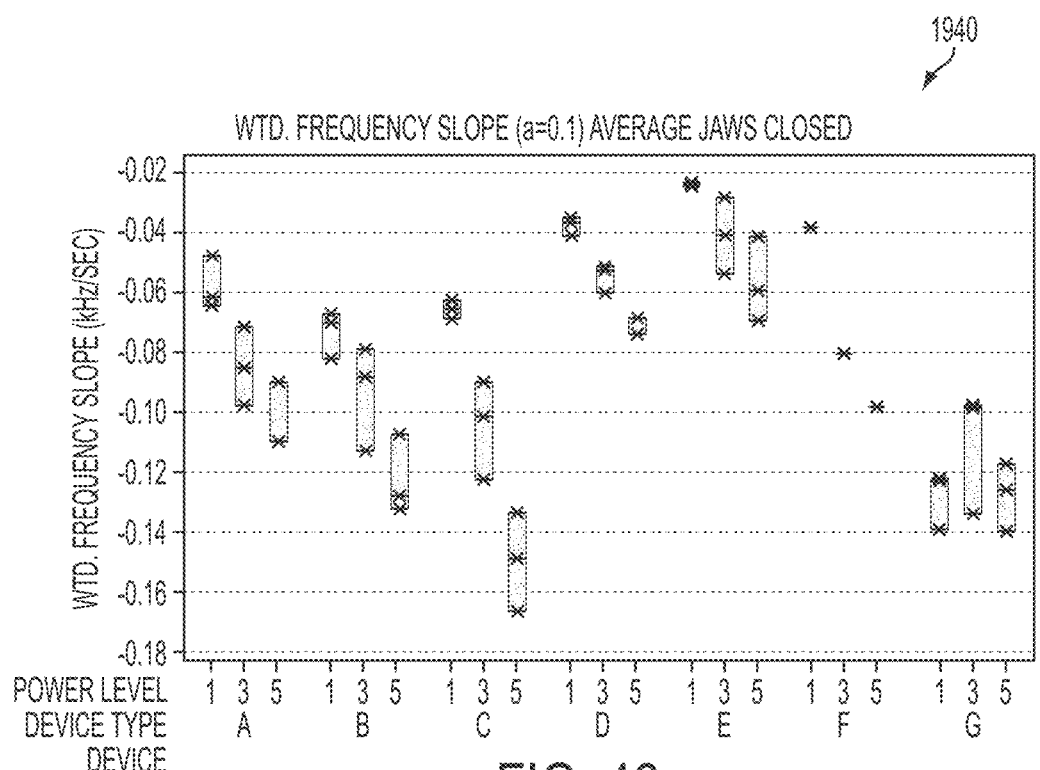
FIG. 46 is a graphical representation of a summary of weighted frequency slope versus power level for various ultrasonic instrument types.

FIG. 46 is a graphical representation 1940 of a summary of weighted frequency slope versus power level for various ultrasonic instrument types. Weighted frequency slope (kHz/Sec) is shown along the vertical axis and power level, device type, and device are shown along the horizontal axis. The instruments used to generate the data summarized in the graphical representation 1940 are generally commercially available with some exceptions. One test procedure included clamping the device, activating the device for three seconds, and calculating the average frequency slope over the full three seconds. Other metrics, however, may be employed. For most devices, the data summarized in FIG. 46 would be approximately indicative of the minimum frequency slope value. FIG. 46 shows the frequency slope summary data for burn-in testing on shears type ultrasonic instruments where the instruments were clamped, then activated for 3 seconds, then unclamped—the average frequency slope over the full three seconds of activation was calculated and plotted as shown.

Based on predetermined tests and test data from FIG. 46, the following frequency slope thresholds are suggested for the main power levels of use with some ultrasonic instruments:

(1) level 5 frequency slope threshold: −0.060 kHz/sec;
(2) level 3 frequency slope threshold: −0.045 kHz/sec;
(3) level 5 frequency slope threshold: −0.070 kHz/sec; and
(4) level 3 frequency slope threshold: −0.050 kHz/sec.

System stiffness includes both blade stiffness (cantilevered beam) and pad stiffness/pad thermal stability. The more differentiated the unloaded (no tissue) system stiffness is from the loaded (clamped on tissue) system stiffness, the more robust the tissue algorithm performance. Other constraints, of course, may limit system stiffness on the high end.

Further exploration of displacement effects were analyzed based on a larger set of data. For the ultrasonic system, power levels are essentially differentiated by output current target values and, current, which is proportional to vibratory amplitude or displacement. Analysis of this data also may include digital smoothing of the frequency data to obtain usable frequency slope curves.

Figure 47:
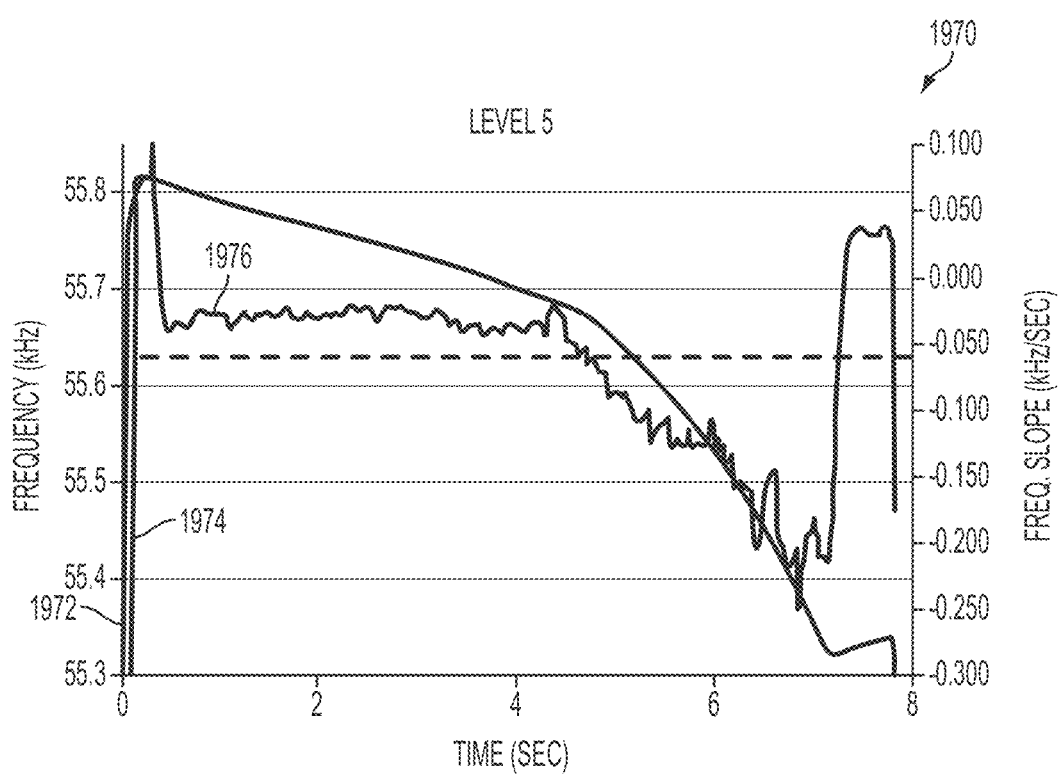
FIG. 47 is a graphical representation of resonant frequency, averaged resonant frequency, and frequency slope versus time waveforms of one embodiment of a generator.

FIGS. 47-49 show frequency and current versus time waveforms obtained using one embodiment of a generator and an ultrasonic instrument to excise a porcine carotid artery at power level 5.

FIG. 47 is a graphical representation 1970 of resonant frequency versus time waveform 1972, an averaged resonant frequency versus time waveform 1974, and a frequency slope versus time waveform 1976 of one embodiment of a generator. Frequency (kHz) and Frequency Slope (kHz/Sec) are shown along the vertical axes and Time (Sec) is shown along the horizontal axis. The frequency slope waveform 1976 is based on the averaged frequency data and was obtained by post processing the frequency waveform 1972 data. The raw frequency data is plotted as well as smoothed (via simple moving average) frequency data and frequency slope (calculated from the smoothed data because the raw frequency data contains stair-stepping due to rounding of the streamed data). The average resonant frequency waveform 1974 is obtained via a 70 msec moving average (kHz) of the resonant frequency data.

FIG. 48 is a zoomed in view 1978 of the resonant frequency versus time waveform 1972 and the averaged resonant frequency versus time waveform 1974 of one embodiment of a generator. Frequency (kHz) is shown along the vertical axis and Time (Sec) is shown along the horizontal axis.

FIG. 49 is a zoomed in view 1980 of the resonant frequency waveform 1972 and a current versus time waveform 1982 of one embodiment of a generator. Frequency in (Hz) and Current (A) is shown along the vertical axes.

In FIGS. 48 and 49, the respective zoomed in views 1978, 1980 are shown to see the effect of smoothing frequency data and to see rise information at the start of the application, which may be helpful for assessment of parameters such as Time to Wait.

Other aspects of the tissue algorithm described herein may be applied to situations when little to no intervening tissue remains (between the ultrasonic blade and the clamp arm) and waste energy is being dumped into the end effector. Accordingly, in one embodiment, the tissue algorithm may be modified to provide feedback to the user relative to this situation. Specifically, the tissue algorithm leverages the fact that the resonance of an ultrasonic blade changes relative to temperature (decreases with increasing temperature and increases with decreasing temperature).

In one aspect the tissue algorithm disclosed herein may be employed to monitor the frequency slope of a waveform where the algorithm monitors the change in resonant frequency slope to indicate the changing condition of the tissue. In the case shown in FIG. 50, for example, the inflection of the frequency response curve correlates to the point at which the tissue begins to separate (i.e., there is a tissue tag and the user continues to activate the instrument), which can be verified by experimentation. The change in frequency slope can be used to provide an indicator (e.g., distinct beeping sound, flashing light, tactile vibration, among others previously discussed) to the user (that waste energy is being dumped into the end effector) or the generator output could be controlled or stopped.

In another aspect, the tissue algorithm disclosed herein may be employed to monitor the frequency threshold of a waveform, where the algorithm monitors the change in frequency as the waveform crosses some threshold or difference from some known state (e.g., room temperature). Similar to monitoring the frequency slope, as the change in frequency drops below some threshold value or difference, an indication can be given to the user that the device end effector is heating at an accelerated rate. Again, FIG. 50 provides a graphical illustrative view of a frequency threshold.

In yet another aspect, the tissue algorithm disclosed herein may be employed to monitor the frequency slope change and the frequency threshold in combination. The combination of a significant change in frequency slope and a drop in frequency below some threshold can be used to provide an indication of high temperature.

Figure 50:
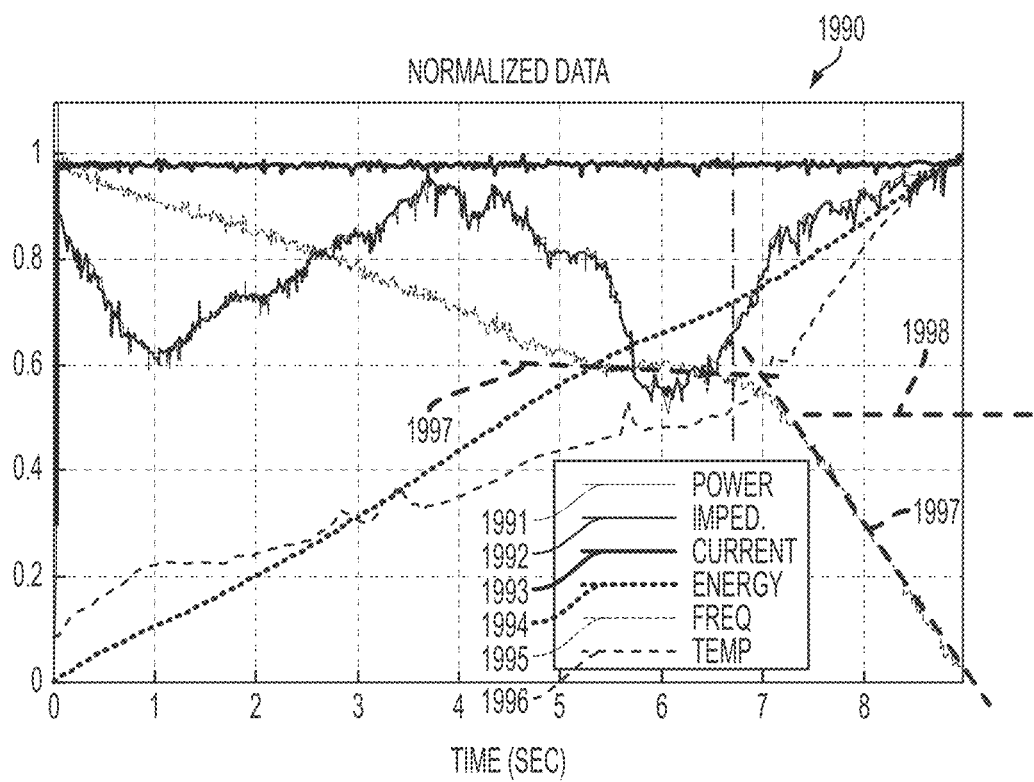
FIG. 50 is a graphical representation of normalized combined power, impedance, current, energy, frequency, and temperature waveforms of one embodiment of a generator coupled to an ultrasonic instrument.

Turning now to FIG. 50, is a graphical representation 1990 of normalized combined power 1991, impedance 1992, current 1993, energy 1994, frequency 1995, and temperature 1996 waveforms of one embodiment of a generator coupled to an ultrasonic instrument. As shown, the tissue begins to separate at 6.672 seconds. From this point until the tissue fully separates, about 55-60% of the total frequency drop is obtained, the temperature increases by a factor of about 1.92 (from 219° C. to 418° C.) and about 28% of the total energy applied is delivered. The local slopes of the frequency vs. time waveforms are shown by a first set of dashed lines 1997, which represents a rapid change in the resonant frequency slope. Monitoring this slope 1997 affords the opportunity to indicate a dramatic change which typically occurs when there is limited to no intervening tissue and the vast majority of power is being applied to the blade/tissue pad interface. Likewise, the frequency change from its resonance in a known state (e.g., room temperature) can be used to indicate high temperatures—a frequency change threshold is shown with a second dashed line 1998. Also, a combination of these two, frequency slope change and frequency change threshold, can be monitored for purposes of indication. Note that the frequency changes in this case from an initial value of 55,712 Hz to an end value of 55,168 Hz with the threshold shown at about 55,400 Hz.

While several embodiments have been illustrated and described, it is not the intention of the applicant to restrict or limit the scope of the appended claims to such detail. Numerous variations, changes, and substitutions will occur to those skilled in the art without departing from the scope of the invention. Moreover, the structure of each element associated with the described embodiments can be alternatively described as a means for providing the function performed by the element. Accordingly, it is intended that the described embodiments be limited only by the scope of the appended claims.

Reference throughout the specification to "various embodiments," "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

The invention claimed is:

1. A generator, comprising:
    an interface to electrically couple to an ultrasonic surgical instrument comprising a switch, wherein the switch is configurable between a first switch state and a second switch state; and
    a control circuit, to:
        provide a continuous drive signal to the ultrasonic surgical instrument based on the switch being in the first switch state; and
        provide a pulsed drive signal to the ultrasonic surgical instrument based on the switch being in the second switch state.

2. The generator of claim 1, wherein the continuous drive signal is at a power level less than a maximum power level of the generator.

3. The generator of claim 1, wherein the pulsed drive signal is at a maximum power level of the generator.

4. The generator of claim 1, wherein the continuous drive signal has a first power and the pulsed drive signal has a second power higher than the first power.

5. The generator of claim 1, wherein with respect to the pulsed drive signal, the generator is to provide:
    a first pulse having a first amplitude; and
    a second pulse having a second amplitude different than the first amplitude.

6. The generator of claim 5, wherein the first pulse is pulsed for a first pulse time, and wherein the second pulse is pulsed for a second pulse time different than the second pulse time.

7. The generator of claim 1, wherein with respect to the continuous drive signal, the generator is to provide:
    a first current for a first time;
    a second current for a second time after the first time, wherein the second current is higher than the first current; and
    a third current for a third time after the second time, wherein the third current is higher than the second current.

8. The generator of claim 1, wherein the control circuit is further to:
    monitor the continuous drive signal; and
    trigger a pulsing response based on the monitored drive signal meeting a logic condition.

9. The generator of claim 1, wherein the ultrasonic surgical instrument comprises an end effector and an ultrasonic transducer to resonate at a resonant frequency, and wherein with respect to the continuous drive signal, the control circuit is to:
    set the continuous drive signal to a first frequency for a first time, wherein the first frequency is different from the resonant frequency; and
    after the first time, set the continuous drive signal to the resonant frequency.

10. A generator for use with an ultrasonic surgical instrument comprising a switch, the switch configurable between a first switch state and a second switch state, wherein the generator comprises:
    a control circuit, to:
        provide a continuous drive signal to the ultrasonic surgical instrument based on the switch being in the first switch state; and
        provide a pulsed drive signal to the ultrasonic surgical instrument based on the switch being in the second switch state.

11. The generator of claim 10, wherein the continuous drive signal is at a power level less than a maximum power level of the generator.

12. The generator of claim 10, wherein the pulsed drive signal is at a maximum power level for the generator.

13. The generator of claim 10, wherein the continuous drive signal has a first power and the pulsed drive signal has a second power higher than the first power.

14. The generator of claim 10, wherein with respect to the pulsed drive signal, the generator is to provide:
    a first pulse having a first amplitude; and
    a second pulse having a second amplitude different than the first amplitude.

15. The generator of claim 14, wherein the first pulse is pulsed for a first pulse time, and wherein the second pulse is pulsed for a second pulse time different than the second pulse time.

16. The generator of claim 10, wherein with respect to the continuous drive signal, the generator is to provide:
    a first current for a first time;
    a second current for a second time after the first time, wherein the second current is higher than the first current; and
    a third current for a third time after the second time, wherein the third current is higher than the second current.

17. The generator of claim 10, wherein the control circuit is further to:
    monitor the continuous drive signal; and
    trigger a pulsing response based on the monitored drive signal meeting a logic condition.

18. The generator of claim 10, wherein the ultrasonic surgical instrument comprises an end effector and an ultrasonic transducer to resonate at a resonant frequency, and wherein with respect to the continuous drive signal, the control circuit is to:
    set the continuous drive signal to a first frequency for a first time, wherein the first frequency is different from the resonant frequency; and
    after the first time, set the continuous drive signal to the resonant frequency.

19. A generator, comprising:
    an interface to electrically couple to an ultrasonic surgical instrument comprising an ultrasonic transducer and a switch, the switch configurable between a first switch state and a second switch state; and a control circuit, to:
   provide a continuous drive signal to the ultrasonic transducer based on the switch being in the first switch state; and
   provide a pulsed drive signal to the ultrasonic transducer based on the switch being in the second switch state.

20. The generator of claim 19, wherein the continuous drive signal has a first power and the pulsed drive signal has a second power higher than the first power.

* * * * *